(12) United States Patent
Sauer et al.

(10) Patent No.: US 11,284,880 B2
(45) Date of Patent: Mar. 29, 2022

(54) DEVICES FOR CARDIAC SURGERY AND METHODS THEREOF

(71) Applicant: LSI Solutions, Inc., Victor, NY (US)

(72) Inventors: Jude S. Sauer, Pittsford, NY (US); Angelo John Martellaro, Victor, NY (US); Jeremy A. Schiele, Fairport, NY (US)

(73) Assignee: LSI Solutions, Inc., Victor, NY (US)

( * ) Notice: Subject to any disclaimer, the term of this patent is extended or adjusted under 35 U.S.C. 154(b) by 30 days.

(21) Appl. No.: 16/380,755

(22) Filed: Apr. 10, 2019

(65) Prior Publication Data

US 2019/0307442 A1 Oct. 10, 2019

Related U.S. Application Data

(60) Provisional application No. 62/790,663, filed on Jan. 10, 2019, provisional application No. 62/747,095, (Continued)

(51) Int. Cl.
  *A61B 17/02* (2006.01)
  *A61B 17/04* (2006.01)
  *A61B 17/00* (2006.01)

(52) U.S. Cl.
  CPC ...... *A61B 17/0469* (2013.01); *A61B 17/0218* (2013.01); *A61B 2017/00243* (2013.01); (Continued)

(58) Field of Classification Search
  CPC ............ A61B 17/0469; A61B 17/0218; A61B 2017/0237; A61B 2017/00243; A61B 2017/00424; A61B 2017/0472; A61B 2017/00477; A61B 90/90; A61B 90/92; A61B 90/94; A61B 17/0293; A61B 17/0483; A61B 2017/00473; A61B 17/0482
  See application file for complete search history.

(56) References Cited

U.S. PATENT DOCUMENTS 5,846,254 A * 12/1998 Schulze ............. A61B 17/0483
  606/148
6,371,911 B1 * 4/2002 Hossain ............. A61B 17/0206
  600/231

(Continued)

OTHER PUBLICATIONS

Product Literature; Jan. 1, 2010; IZZAT, Bashar, Geister Performance needs space . . . Izzat Spring Retractor.

(Continued)

*Primary Examiner* — Shaun L David
*Assistant Examiner* — Joshua T Hicks
(74) *Attorney, Agent, or Firm* — Michael E. Coyne; Christopher B. Miller

(57) ABSTRACT

A device for cardiac surgery is disclosed. The device for cardiac surgery includes an aortic root retractor frame, an introducer, and one or more suture locking apparatuses. The device for cardiac surgery also includes an actuator for releasing the aortic root retractor frame, as well as a deployment mechanism for fully expanding the aortic root retractor frame. Multiple suture locking apparatuses used for releasable locking and unlocking of suture during a cardiac surgery procedure may be included in the device for cardiac surgery.

14 Claims, 50 Drawing Sheets

Related U.S. Application Data filed on Oct. 17, 2018, provisional application No. 62/655,650, filed on Apr. 10, 2018.

(52) U.S. Cl.
CPC .............. *A61B 2017/00424* (2013.01); *A61B 2017/0237* (2013.01); *A61B 2017/0472* (2013.01)

(56) References Cited

U.S. PATENT DOCUMENTS

| | | | |
|---|---|---|---|
| 7,288,065 B1 * | 10/2007 | Taylor | A61B 17/0206 600/232 |
| 7,569,062 B1 | 8/2009 | Kuehn | |
| 7,758,500 B2 | 7/2010 | Boyd | |
| 8,388,525 B2 | 3/2013 | Poo | |
| 9,079,006 B1 | 7/2015 | Ovcharchyn | |
| 9,486,133 B2 * | 11/2016 | Lee | A61B 17/0206 |
| 9,789,289 B2 | 10/2017 | Bornhoft | |
| 2006/0036232 A1 * | 2/2006 | Primavera | A61B 17/0469 604/411 |
| 2010/0286485 A1 * | 11/2010 | Valentini | A61B 1/32 600/224 |
| 2011/0137128 A1 * | 6/2011 | Poo | A61B 17/0293 600/206 |
| 2015/0018625 A1 * | 1/2015 | Miraki | A61B 17/0206 600/208 |
| 2017/0065266 A1 | 3/2017 | Landanger | |

OTHER PUBLICATIONS

Product Literature; Jan. 1, 2017; Miami Instruments, Miami Instruments: Aortic Root Exposure Device.

* cited by examiner

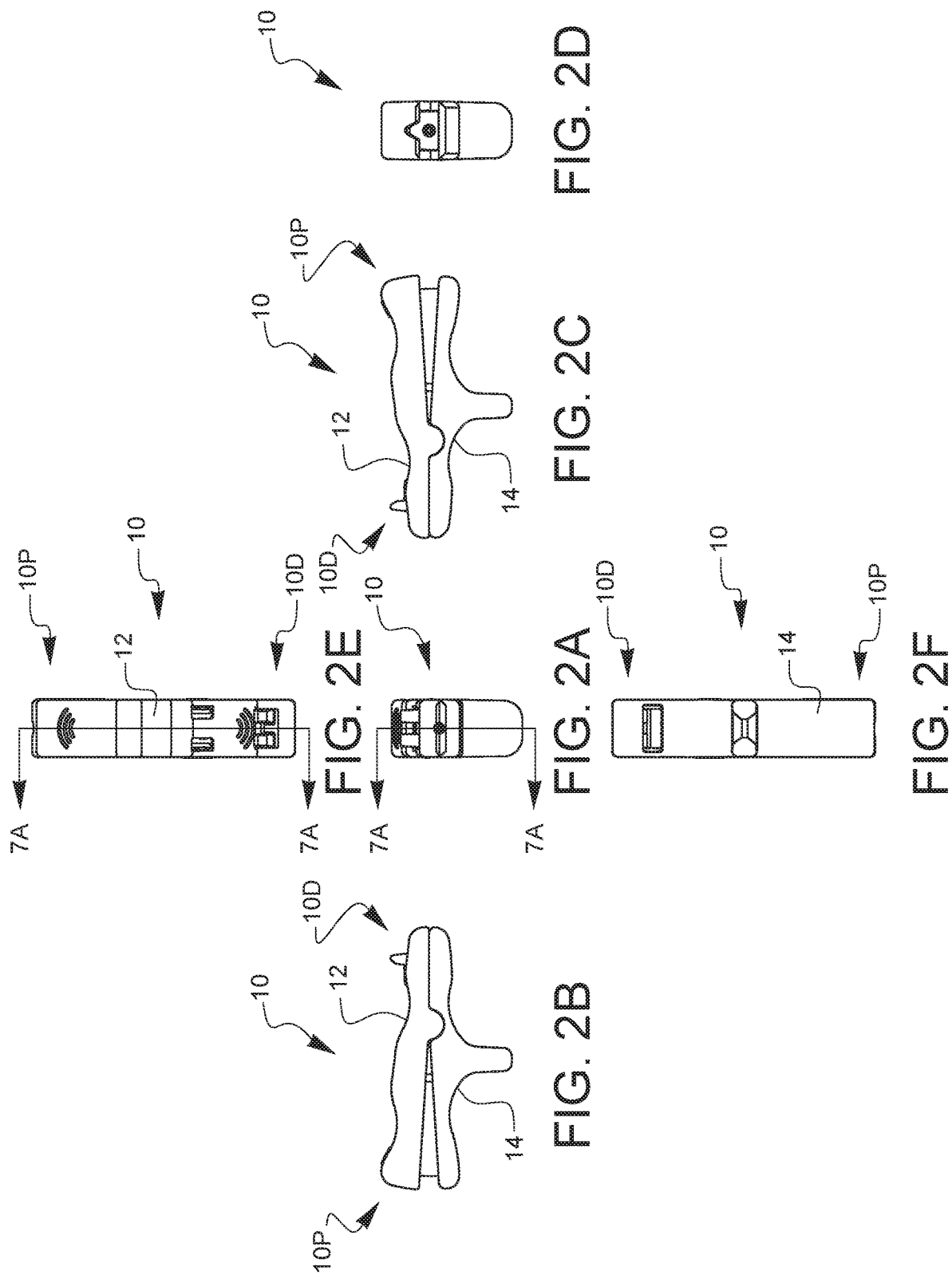

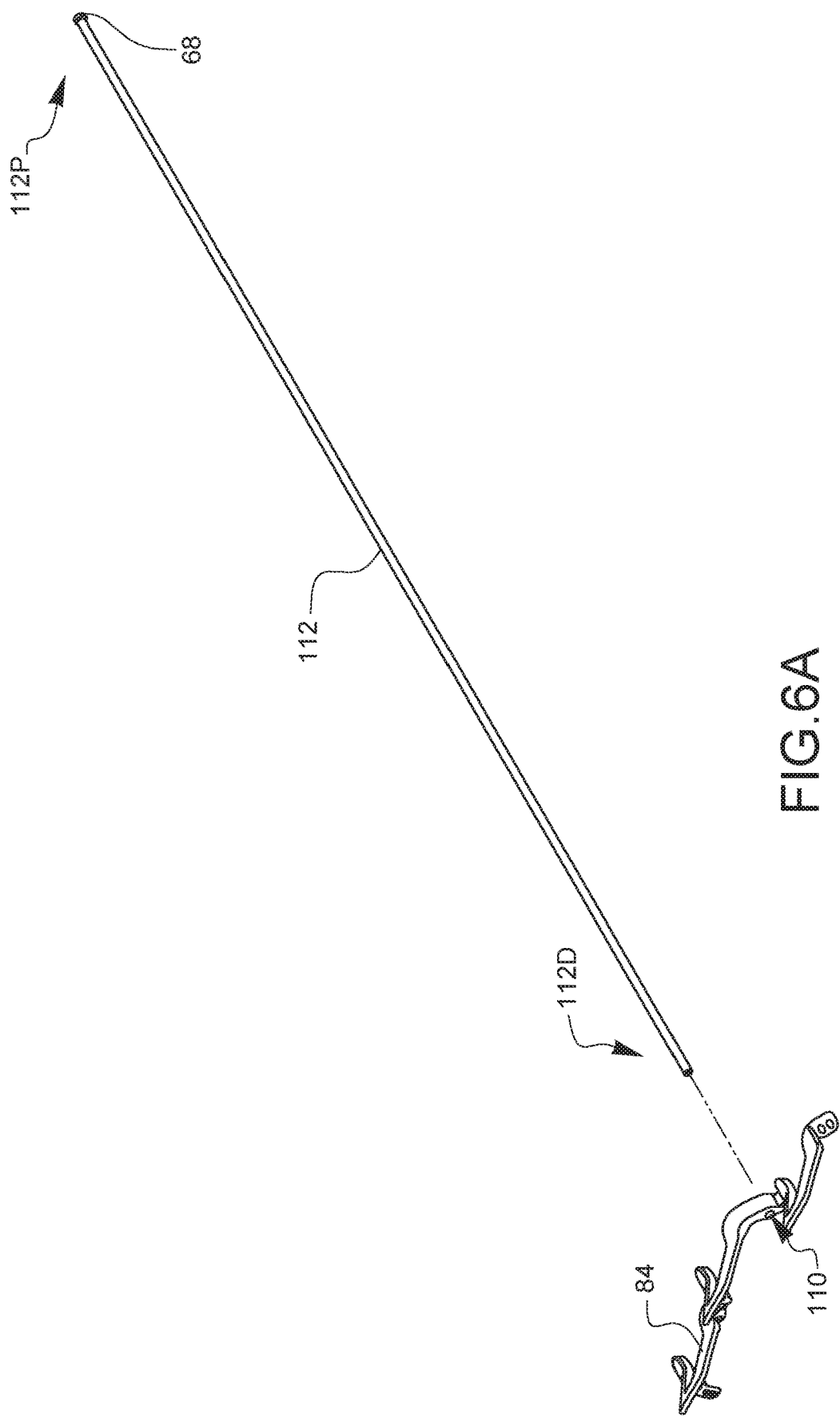

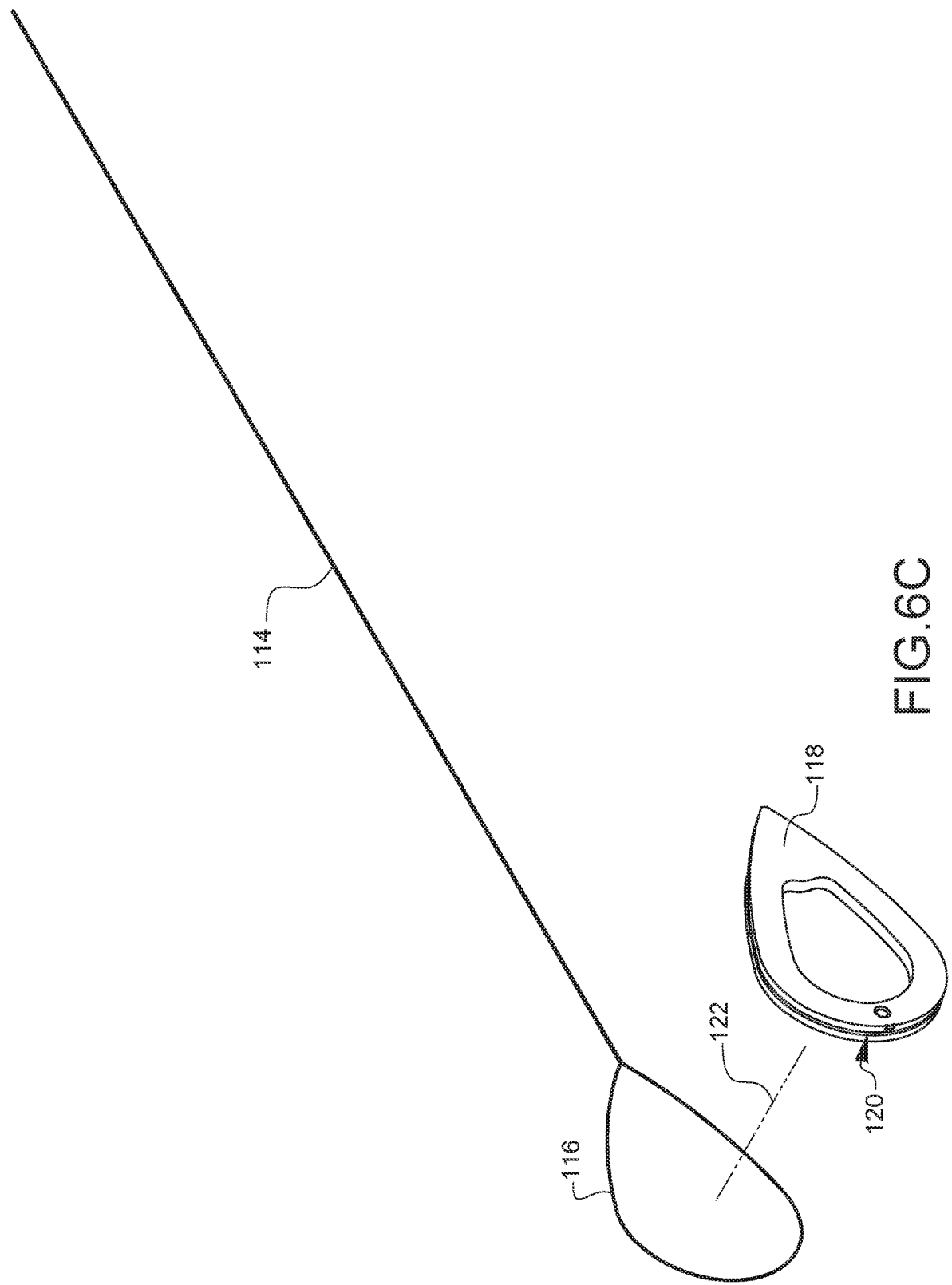

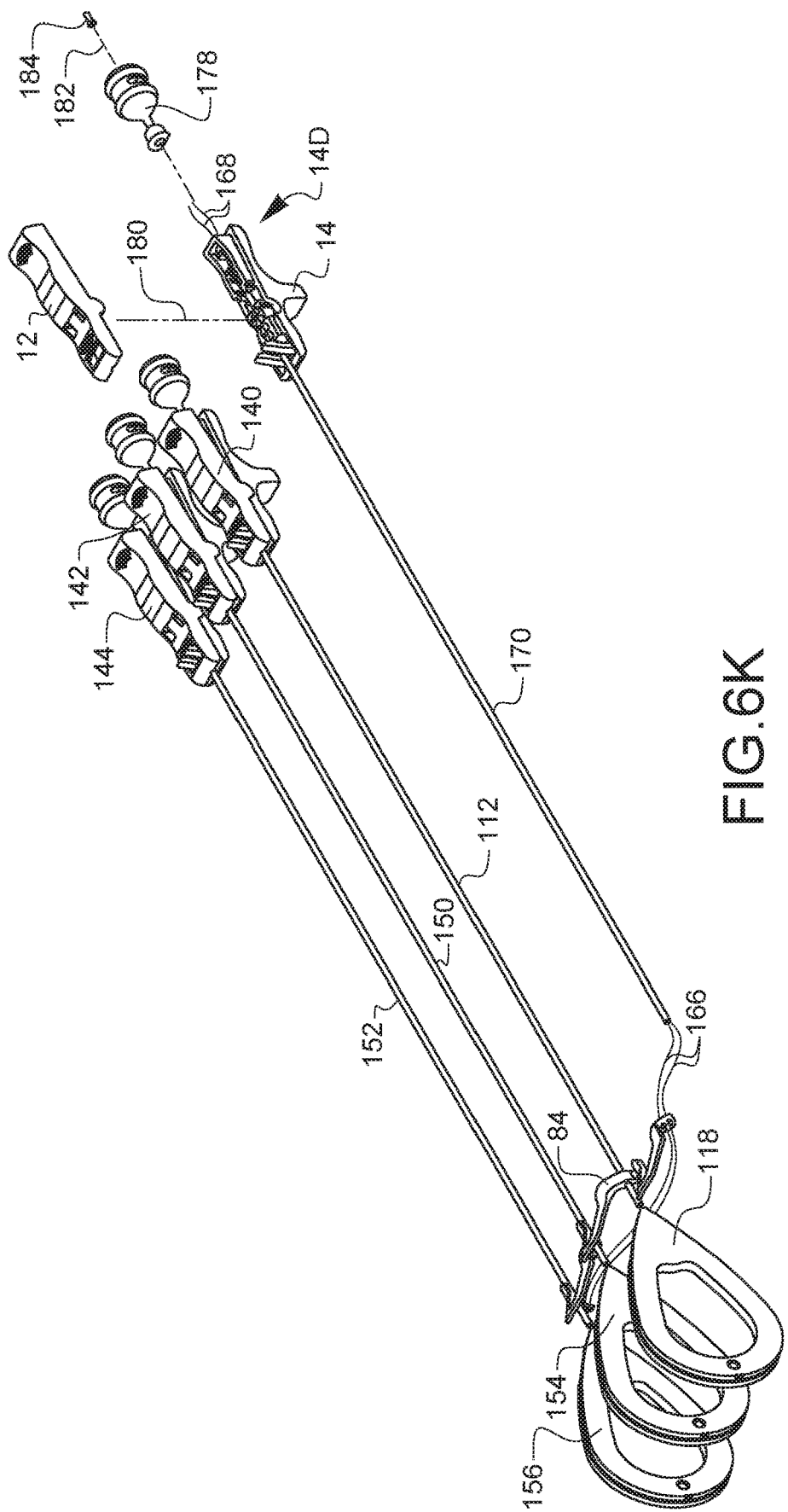

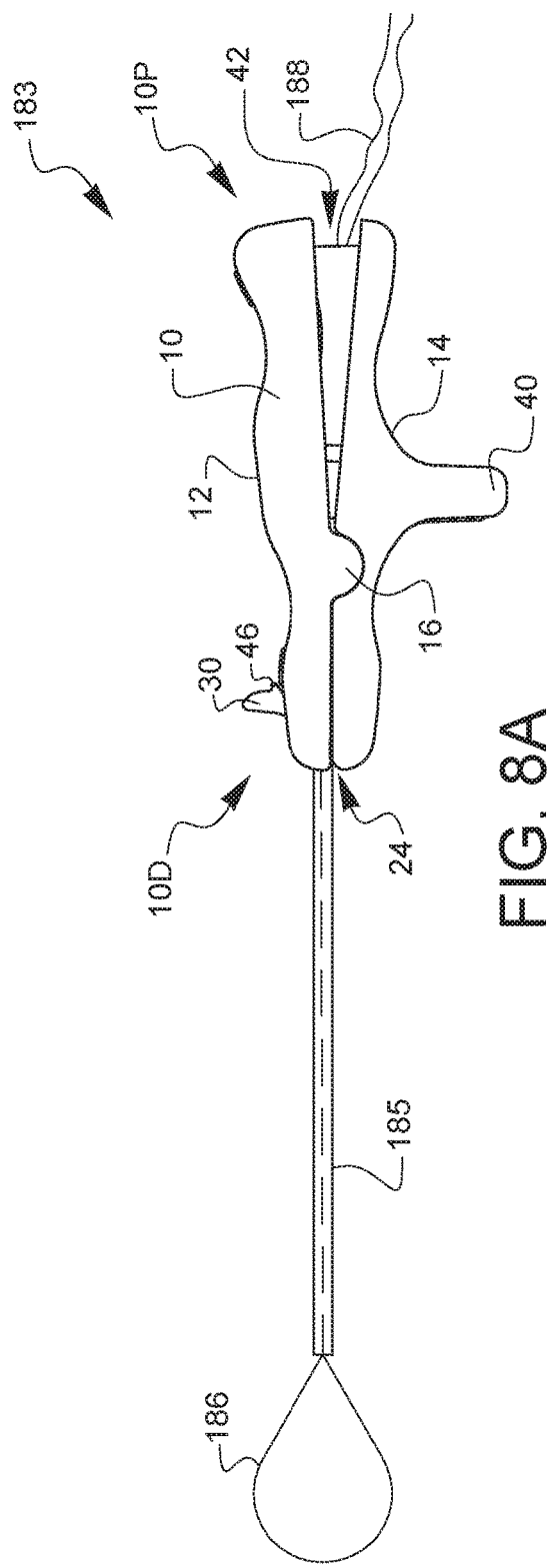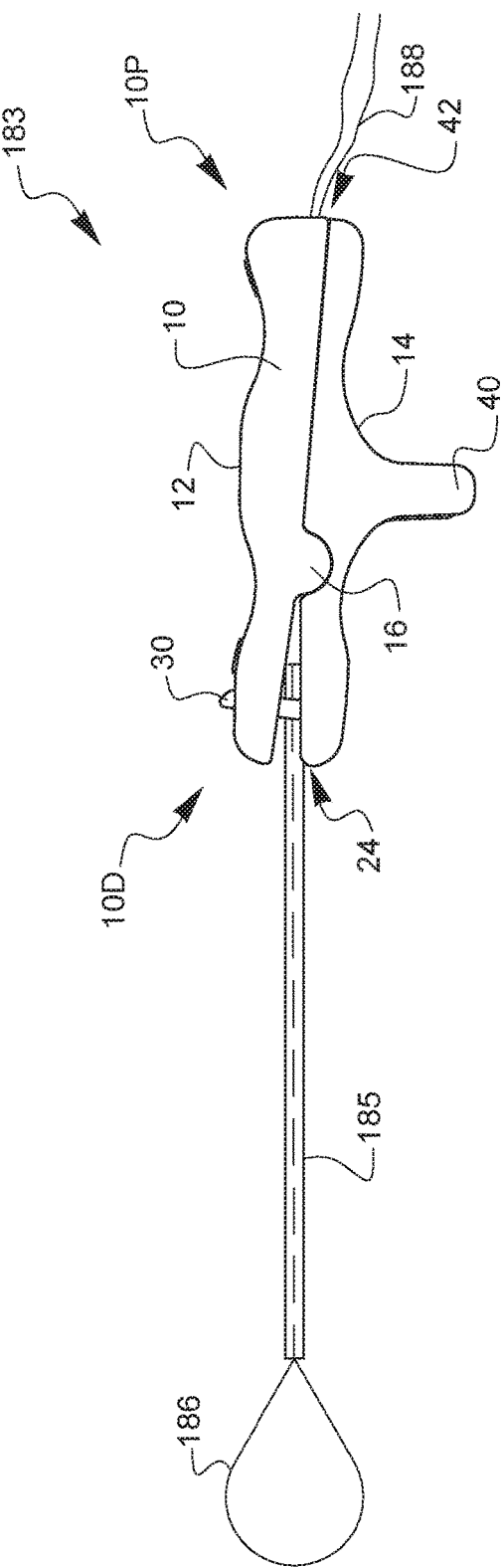
FIG. 8A
FIG. 8B

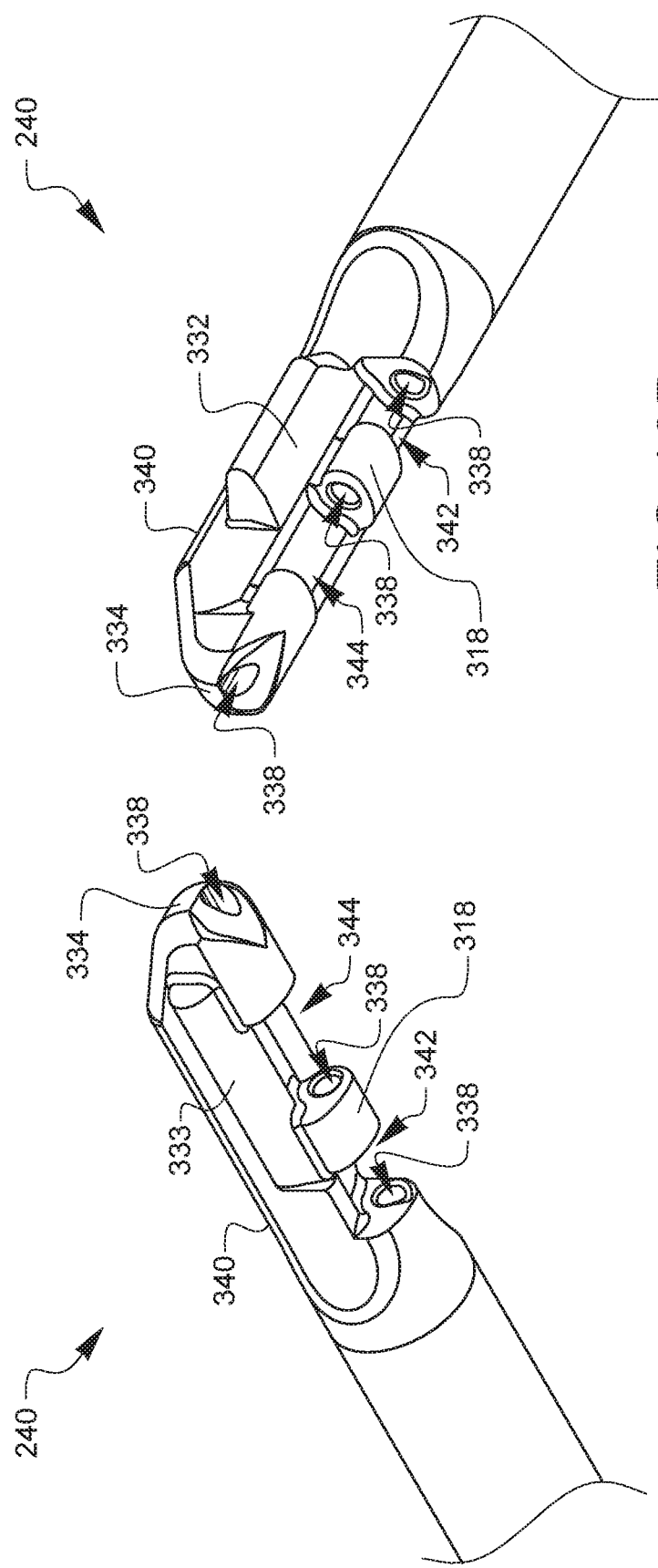

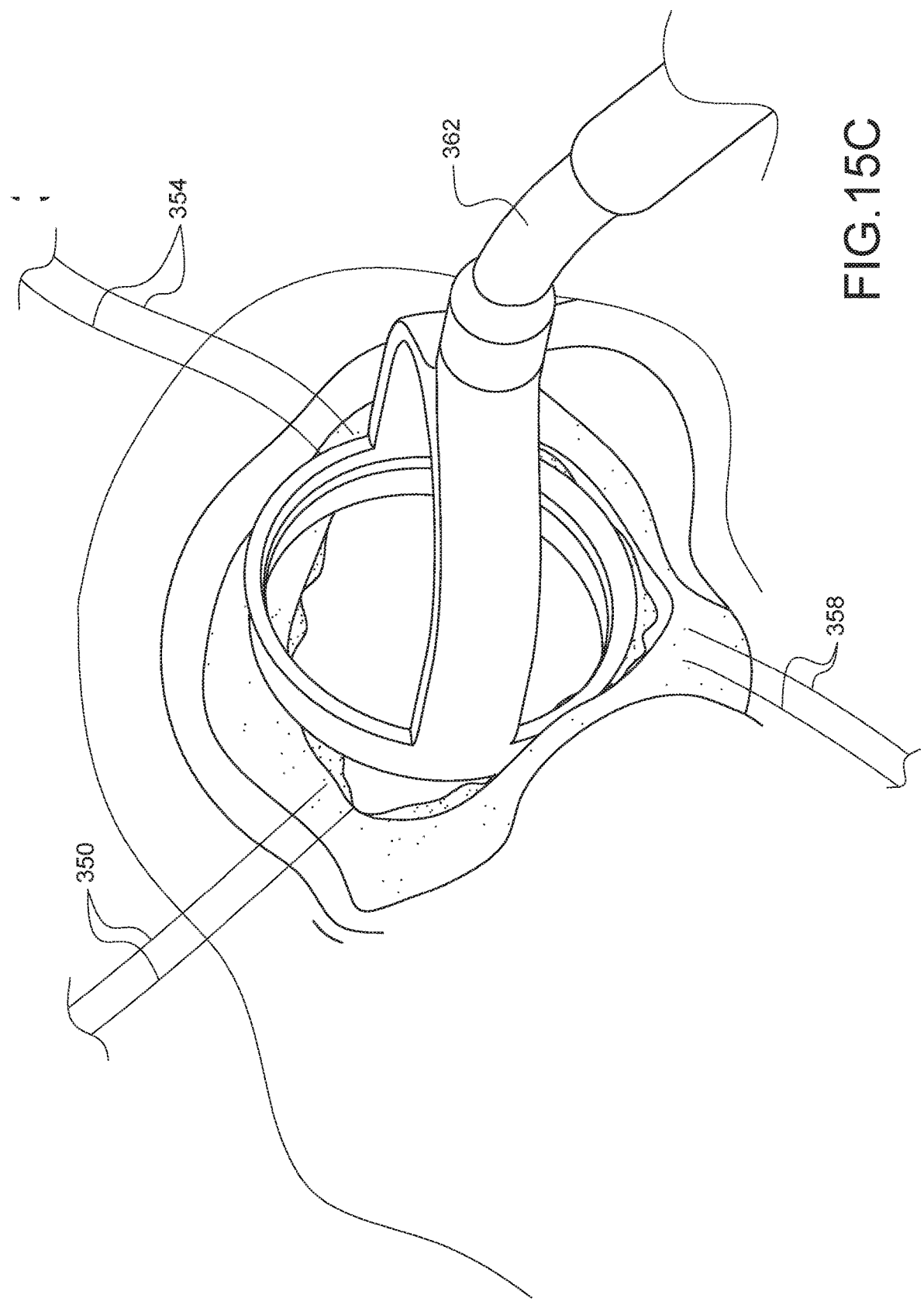

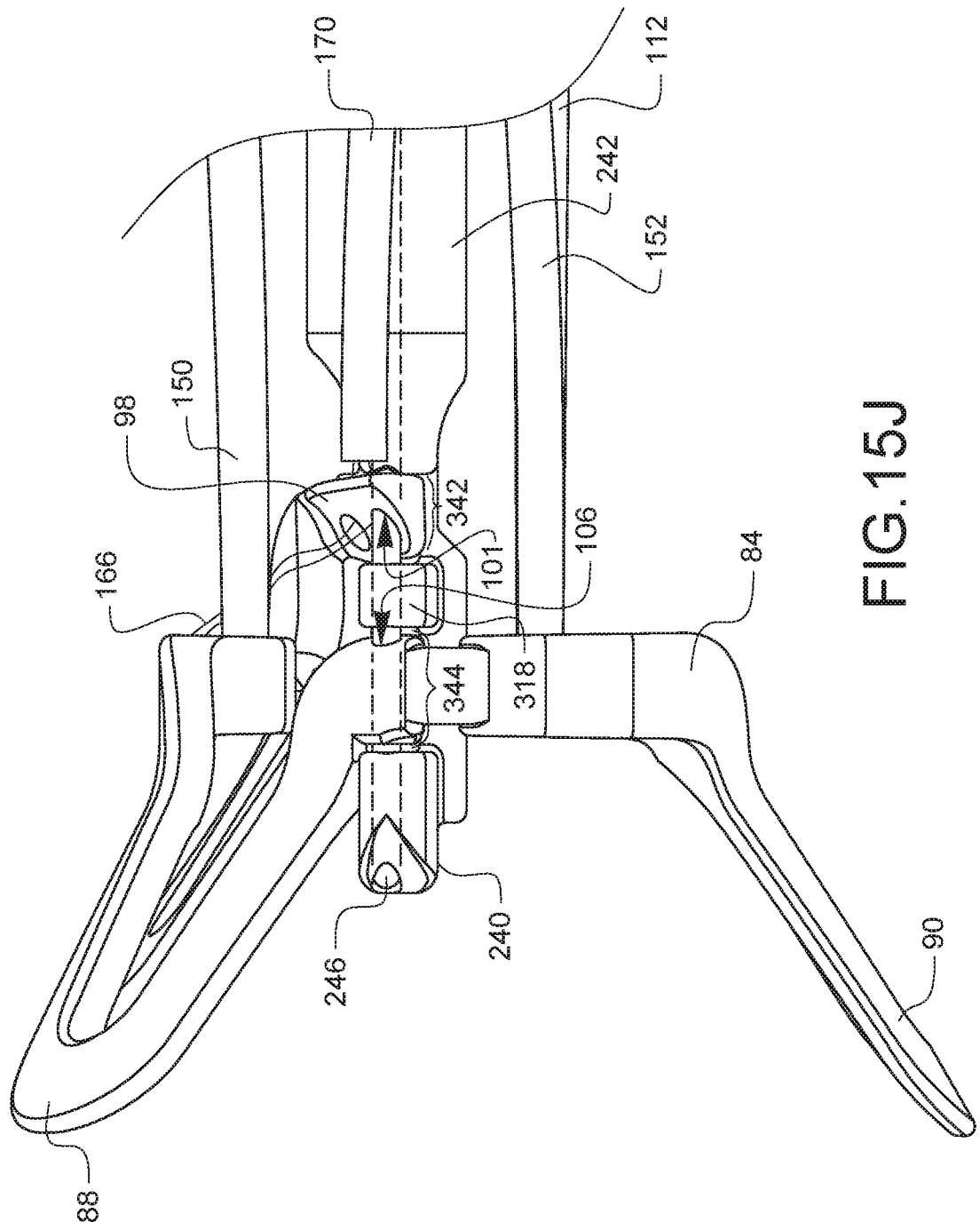

DEVICES FOR CARDIAC SURGERY AND METHODS THEREOF

RELATED APPLICATIONS

This application claims priority to U.S. Provisional Patent Application No. 62/655,650 filed Apr. 10, 2018 and entitled, "SUTURE LOCKING APPARATUS AND METHODS THEREOF." This application also claims priority to U.S. Provisional Patent Application No. 62/747,095 filed Oct. 17, 2018 and entitled, "DEVICES FOR CARDIAC SURGERY AND METHODS THEREOF." This application further claims priority to U.S. Provisional Patent Application No. 62/790,663 filed Jan. 10, 2019 and entitled, "DEVICES FOR CARDIAC SURGERY AND METHODS THEREOF." The entire 62/655,650, 62/747,095, and 62/790,663 applications are hereby incorporated by reference in their entirety.

FIELD

The claimed invention relates to surgical devices, and more specifically to devices for cardiac surgery and methods thereof.

BACKGROUND

Various types of surgery require a surgeon to place and temporarily secure a suture during a given surgical procedure. For example, prior to cannulation in cardiac surgery, surgeons often place one or more purse string sutures around a target tissue site before an incision will be made for a cannula to be inserted. Then, after the incision is made at the target site and the cannula has been inserted, the one or more purse string sutures are cinched to pull the tissue against the cannula to ensure there is a good seal around the cannula. Since the cannula will be removed before the end of the procedure, it is not efficient to tie a knot in the suture ends holding the tissue against the cannula, since they will soon need to be untied. Furthermore, during a minimally invasive surgical technique, the surgical team may not have direct access to the suture where it exits the tissue, so it can be difficult to maintain a cinched pressure around the cannula.

One solution employed by surgeons in this situation is the use of a simple tube. The suture ends to be temporarily cinched are passed through a thin tube which reaches from the surgical site to a convenient location away from the surgical site. A distal end of the tube is placed against tissue where the suture exits the tissue and, while holding a proximal end of the tube, the suture ends exiting the proximal end of the tube are pulled to create a desired tension of the suture on the tissue near the distal end of the tube. Then, the proximal end of the tube is clamped with a mosquito clamp to maintain tension on the suture until it is desired to release the tension.

To provide selective locking of suture ends when working with tubes as described above, separate clamps or forceps are used. Unfortunately, when such devices are used to clamp a tube, the clamping efficacy can vary depending on the type of clamp selected, the age of the clamp, and even what part of the clamp's jaw is used to secure the tube. Since such clamp and tube combinations for suture management are often used to secure cannulation devices for cardio-pulmonary bypass, as well as during other procedures, it would be desirable to have a more robust, reliable, and easy-to-use suture locking apparatus.

In other types of cardiac surgery, it is often desirable to access the aortic valve and/or left ventricle of the heart through a portion of the aorta. In order to create an aortotomy (incision through the aorta), it is first necessary to securely clamp and/or occlude the aorta away from the heart, place the patient on bypass perfusion, and temporarily stop the heart from beating, for example, with cardioplegia. The aortotomy depressurizes the aorta and can cause the walls of the aorta to flop down after an incision is made in the aorta, thereby having the potential to block the surgeon's view of the aortic valve through the incision. Furthermore, even when the flaps of the aorta around the incision are held out of the way, it can still be difficult to see the aortic root where the leaflets of the aortic valve are attached to the heart. Therefore, it would be helpful if there were a device for cardiac surgery which could help to increase a surgeon's visualization of the aortic root in a minimally invasive surgical procedure.

SUMMARY

A device for cardiac surgery is disclosed. The device for cardiac surgery includes an aortic root retractor frame; an introducer; one or more suture locking apparatuses; and a frame deployment mechanism.

A suture locking apparatus is also disclosed. The suture locking apparatus includes an upper housing having a first gripping surface, a lower housing coupled to the upper housing and having a second gripping surface, and a latch.

A method of stabilizing cardiac tissue is also disclosed. The method of stabilizing cardiac tissue includes placing three commissural sutures in each of three commissures in an aortic annulus; loading each of the three commissural sutures into corresponding but separate suture locking apparatuses coupled to an aortic root retractor frame; delivering and positioning the aortic root retractor frame into an aortic root; tensioning and locking the commissural sutures into the corresponding suture locking apparatuses; and deploying the aortic root retractor frame using a deployment suture coupled to the aortic root retractor frame.

BRIEF DESCRIPTION OF THE DRAWINGS

FIGS. 2A, 2B, 2C, 2D, 2E, and 2F are front, left side, right side, rear, top, and bottom elevational views, respectively, of the suture locking apparatus of FIG. 1A in an unlocked position.

FIGS. 6A-6H, and 6J-6K are a series of exploded views illustrating the assembly of one embodiment of an aortic root retractor which includes the aortic root retractor frame of FIGS. 5A-5B and a plurality of suture locking apparatuses of FIGS. 1A-1B. FIG. 6I was not used to avoid confusion with numeral one.

FIGS. 8A-8B are right-side elevational views of a suture locking device which includes the suture locking apparatus of FIG. 1A in an unlocked and locked position, respectively.

FIGS. 13A and 13B are distal-bottom-left and distal-bottom right perspective views of the introducer end of the aortic root retractor (ARR) delivery device of FIG. 11, respectively.

FIGS. 15A-15H, 15J-15N, and 15P-15Q are a series of views detailing portions of a surgical procedure using the aortic root retractor (ARR) delivery device of FIG. 11. FIGS. 15I and 15O were not used to avoid confusion with numerals one and zero, respectively.

Figure 1A:
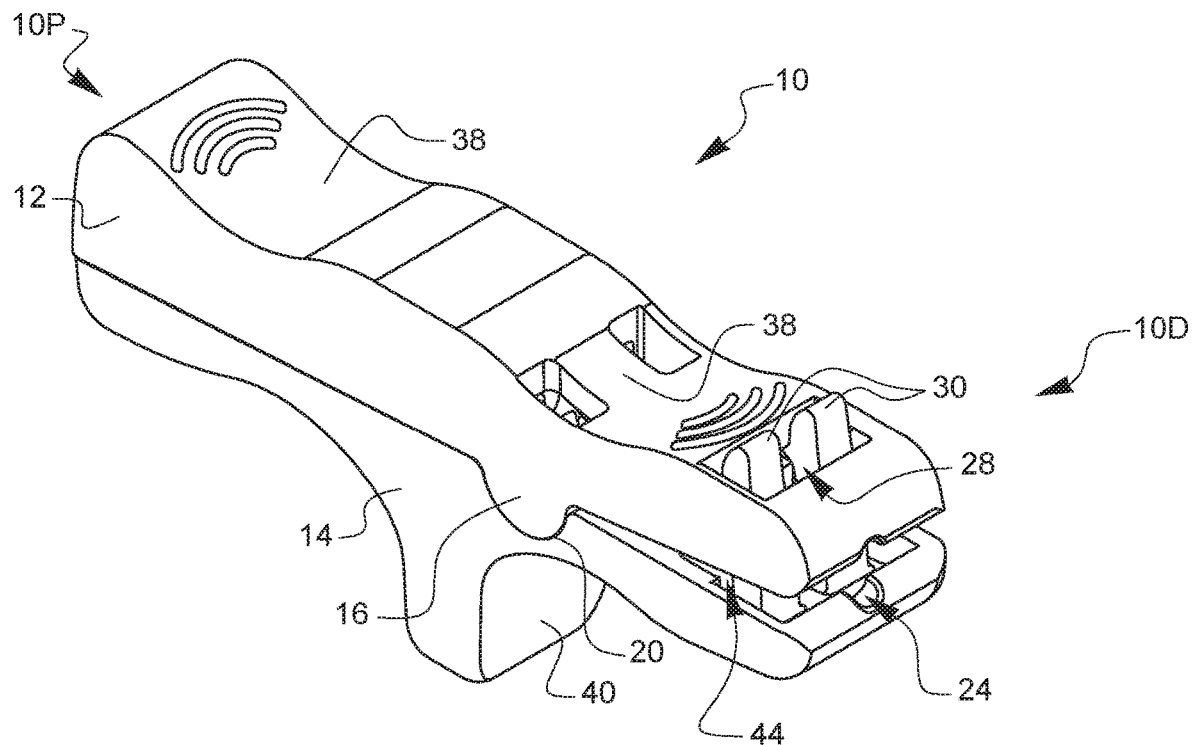
FIGS. 1A-1B are distal-top-left and proximal-top-right perspective views, respectively, of an embodiment of a suture locking apparatus.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

FIG. 1A is a distal-top-left perspective view of an embodiment of a suture locking apparatus 10. The suture locking apparatus 10 has an upper housing 12 coupled to a lower housing 14. In this embodiment of the suture locking apparatus 10, the upper housing 12 is pivotably coupled to the lower housing 14 by resting a hinge 16 of the upper housing 12 within a cradle 20 defined by the lower housing 14. In other embodiments, the lower housing 14 may have a hinge resting in a cradle 20 defined by the upper housing 12. Depending on the embodiment, the upper housing 12 and lower housing 14 may be pivotably coupled at a distal end 10D of the suture locking apparatus 10, a proximal end 10P of the suture locking apparatus 10, or any location in between. In other embodiments, the lower housing 14 and the upper housing 12 may be coupled with a continuous living hinge.

A distal aperture 24 configured to receive a suture and a suture tube 66 (not shown in FIG. 1A), is defined by the lower housing 14 and the upper housing 12. This distal aperture 24 directs a suture or a suture tube into an internal channel 50 or suture channel (not shown in FIG. 1A but discussed later). For the purposes of this disclosure, a distal direction or location refers to an orientation away from the surgeon or operator of the instrument. A proximal direction or location refers to an orientation towards the surgeon or operator of the instrument. It should be understood that the term "suture", as used herein, is intended to cover any thread, cable, wire, filament, strand, line, yarn, gut, or similar structure, whether natural and/or synthetic, in monofilament, composite filament, or multifilament form (whether braided, woven, twisted, or otherwise held together), as well as equivalents, substitutions, combinations, and pluralities thereof for such materials and structures.

Still on FIG. 1A, this embodiment of a suture locking apparatus 10 has a latch 28 on the distal portion of the suture locking apparatus 10. The lower housing 14 has one or more latch elements 30 configured to apply a force against a latch tab 46, not shown in FIG. 1A, but visible in FIG. 3A. The upper housing 12 defines a latch opening 70 configured to receive the latch elements 30. In another embodiment of the suture locking apparatus 10, it may be the upper housing 12 that comprises one or more latch elements, and the lower housing 14 that comprises a latch opening and a latch tab 46. Depending on the embodiment of the suture locking apparatus 10, one or more latch elements 30 may be present and the location of the latch 28 may be located on a proximal end 10P of the suture locking apparatus 10.

Figure 1B:
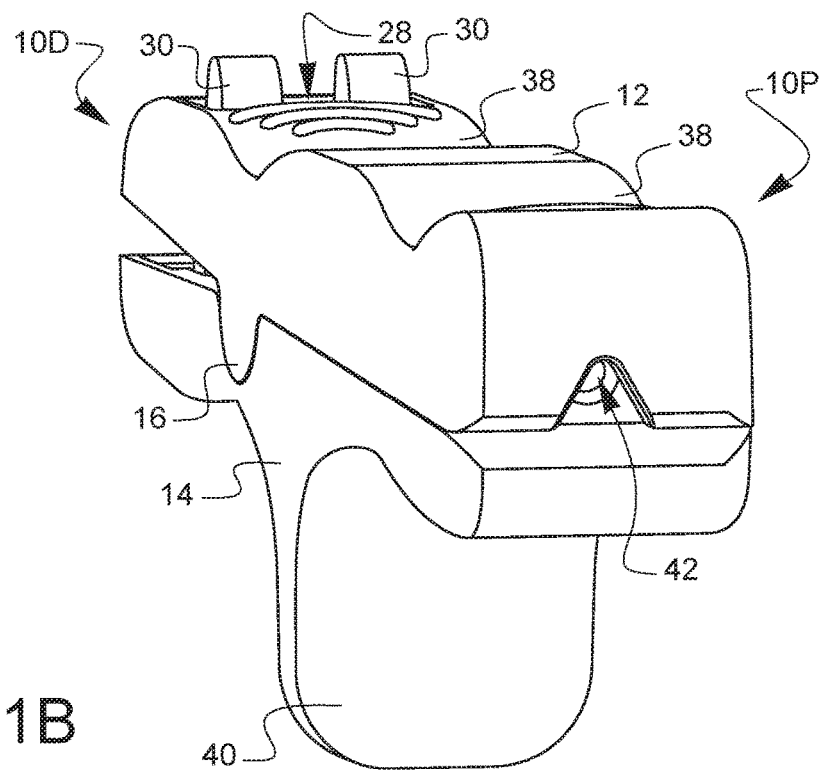

One or more features are included in this embodiment is configured to provide ergonomic comfort or leverage for the operator or user. For example, the upper housing 12 has several recesses 38 and the lower housing 14 has an ergonomic grip 40 for one or more digits of the user to rest upon or use as leverage during operation. In alternate embodiments, more than one ergonomic grip may be present in the lower housing 14, the upper housing 12 may have one or more ergonomic grips, and the lower housing 14 may have one or more recesses 38. Depending on the embodiment of the suture locking apparatus 10, either the upper housing 12 or the lower housing 14 may lack ergonomic features. FIG. 1B is a proximal-top-right perspective view of the suture locking apparatus 10 of FIG. 1A. This figure displays a proximal aperture 42 defined by the lower housing 14 and configured to allow a suture (not shown in this view) to pass freely therethrough when unlocked or be held securely in place when the locking mechanism is engaged. It should be noted that the proximal aperture 42 may be defined in a variety of alternate shapes or physical configurations.

FIGS. 2A, 2B, 2C, 2D, 2E, and 2F are front, left side, right side, rear, top, and bottom elevational views, respectively, of the suture locking apparatus of FIG. 1A in an unlocked position. The suture locking apparatus 10, its distal end 10D, proximal end 10P, upper housing 12, and lower housing 14 are indicated in FIGS. 2A, 2B, 2C, 2D, 2E, and 2F where possible. The section plane cross-section lines bisecting FIGS. 2A and 2E refer to the cross-section illustrated in FIG. 7A and will be further described in regard to FIG. 7A.

Figure 3A:
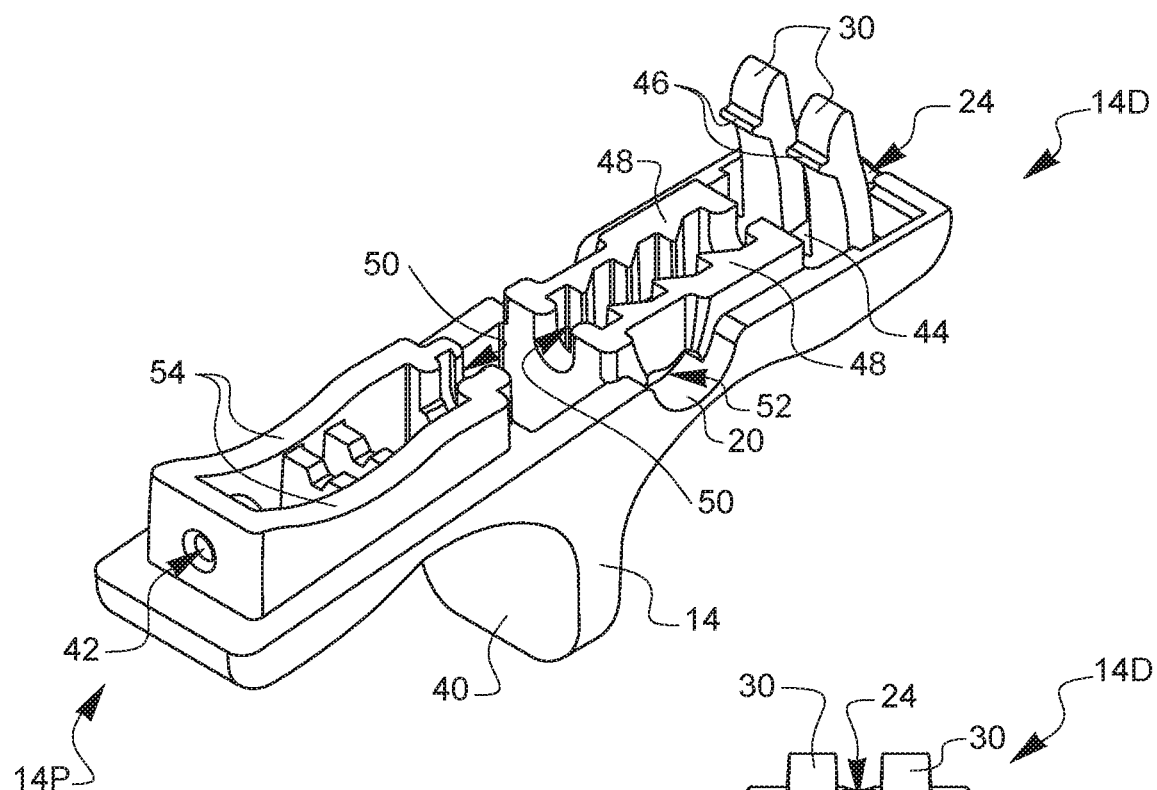
FIGS. 3A-3B are a proximal-top-left and proximal-top, perspective views, respectively, of the lower housing of the suture locking apparatus of FIGS. 1A-1B.

FIG. 3A is a proximal-top-left perspective view of the lower housing 14 of the suture locking apparatus 10 of FIG. 1A. The lower housing 14 defines a latch recess 44 to hold at least a portion of the one or more latch elements 30. The latch recess is sized and configured to allow flexure or motion of the latch elements 30 as required to move between their locked and unlocked position. The latch elements 30 and the latch tabs 46 are configured to hold the suture locking apparatus 10 in either the locked or unlocked position, which will be described later in regard to FIGS. 7A and 7B. The latch elements 30 engage the top surface of the upper housing 12 at the edge of the latch opening 70. Towards the distal end 14D of the lower housing 14 there are two distal support struts 48 configured to restrict the relative motion of the lower housing 14 and the upper housing 12 by limiting the angle the upper housing 12 pivots relative to the lower housing 14.

Figure 3B:
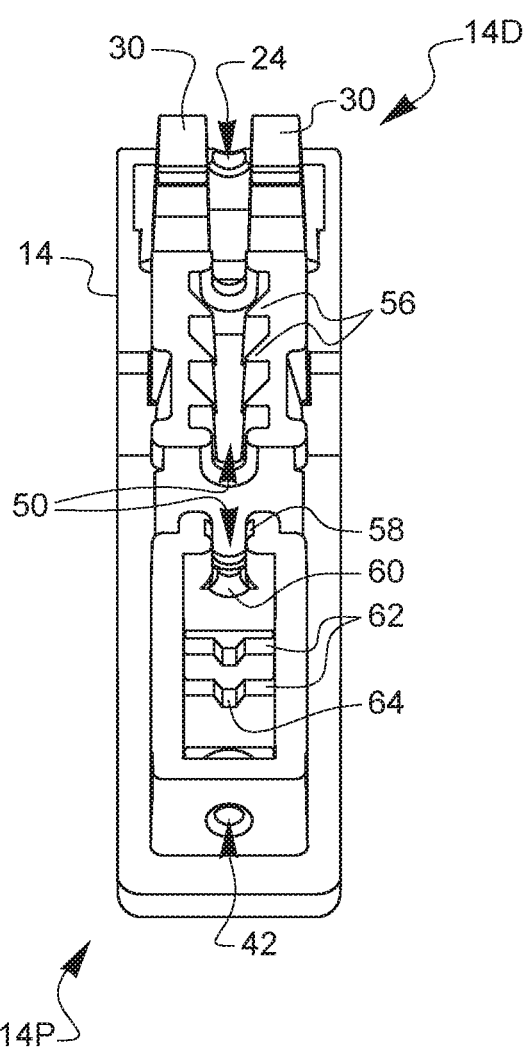

FIG. 3B is a proximal-top perspective view of the lower housing 14 of FIG. 3A. This view demonstrates further details of an internal suture channel 50 and other features configured to direct a suture (not shown in this view) into and through the suture locking apparatus 10. The lower housing 14 defines several interference barbs 56, a suture tube stop 60, a tube stop recess 58, lower teeth 62 each having a lower tooth recess 64. A suture tube 66 can be inserted into the distal aperture 24 and in connection with the channel 50 as a guide to entrain a suture within the suture locking apparatus 10. The suture tube 66 may be further directed through or constrained in the channel 50 by features such as the interference barbs 56. These interference barbs 56 or bumps are configured to provide additional holding force to prevent the unintentional removal of a suture tube 66 from the suture locking device. A sharper profile provides a one-way insertion path with additional resistance to removal through the channel 50. These interference barbs may have different shapes in alternate embodiments, such as rounded edges or sharper edges having different orientations. A suture tube 66 may be terminated with a metal flange, flared end or other fastener constructed to hold the suture in place within a tube stop 60 which delineates the channel 50 from the lower tooth recesses 64 in the lower housing 14 of the suture locking device. The tube stop 60 is defined by the lower housing 14, which also defines a tube stop recess 58 on either side for capturing a flange or flare on the end of a suture tube 66. One or more suture ends can be inserted or snared through the suture tube 66. The suture ends can then exit the suture locking apparatus 10 via the lower tooth recesses 64 defined by the lower teeth 62 and located in between two proximal support struts 54, and the proximal aperture 42 defined by the lower housing 14 at its proximal end 14P. While the present embodiment of a suture locking apparatus 10 shows a tube stop 60 at the approximate midpoint along the length of the lower housing 14, the tube stop 60 may be located in any place along the length of the suture path between the distal aperture 24 and the proximal aperture 42, and therefore the respective lengths and dimensions of the channel 50, lower tooth recesses 64, and other elements defined by the lower housing 14 may vary accordingly. In this embodiment, this channel 50 passes between the one or more latch elements 30, and the path the suture follows begins with the distal aperture 24 and sequentially follows through the channel 50, the lower tooth recesses 64 and exits at the proximal aperture 42.

Figure 3C:
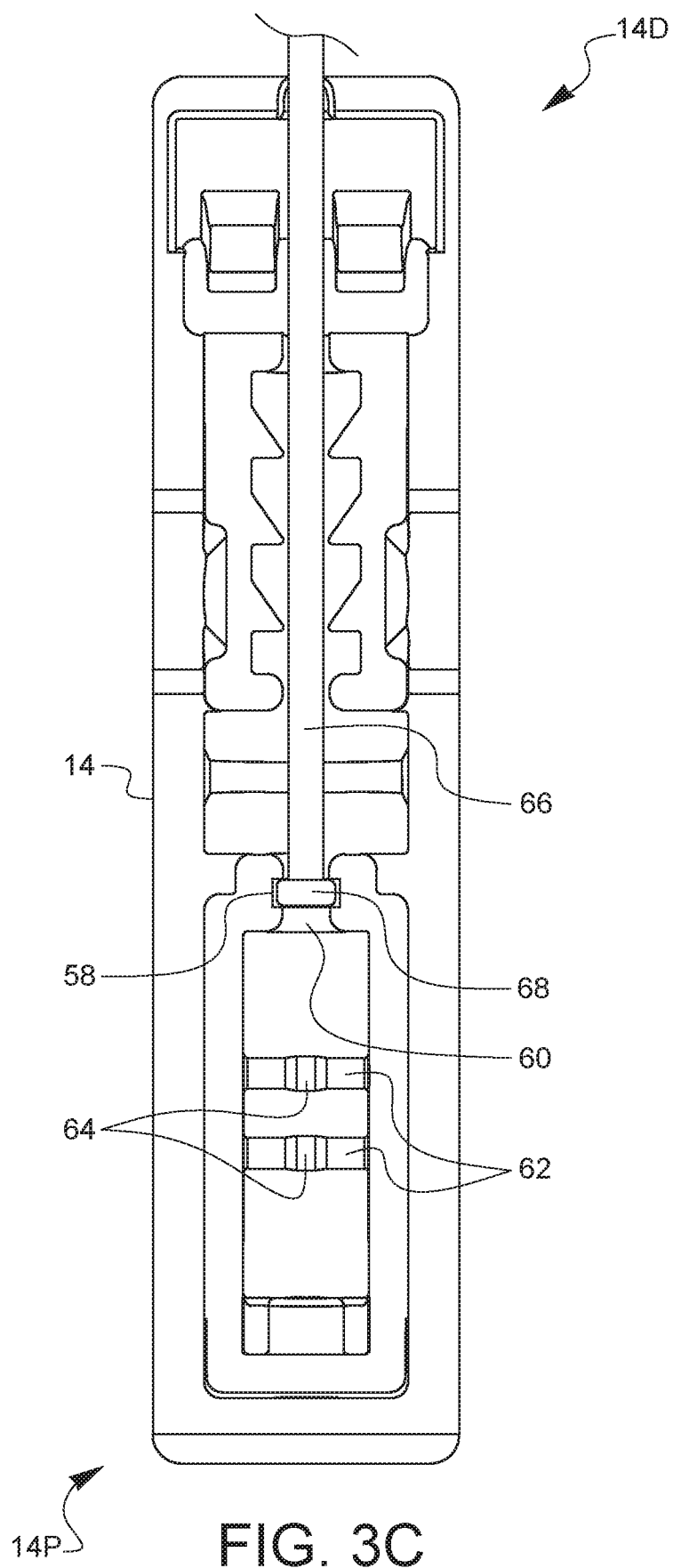
FIG. 3C is a top view of the lower housing of FIGS. 3A-3B with a suture tube added to the lower housing.

The lower teeth 62 and the lower tooth recesses 64 defined by the lower housing 14 in this embodiment form a lower gripping surface. The lower gripping surface as defined by the aforementioned features defined by the lower housing 14 may include one or more lower teeth 62. These one or more lower teeth 62 may take a wide variety of shapes and forms. For instance, the one or more lower teeth 62 may be formed of wedges, or of triangular saw teeth, but it will be apparent to those of ordinary skill in the art that these teeth may be formed of multiple shapes. The one or more lower teeth 62 may further define lower recesses configured to receive a suture that has exited a tube which terminates at the tube stop 60. In alternative embodiments, the lower gripping surface may instead include a support pad or alternate method of providing a resilient grip. Still other alternative embodiments may provide other means of providing sufficient holding force or a torturous pathway useful in restraining the movement of a suture within a suture locking apparatus. Other embodiments may have one, or up to five or ten teeth or other elements in the lower housing 14. The number and shape of elements included in a gripping surface is limited only by the dimensions of the suture locking apparatus 10 and the relative dimensions of the teeth or other elements defined by either the upper housing 12 or the lower housing 14. In other embodiments, proximal support struts 54 may extend from the proximal end 10P of the suture locking apparatus 10 to the distal end 10D of the suture locking apparatus 10. In some embodiments, the support struts may extend from a proximal end 10P of the suture locking apparatus 10 to the latch recess 44. FIG. 3C is a top view of the lower housing of FIGS. 3A-3B with a suture tube added to the lower housing. This view illustrates a suture tube 66 having a flared end 68 inserted into the suture locking device. The flared end is held within the tube stop 60 and tube stop recesses 58 defined by the lower housing 14. While the end of the tube has been flared using heating to fit it within the tube stop 60 and tube stop recesses 58, adhesive, heating, or both, as well as other means for fixing the suture tube 66 within the tube stop 60 and tube stop recesses 58 may be used for the assembly of this as well as similar assemblies as described herein.

Figure 4A:
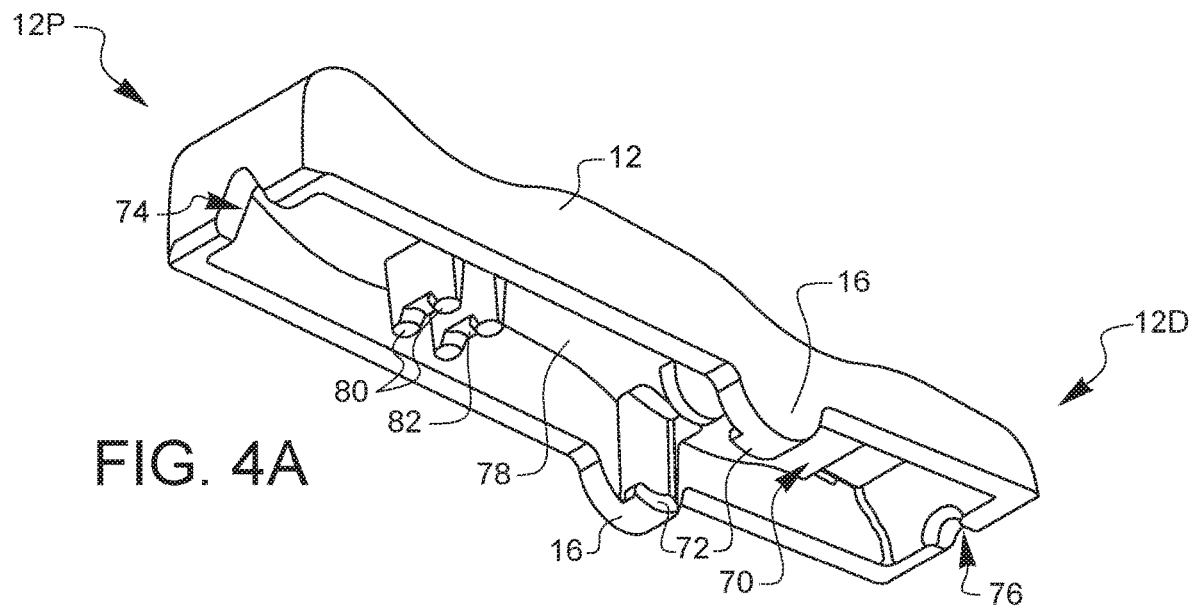
FIGS. 4A-4B are proximal-bottom-left and proximal-bottom perspective views, respectively, of the upper housing of the suture locking apparatus of FIGS. 1A-1B.

FIG. 4A is a proximal-bottom-left perspective view of upper housing 12 of the suture locking apparatus 10 of FIG. 1A. The upper housing 12 defines the latch opening 70, two hinges 16, a distal upper housing notch 76, a proximal upper housing notch 74, and an inner surface 78. The inner surface 78 defines two upper teeth 80 which each define an upper tooth recess 82. The upper teeth 80 are located towards the proximal end 12P of the upper housing 12. The hinges 16 further comprise hinge protrusions 72 configured to mate with cradle apertures 52 located in the lower housing 14, shown in FIG. 3A. The cradle apertures 52 are comprised of an arc wider than that of the arcuate hinge protrusions 72 to allow pivoting of the upper housing 12 relative to the lower housing 14. The distal upper housing notch 76 partially defines the distal aperture 24 and is configured to receive a suture tube 66 and a suture, not shown in this view. The upper teeth 80 and the upper tooth recesses 82 defined by the upper housing 12 in this embodiment form an upper gripping surface. The upper gripping surface as defined by the aforementioned features defined by the upper housing 12 may include one or more upper teeth 80. These one or more upper teeth 80 may take a wide variety of shapes and forms. For instance, the one or more upper teeth 80 may be formed of wedges, or of triangular saw teeth, but it will be apparent to those of ordinary skill in the art that these teeth may be formed of multiple shapes. The one or more upper teeth 80 may further define upper recesses configured to receive a suture that has exited a tube which terminates at the tube stop 60. In alternative embodiments, the upper gripping surface may instead include a support pad or alternate method of providing a resilient grip. Still other alternative embodiments may provide other means of providing sufficient holding force or a torturous pathway useful in restraining the movement of a suture within a suture locking apparatus. Other embodiments may have one, or up to five or ten teeth or other elements in the upper housing 12. The number and shape of elements included in a gripping surface is limited only by the dimensions of the suture locking apparatus 10 and the relative dimensions of the teeth or other elements defined by either the upper housing 12 or the lower housing 14. In a locked position, the upper teeth 80 interlock with the lower teeth 62 in a staggered fashion, restricting the suture in a tortuous path, which fixes the suture ends in place without allowing the suture ends to move in either direction. This is advantageous in a surgical procedure, as it locks the suture at the required tension desired by the operator, with no slippage. In an unlocked position, the upper gripping surfaces and the lower gripping surfaces are configured to allow unrestricted movement of a suture along a pathway defined by the distal notch 76, the channel 50, past the tube stop 60, through the lower tooth recesses 64 and finally via the proximal aperture 42 defined by the proximal upper housing notch 74. In this unlocked position, the upper teeth 80 and the lower teeth 62 are no longer interlocking, and allow the suture ends to move in either direction as desired by the operator.

Figure 4B:
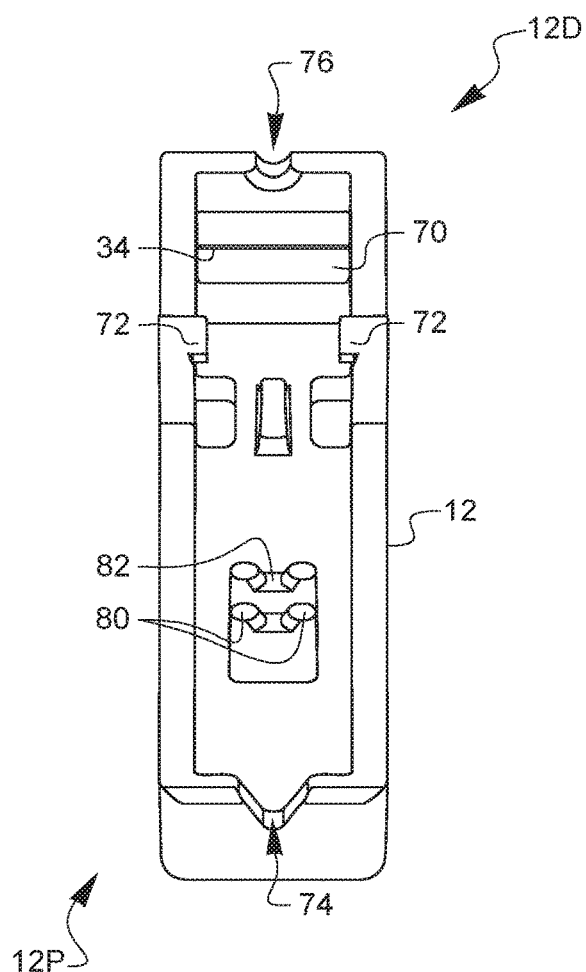

FIG. 4B is a proximal-bottom perspective view of the upper housing 12 of the suture locking apparatus 10 of FIG. 1A further detailing a latch step 34 located adjacent to the latch opening 70 in the upper housing 12. This latch step 34 is configured to hold the latch elements in a locked or unlocked position, as selected by the operator. The latch tabs are biased against the latch step 34 to provide resistance to engagement and disengagement of the latch elements unless intentionally selected by the operator.

Figure 5A:
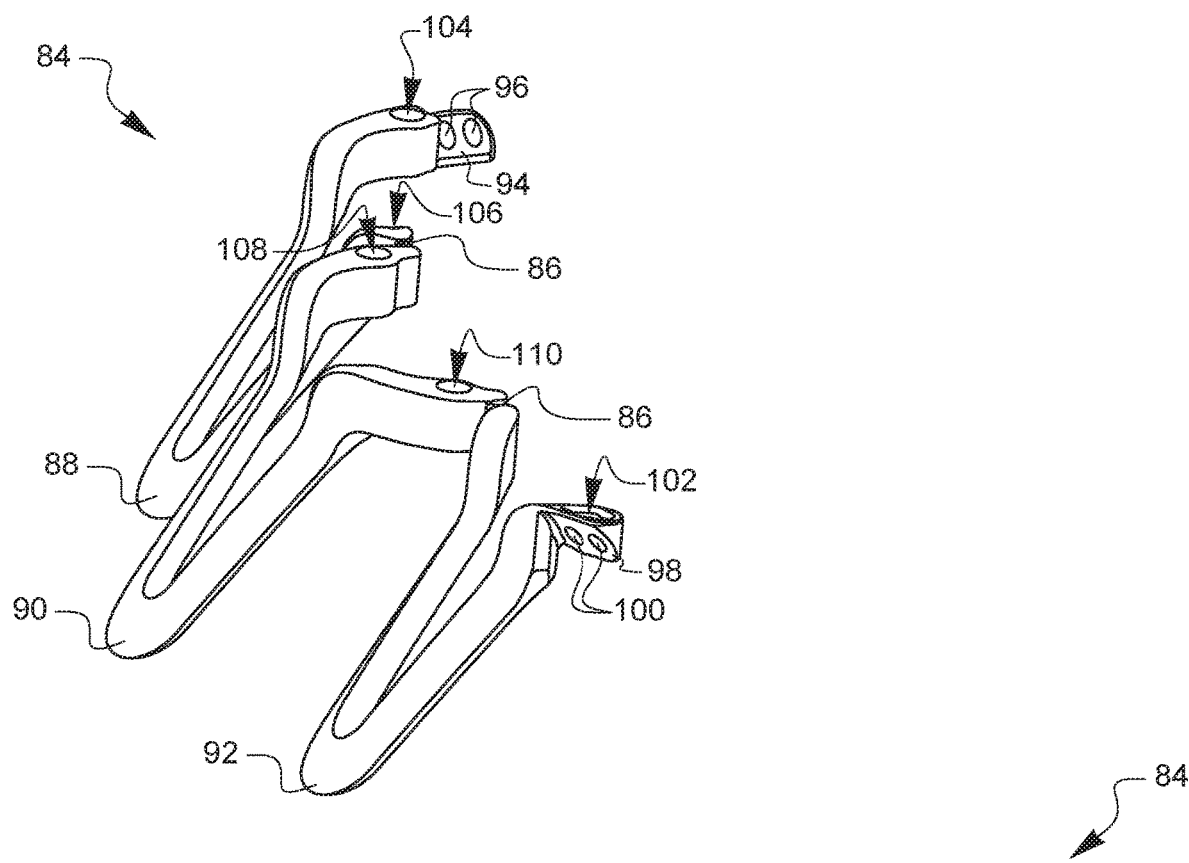
FIGS. 5A-5B are an unfolded proximal-top-right and a folded distal-top-left perspective views, respectively, of an embodiment of an aortic root retractor frame.
Figure 5B:
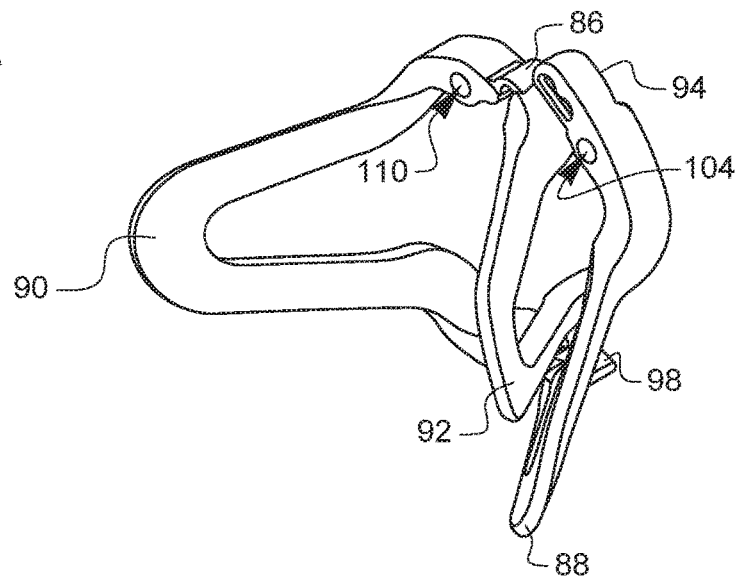

FIGS. 5A-5B are unfolded proximal-top-right and folded distal-top-left perspective views, respectively, of an embodiment of an aortic root retractor frame. FIG. 5A illustrates the ARR frame 84 in an unfolded orientation. The aortic root retractor frame 84 is a continuous article of plastic defining several features configured to fulfill its purpose as a foldable or collapsible frame capable of deploying to an open position wherein the frame provides structure and visibility to an aorta during surgical procedures. The ARR frame 84 defines two living hinges 86 which are configured to reversibly fold the ARR frame 84 from the folded orientation to a deployed orientation, which will be illustrated in FIG. 5B. The ARR frame 84 further defines a first paddle 88, a second paddle 90, and a third paddle 92 configured to hold open and support the walls of an aorta during a surgical procedure. The three paddles 88, 90, 92 are also known as U-paddles due to their shape in this embodiment, although alternate embodiments may have paddles having other shapes or physical arrangements. The ARR frame 84 also defines a first geometric mating feature 94 at one end having two suture guides 96 and an angled surface configured to mate with a second geometric mating feature 98 that also defines an angled surface. The second geometric mating feature 98, which overlaps and mates with the first geometric mating feature 94 when the ARR frame 84 is in a deployed or closed position, also defines two suture guides 100, 101 surrounding either side of a deployment tube orifice 102. Suture guide 101 is configured to receive a pin from an ARR frame delivery device or ARR frame introducer device, which will be described later. Adjacent to the first geometric mating feature 94 is a tube orifice 104 and the first paddle 88. Partially visible is a pin receiving orifice 106, adjacent to the living hinge 86 adjacent to the first paddle 88. Two additional tube orifices 108, 110 are spaced around the ARR frame 84. The tube orifices 104, 108, 110 are configured to hold the suture tubes used for organizing and entraining sutures (not shown in this view) associated with an ARR frame delivery device which will be discussed later. The orientation of these tube orifices 104, 108, 110 and suture guides 96, 100 with respect to the identifying features of the aortic annulus or aortic root will be described later. FIG. 5B illustrates the ARR frame 84 in a folded orientation. The position of the first paddle 88, second paddle 90, and the third paddle 92, as well as the other features of the ARR frame 84 in the folded orientation should be noted. While this embodiment shown in FIGS. 5A and 5B is made from a plastic material, other materials suitable for surgical procedures requiring such a frame, such as stainless steel, other metals, or other plastics, are known to those skilled in the art and may also be used. Other embodiments of an ARR frame may have alternate shapes, consist of multiple segments, or have alternately shaped mating features, tube orifices, or paddles.

Figure 6B:
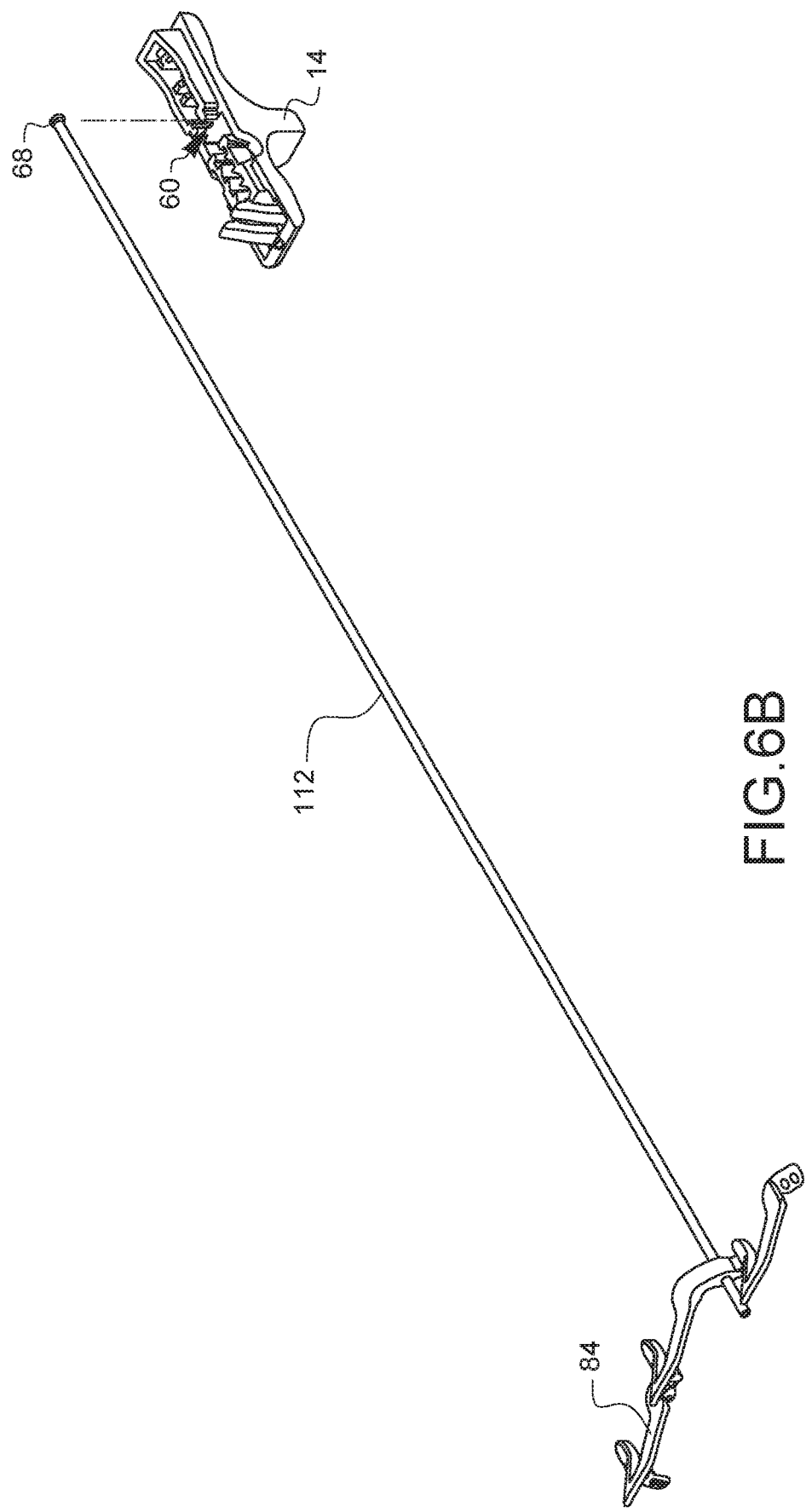

FIGS. 6A-6H, and 6J-6K are a series of exploded views illustrating the assembly of one embodiment of an aortic root retractor which includes the aortic root retractor frame of FIGS. 5A-5B and a plurality of suture locking apparatuses of FIGS. 1A-1B. FIG. 6I was not used to avoid confusion with numeral one. FIG. 6A illustrates a distal end 112D of a suture tube 112 being inserted into one of the tube orifices 110 on the ARR frame 84. On a proximal end 112P of the R-Non suture tube 112 is a flared end 68. This flared end can be molded, thermally formed, or machined according to methods known to those skilled in the art. FIG. 6B shows the insertion of the ARR frame 84 and suture tube 112 into the lower housing 14 of a suture locking apparatus 10 as described in regard to FIG. 3C. The flared end 68 of the suture tube 112 is placed within the tube stop 60 of the lower housing 14. Other embodiments may use an adhesive to fixedly attach the suture tube, alone or in conjunction with the flared end.

Figure 6D:
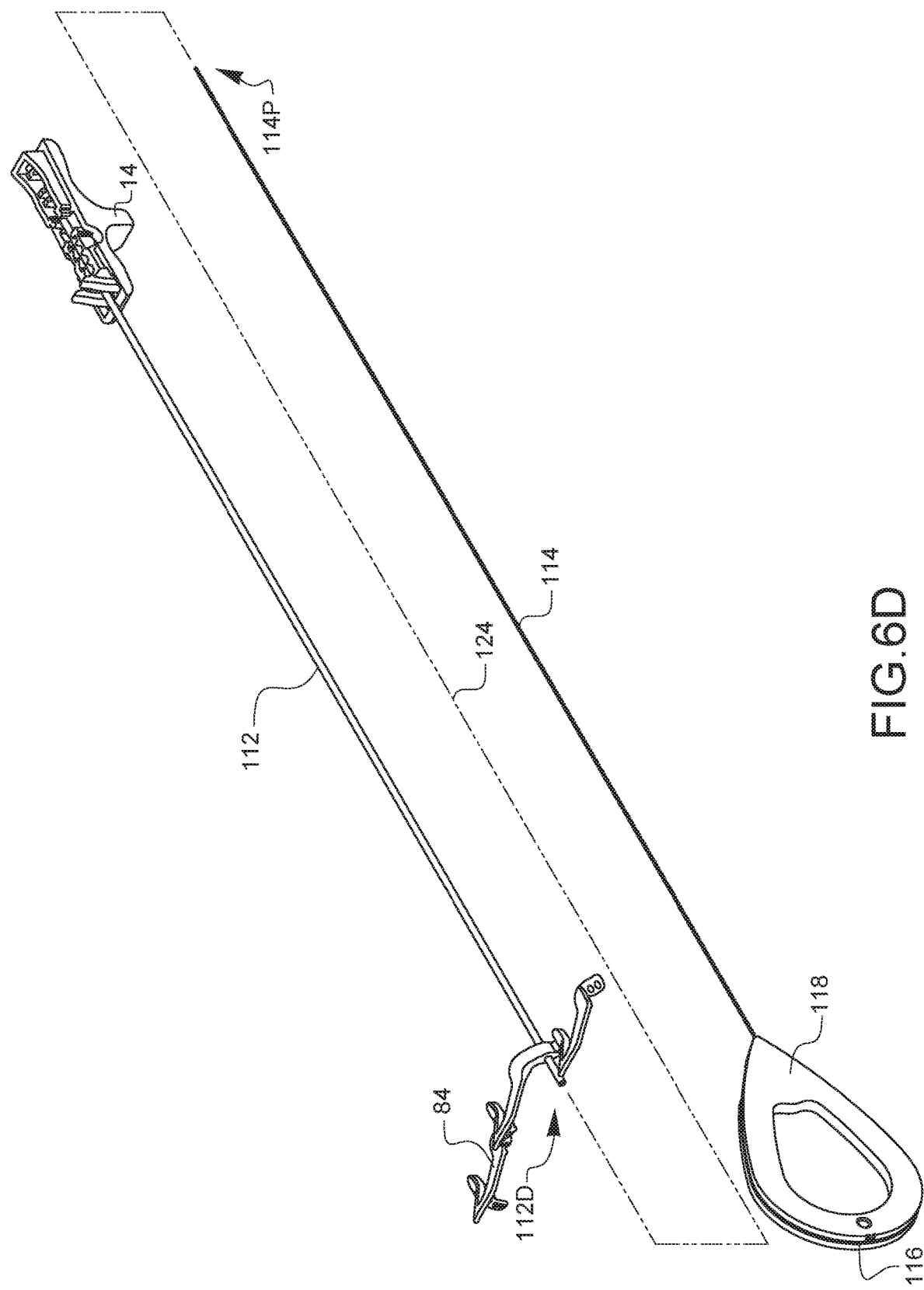

FIG. 6C illustrates another assembly step of the embodiment of the aortic root retractor. A plastic target 118 defining a groove 120 around its perimeter is shown being inserted into a snare loop 116 of a suture snare 114 along axis 122. The target 118 prevents the snare loop 116 from kinking or closing until such time as the snare 114 is utilized in a minimally invasive surgical procedure. Alternate embodiments may be assembled by looping a suture snare around the target, followed by the formation of the snare loop directly onto the target by twisting the snare, adding a knot, or other mechanical fastener. The target 118 can be composed of a plastic, elastomeric, or other material, and may alternatively be color coordinated for visual identification with a particular step of a surgical procedure, which may be advantageous to a surgeon or surgical team. In FIG. 6D, the snare assembly from FIG. 6C is combined with the initial suture tube assembly of FIG. 6B by inserting the proximal end 114P of the snare 114 into the distal end 112D of the suture tube 112 along axis 124.

Figure 6E:
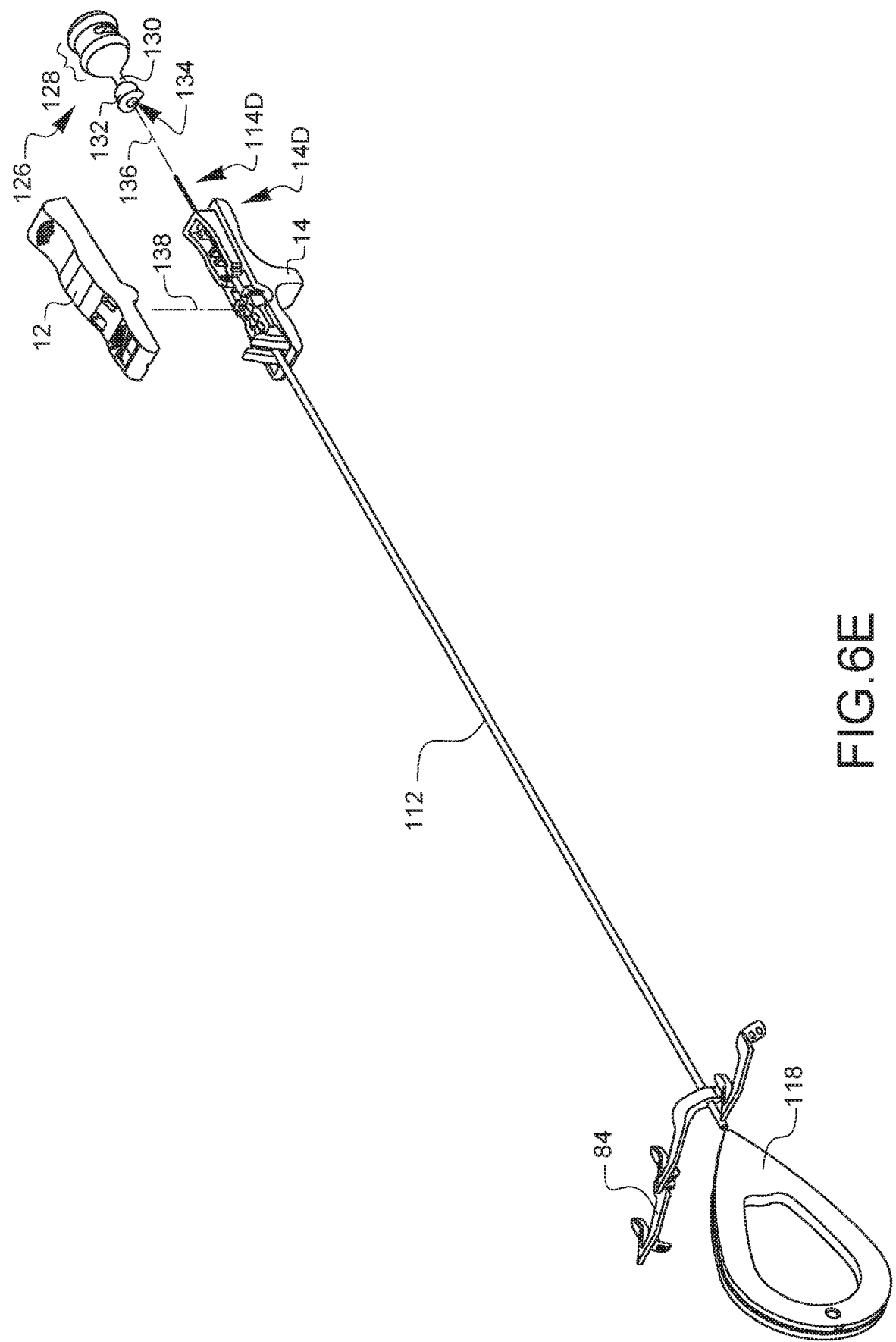

FIG. 6E illustrates the completion of an ARR frame 84 and single suture locking apparatus 10 assembly. An upper housing 12 is snapped onto the lower housing 14 along axis 138, with a distal end 114D of snare 114 protruding from the distal end 14D of the lower housing 14. A chalice 126, also referred to as a metal snare tab defines a handle 128, a neck 130, and a flared end 132 having an opening 134 that travels through the entire length of the chalice 126. The distal end 114D of the snare 114 is inserted into the opening 134 of the R-Non chalice 126 along axis 136 and is fixedly attached to the chalice 126 by crimping the neck 130 and permanently holding the snare 114 within the chalice 126. The snare 114 may also be held in place by other means known to those skilled in the art, such as adhesion or other mechanical fastening methods. The chalice 126 provides several advantages when used in conjunction with a snare 114 and suture locking apparatus 10 such as those described herein. The handle 128 provides a larger, more ergonomic place to grasp and pull a suture snare 114 through a suture tube, while the flared end 132 interfaces with the notch in the distal end of the suture locking apparatus 10 to prevent the suture locking mechanism from being prematurely actuated, for example, before the suture snare and accompanying suture has been pulled through the distal end of the suture locking apparatus. Other alternatives to the chalice 126 may be used, such as hooks, handles, knobs, or other grips. These may be made from metal, plastic or other material of sufficient physical integrity for the intended purpose.

Figure 6F:
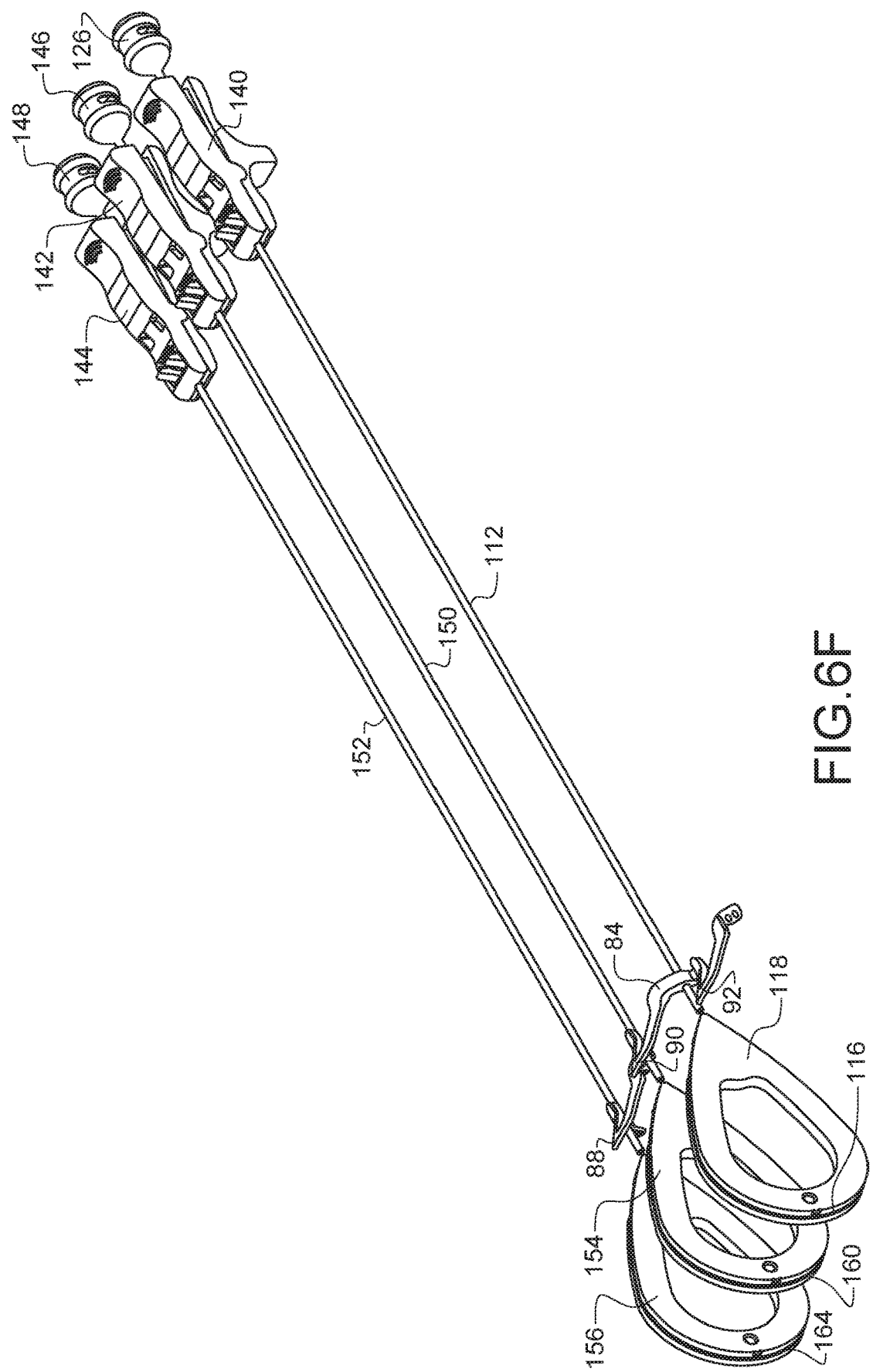

FIG. 6F illustrates a subassembly of the ARR frame 84 and three suture locking apparatuses. The ARR frame 84 is shown in an unfolded orientation as similarly depicted in FIG. 5A. As the ARR frame 84 is designed for use during a minimally invasive surgical procedure for the retraction and stabilization of cardiac tissue, the various elements in the devices and apparatus described herein shall be named in accordance with their associated anatomical structures. While it is possible that the ARR frame could be used in other surgical applications, the used described herein and the associated anatomical naming will be used herein. Further details of the devices and apparatus disclosed herein and how they coordinate with the anatomical features of the cardiac tissue will be discussed in further detail. FIG. 6F shows an R-Non suture locking apparatus 140 having an R-Non chalice 126, R-Non suture tube 112, and an R-Non target 118 inserted within an R-Non snare loop 116 of an R-Non snare 114. Similar structures are shown in regard to the L-Non suture locking apparatus 142, L-Non chalice 146, L-Non suture tube 150, L-Non target 154, and L-Non snare loop 160, as well as the L-R suture locking apparatus 144, L-R chalice 148, L-R suture tube 152, L-R target 156, and L-R snare loop 164 and will be discussed in further detail. The unfolded orientation of the ARR frame 84 and the relative locations of the first paddle 88, second paddle 90, and third paddle 92 are also shown.

Figure 6G:
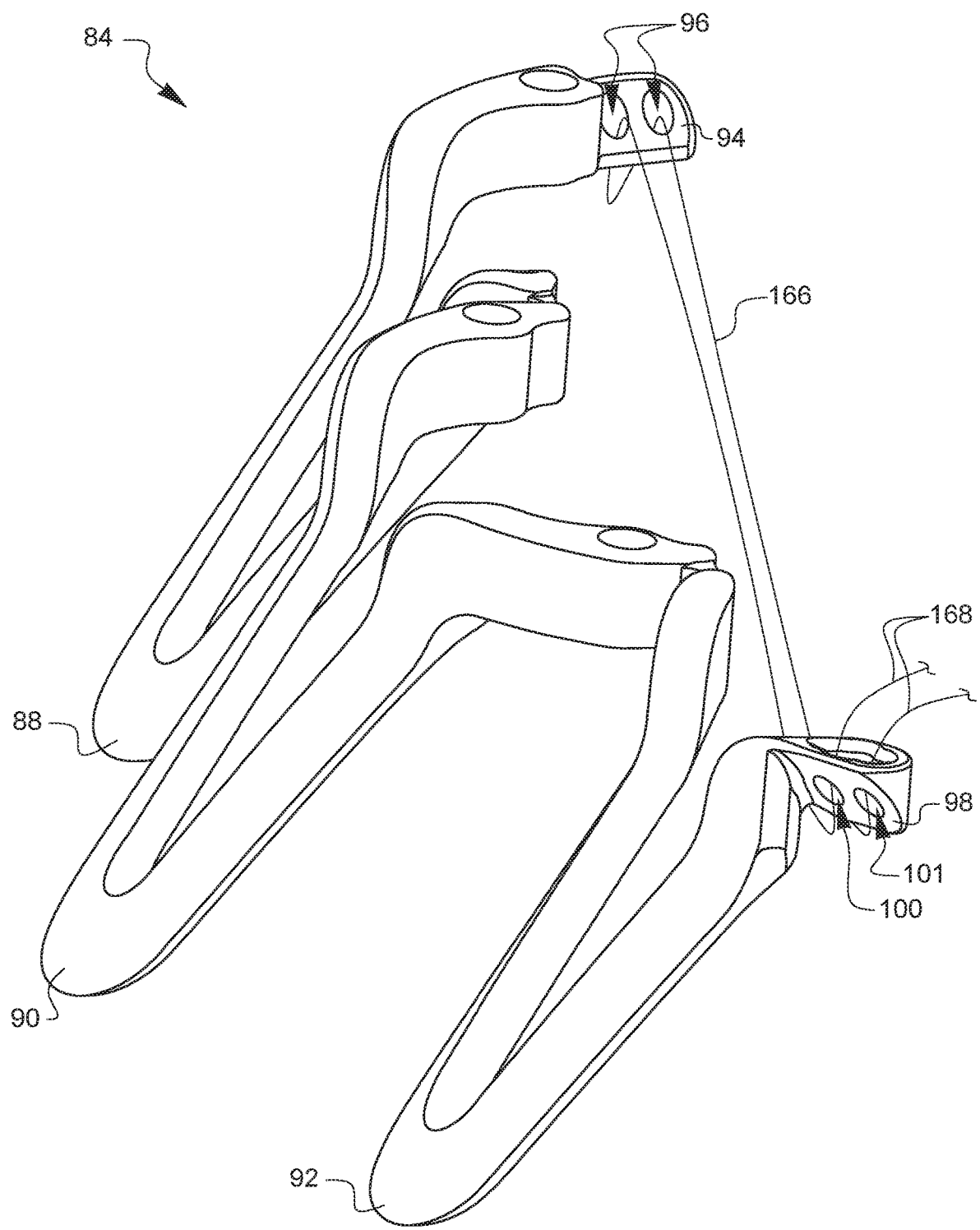

FIG. 6G is a proximal-right-top perspective view of the ARR frame of FIGS. 4A-4B threaded with a deployment suture. In the preceding figures, the various suture tubes 112, 150, 152 have been inserted into the tube orifices 104, 108, 110, but they are removed here for the purposes of illustrating the threading of the deployment suture 166. The deployment suture is threaded into suture guide 100, over to one of the suture guides 96, under the first geometric mating feature 94, out of the other suture guide 96, across the ARR frame 84 and out through suture guide 101. The deployment suture 166 is now threaded in such a manner that when the suture ends 168 are tightened, the first geometric mating feature 94 and second geometric mating feature 98 will be drawn together, their surfaces will mate, and the ARR frame 84 will be configured in a fully deployed state. This deployment mechanism can be activated from outside the body by a surgeon, such as through a cannula and into a minimally invasive surgical site, as one example.

Figure 6H:
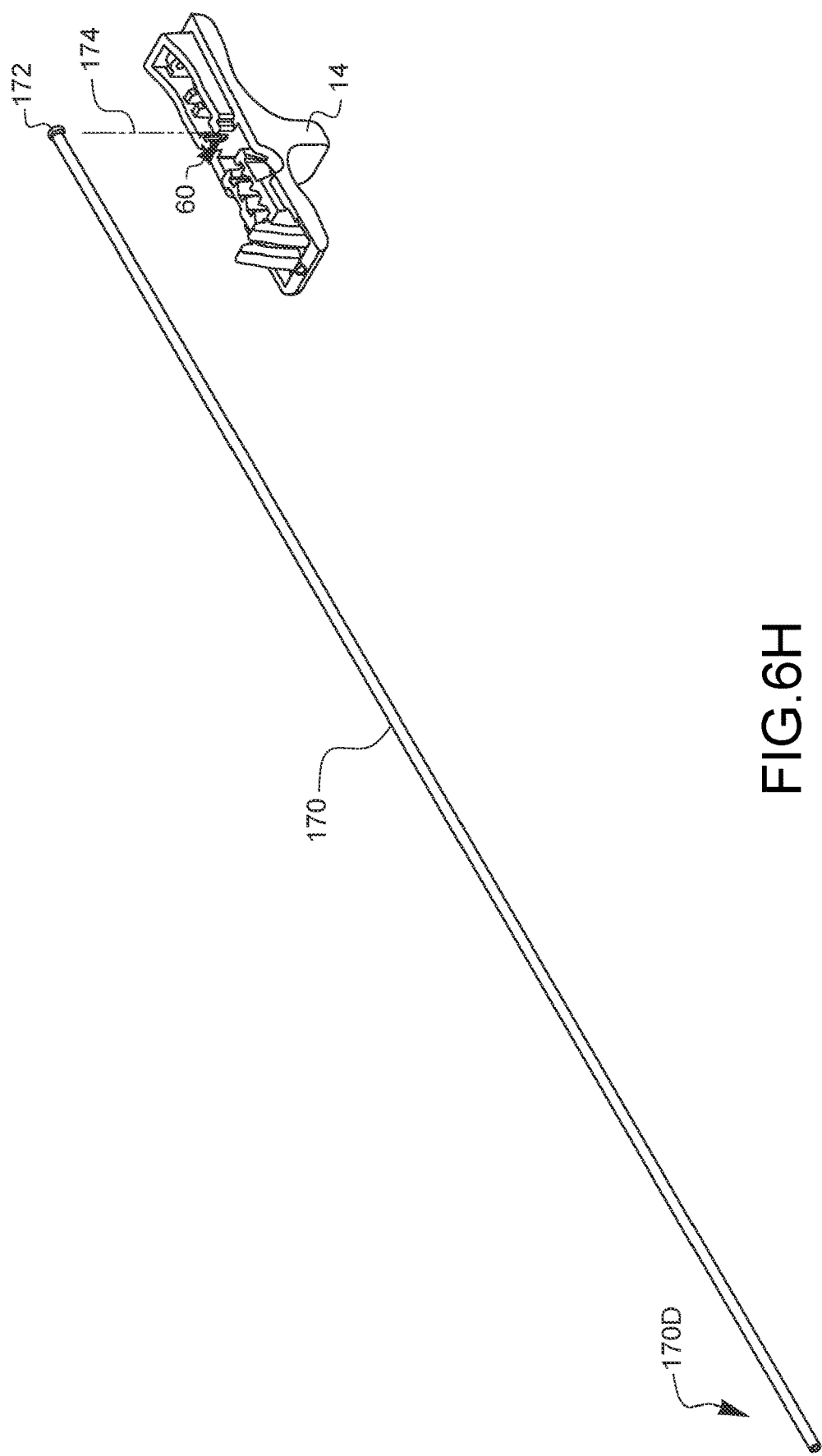
Figure 6J:
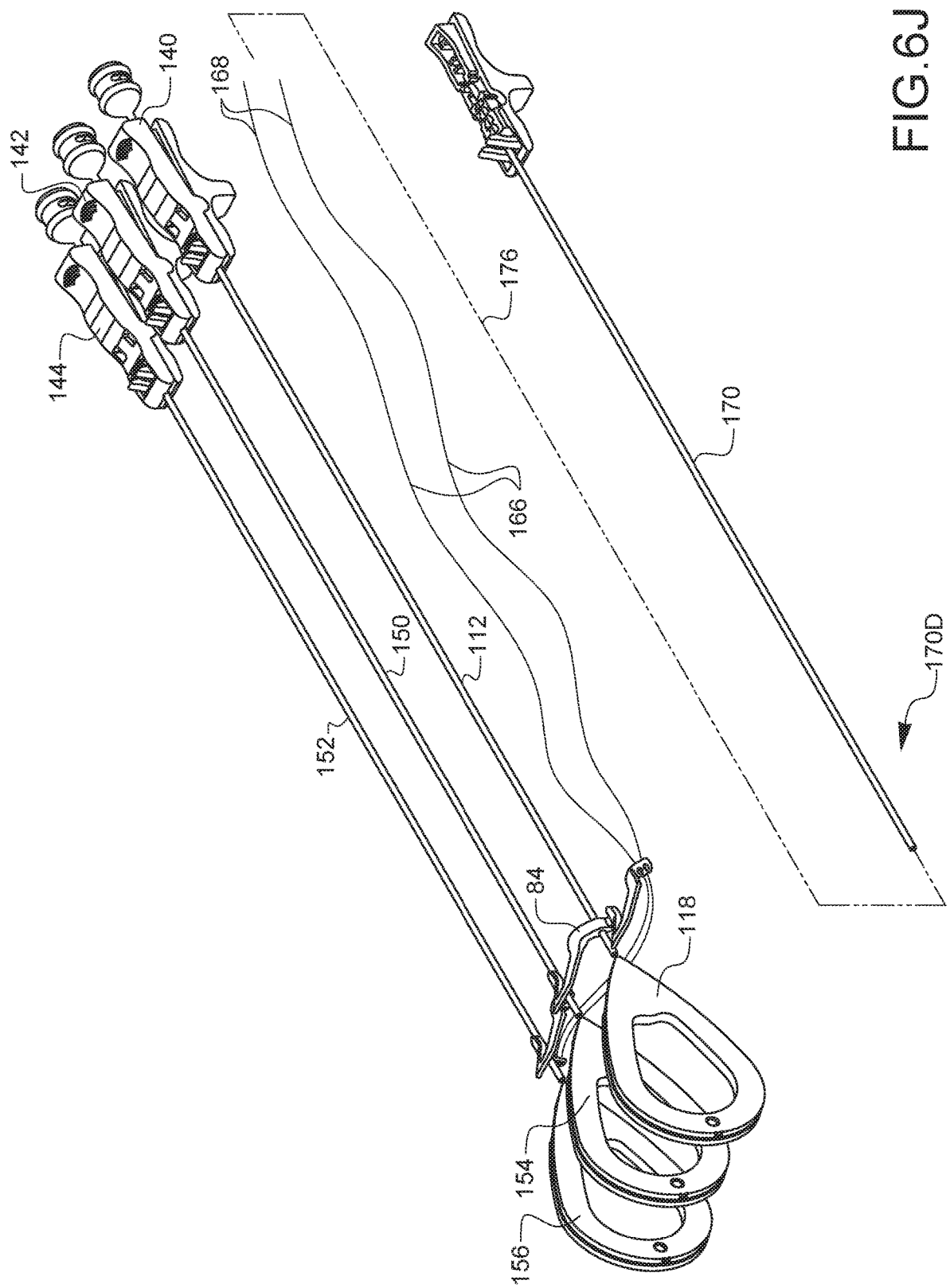

FIG. 6H shows the insertion of a deployment suture tube 170 into the lower housing 14 of a suture locking apparatus 10. The flared end 172 of the deployment suture tube 170 is placed within the tube stop 60 of the lower housing 14 along axis 174. FIG. 6J is an exploded view showing the insertion of the suture ends 168 of the deployment suture 166 into a distal end 170D of the deployment suture tube 170 assembly shown in FIG. 6H along axis 176. The assembled locations of the R-Non suture locking apparatus 140, L-Non suture locking apparatus 142, L-R suture locking apparatus 144, and their respective suture tubes 112, 150, 152, and their respective targets 118, 154, 156 are shown.

FIG. 6K shows an assembly step of the aortic root retractor frame of FIGS. 5A-5B and a plurality of suture locking apparatuses of FIGS. 1A-1B. The suture ends 168 of the deployment suture 166 have been inserted into the deployment suture tube 170 and are now protruding from the distal end 14D of the lower housing 14. An upper housing 12 is snapped onto the lower housing 14 along axis 180. The suture ends 168 of the deployment suture 166 are inserted into the deployment suture chalice 178 and are fixedly attached to the chalice 178 crimping the suture ends 168 with a mechanical fastener 184 along axis 182. The deployment suture 166 may also be held in place by other means known to those skilled in the art, such as adhesion or other mechanical fastening methods. Alternate embodiments similar to those described herein may include alternately shaped pulls, tabs, or chalices than those disclosed.

Figure 7A:
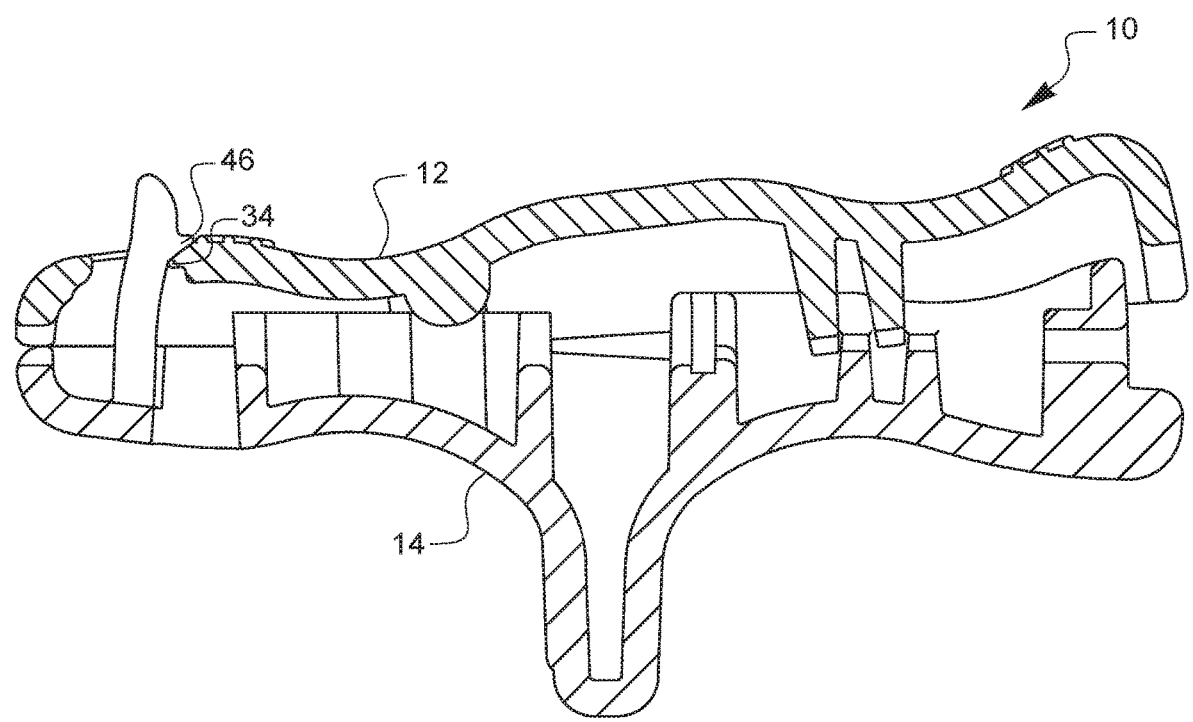
FIG. 7A is a right cross-sectional elevational view of the suture locking apparatus of FIG. 1A in an unlocked position.
Figure 7B:
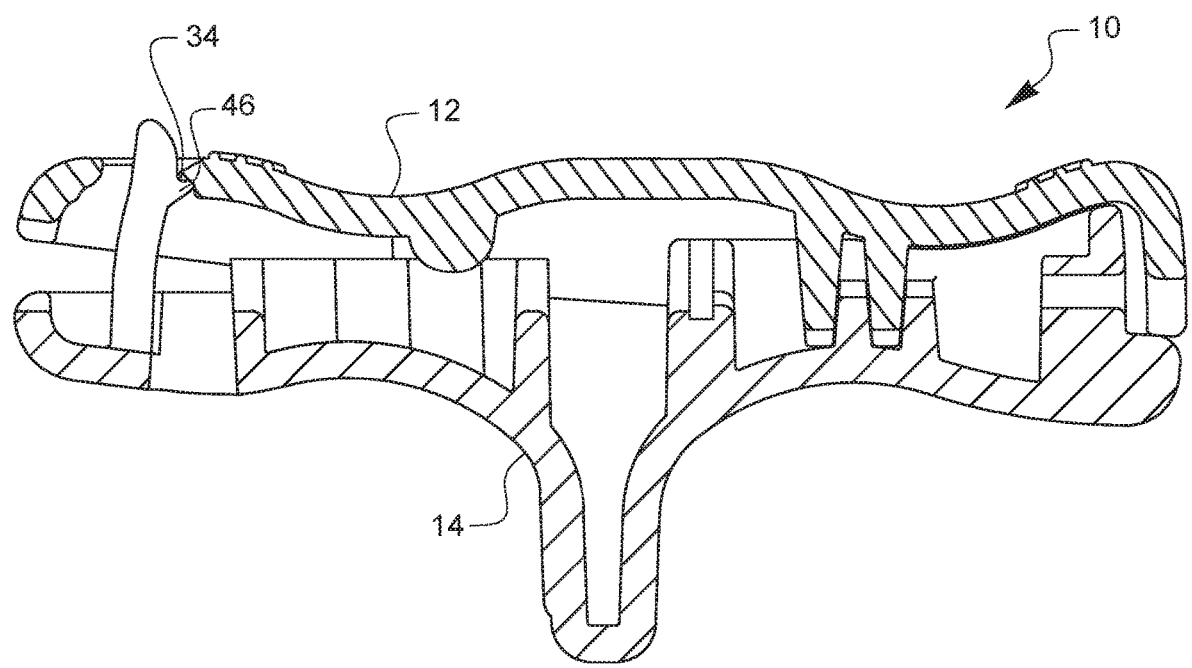
FIG. 7B is a right cross-sectional elevational view of the suture locking apparatus of FIG. 1A in a locked position.

FIG. 7A is a right cross-sectional elevational view of the suture locking apparatus of FIG. 1A in an unlocked position. FIG. 7A is the cross-section previously denoted in FIGS. 2A and 2E. FIG. 7A shows the relative position of the latch step 34 and the latch tab 46 of the suture locking apparatus 10 while in the unlocked position. FIG. 7B is a right cross-sectional elevational view of the suture locking apparatus of FIG. 1A in a locked position. FIG. 7B shows the relative position of the latch step and the latch tab 46 of the suture locking apparatus 10 while in the locked position. The latch tabs 46 need to be pushed away from the latch step 34 so that the latch tabs 46 can clear the latch step 34.

FIGS. 8A-8B are right-side elevational views of a suture locking device which includes the suture locking apparatus of FIG. 1A in an unlocked and locked position, respectively. FIG. 8A is a right-side elevational view of an embodiment of a suture locking device 183 in an unlocked position. In this view, a suture tube 185 is inserted into the distal aperture 24 of the suture locking apparatus 10, and a suture 186 is inserted into and guided through the suture tube 185 through the channel 50, past the tube stop 60, through the lower tooth recesses 44 and exits via the proximal aperture 42. FIG. 8A further shows the upper housing 12 and the lower housing 14 moved pivotably around the hinge 16 such that the distal ends 10D are in closer proximity than the proximal ends 10P of the upper housing 12 and the lower housing 14. In this orientation, the entire suture 186 including the suture ends 188 moves freely within the suture tube 185 while the suture tube 185 is held securely at the tube stop 60 within the suture locking device 183. This unlocked position corresponds to the latch step 34 and latch tab 46 position in FIG. 7A.

FIG. 8B is a right-side view of the suture locking device 183 in a locked position. To engage the locking mechanism, the operator applies a force to the recess 38 at the proximal end 10P of the suture locking apparatus 10. This locked position corresponds to the latch step 34 and latch tab 46 position in FIG. 7B. FIG. 8B further shows the upper housing 12 and the lower housing 14 moved pivotably around the hinge 16 such that the proximal ends 10P are in closer proximity than the distal ends 10D of the upper housing 12 and the lower housing 14. In this orientation, the gripping surfaces of the upper housing 12 and the lower housing 14 are in closer contact, the suture 186 is firmly locked, the suture ends 188 will not move, and any motion is restricted while the suture tube 185 is also held securely at the tube stop 60 within the suture locking device 183 while in either the locked position or the unlocked position. This reversible locking and unlocking mechanism, or releasable locking mechanism can be advantageous if sutures are to be adjusted multiple times during a surgical procedure.

Figure 9:
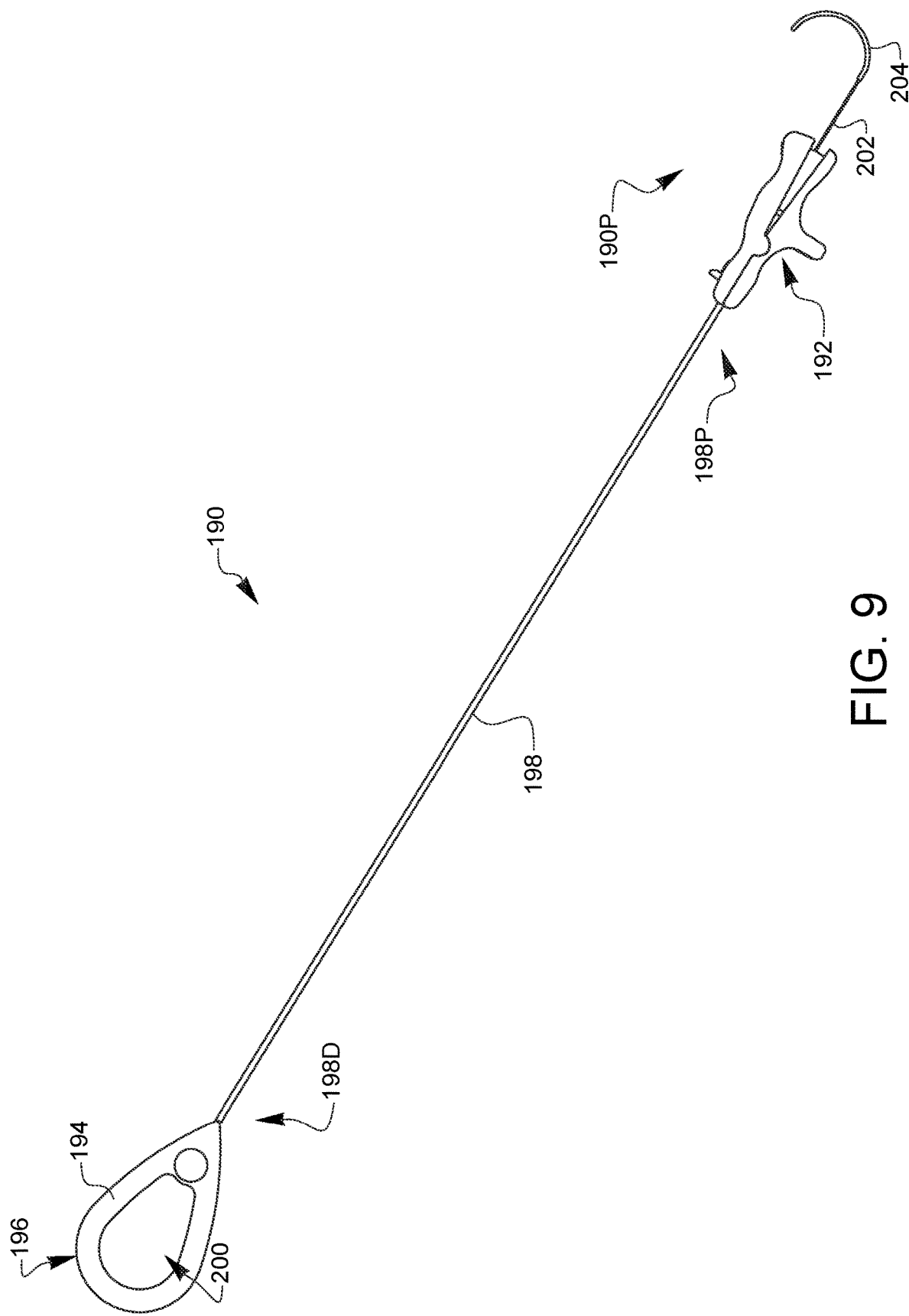
FIG. 9 is a right-side elevational view of a suture management device which includes the suture locking apparatus of FIG. 1A.

FIG. 9 is a right-side elevational view of a suture management device which includes the suture locking apparatus of FIG. 1A. The suture management device 190 can be used in surgical procedures for the temporary management, application and maintenance of tension on sutures. In this embodiment, while the suture locking apparatus 190 is in the unlocked position (as shown), a plastic target 194 can be removed from a wire snare 196 contained at the distal end 198D of a suture tube 198. The snare 196 also runs through the tube 198, passing out of a proximal end 198P, and exiting the suture locking device 190 and culminating in a curved metal handle 212 connected to the proximal end of the snare 202. A chalice or other aforementioned alternatives may be used in place of the metal handle 212. Two ends of a suture (not shown in this view) are passed through a loop 200 in the wire snare 196 at the distal end 192D of the suture management device 190 and the suture is snared and pulled through the suture tube 198 towards the proximal end 190P of the suture management device 190 using the handle 212 to pull. The suture locking apparatus 192 is configured to secure the suture inside the tube 198 when the suture locking apparatus 190 is locked, thereby removing the need for a larger clamp requiring more than one hand or additional assistance to operate. The suture locking apparatus provides an advantage of single-handed operation. While FIG. 9 shows only one embodiment of a suture management device 190 with a suture locking apparatus 192 in use, it is understood that other embodiments and other suture management devices could utilize suture locking devices 192 similar to those described herein. The suture locking apparatuses utilized in a procedure requiring the use of such devices depicted in FIG. 9, could facilitate a more convenient method of locking multiple sutures during a complex, minimally invasive surgical procedure.

Figure 10A:
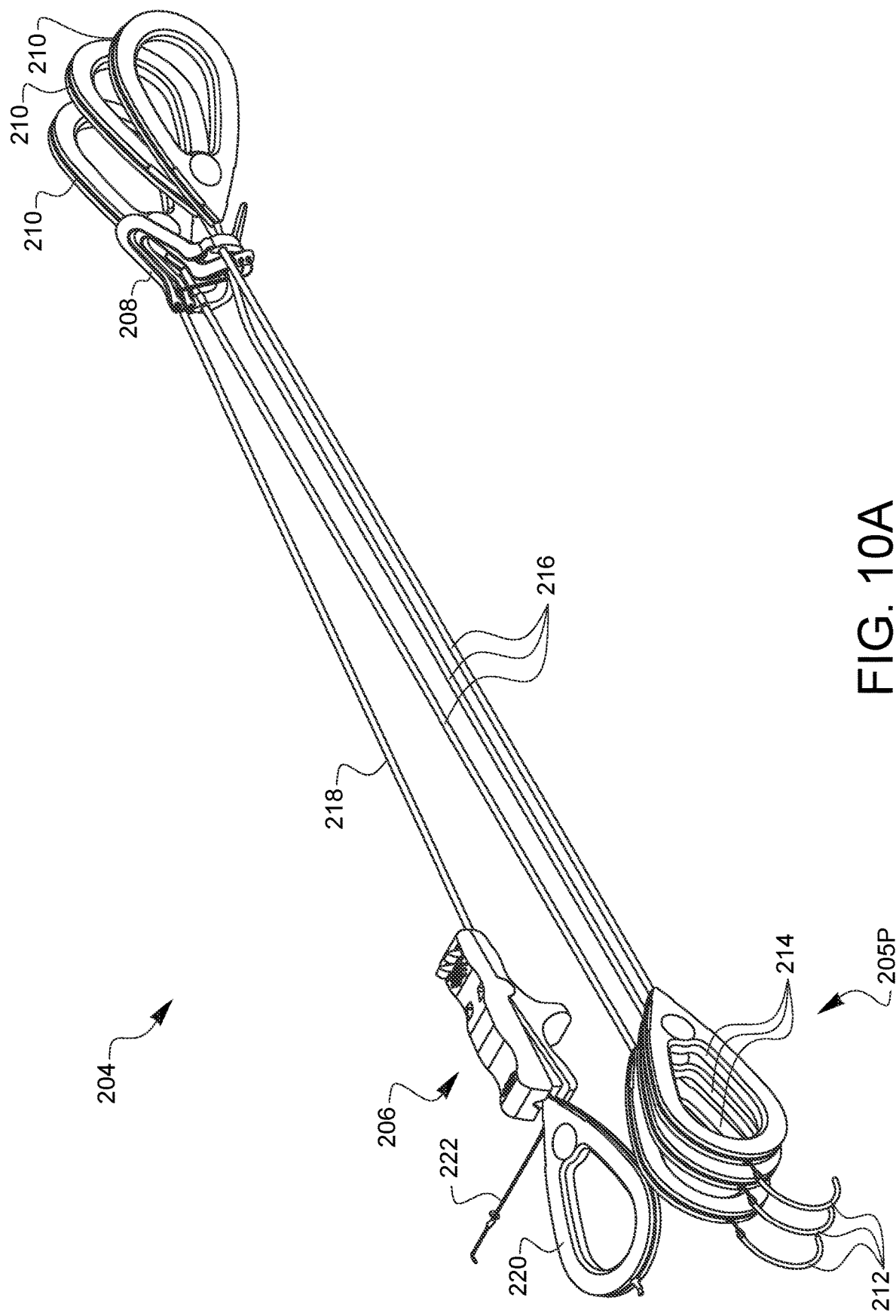
FIG. 10A is a proximal-top-left perspective view of an alternate embodiment of a suture locking apparatus used in combination with the aortic root retractor frame of FIGS. 5A-5B.

FIG. 10A is a proximal-top-left perspective view of an alternate embodiment of a suture locking apparatus used in combination with the aortic root retractor frame of FIGS. 5A-5B. The resulting ARR device 204 is used in minimally invasive surgical procedures for the retraction and stabilization of cardiac tissue during heart valve replacement. The embodiment of the ARR device 204 shown in FIG. 10A includes an ARR frame 208 connected to a suture locking device 206 by a suture tube 218 the suture locking device 206 also includes a deployment suture 222 looped around a target 220. There are also three additional suture tubes 216 inserted into the ARR frame 208 carrying snares, as previously described, with commissural target snare loops 210 on the distal end 204D of the ARR Device 204. On the proximal end 204P of the ARR Device 204, each suture tube 216 has a target 214 inserted into the snare (not shown in this view) with a handle 212 attached thereto. In some embodiments, the target 210, 214, 220 at either end of each commissural suture snare loops may have a unique identifier, such as being color coded for easier visualization and suture management during a procedure. Furthermore, the suture locking device 206 that may be used in place of the targets 214 on one or all of the suture tubes 216 may be color coded as well. The procedure related to the use of the embodiment of the ARR device 204 illustrated in FIGS. 10A and 10B are described in regard to later embodiments.

Figure 10B:
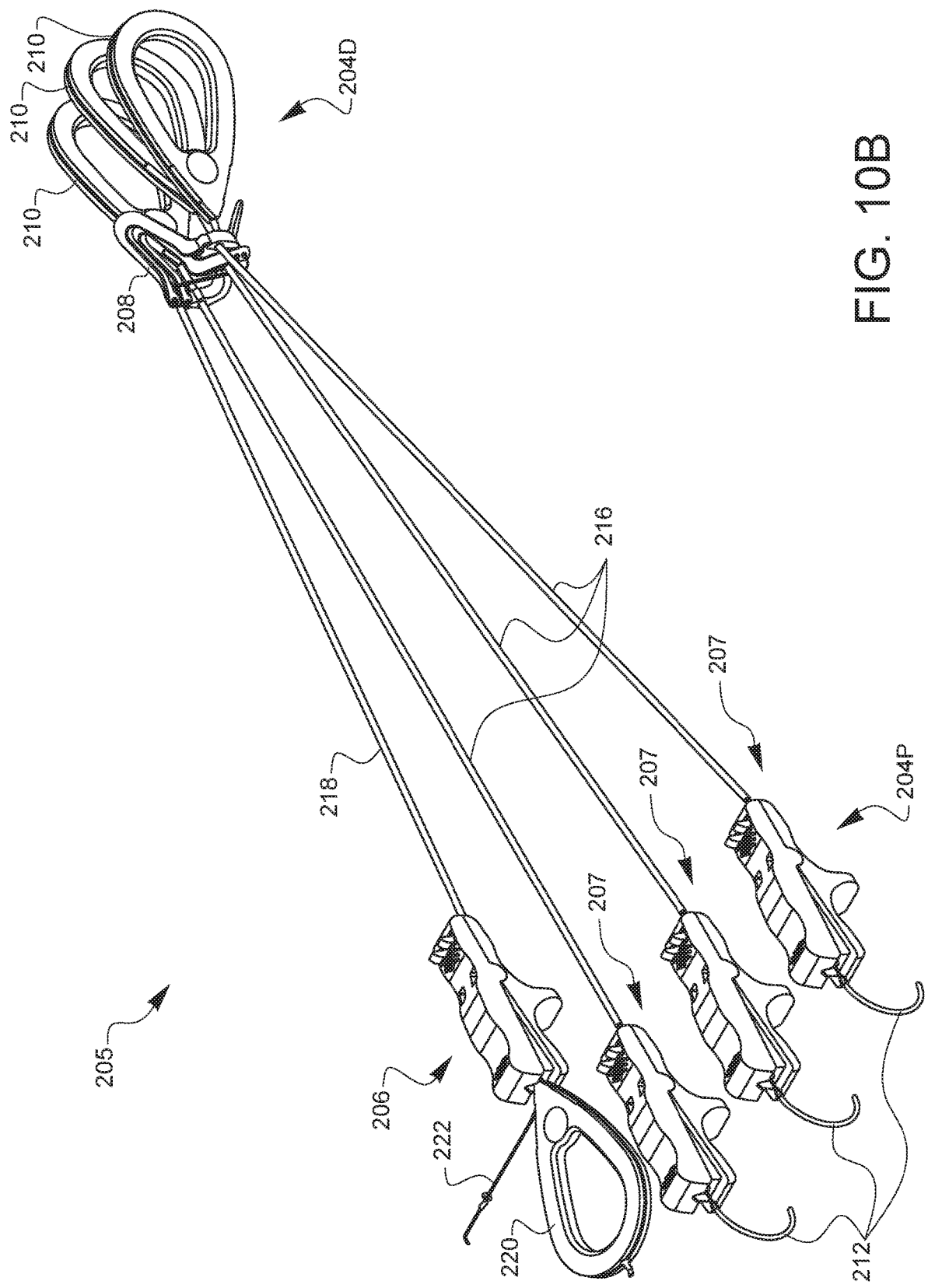
FIG. 10B is a proximal-top-left perspective view of an alternate embodiment of a plurality of suture locking apparatuses used in combination with the aortic root retractor frame of FIGS. 5A-5B.

FIG. 10B is a proximal-top-left perspective view of an alternate embodiment of a plurality of suture locking apparatuses used in combination with the aortic root retractor frame of FIGS. 5A-5B. This embodiment of an ARR device 205 is similar to the ARR device 204 illustrated in FIG. 10A, but also includes additional suture locking apparatuses 207 on the other three suture tubes 216. This embodiment does not include targets 214 at the proximal end 205P of each of the suture locking apparatuses 207 but has several curved handles 212 protruding from the suture locking apparatuses 207.

Figure 11:
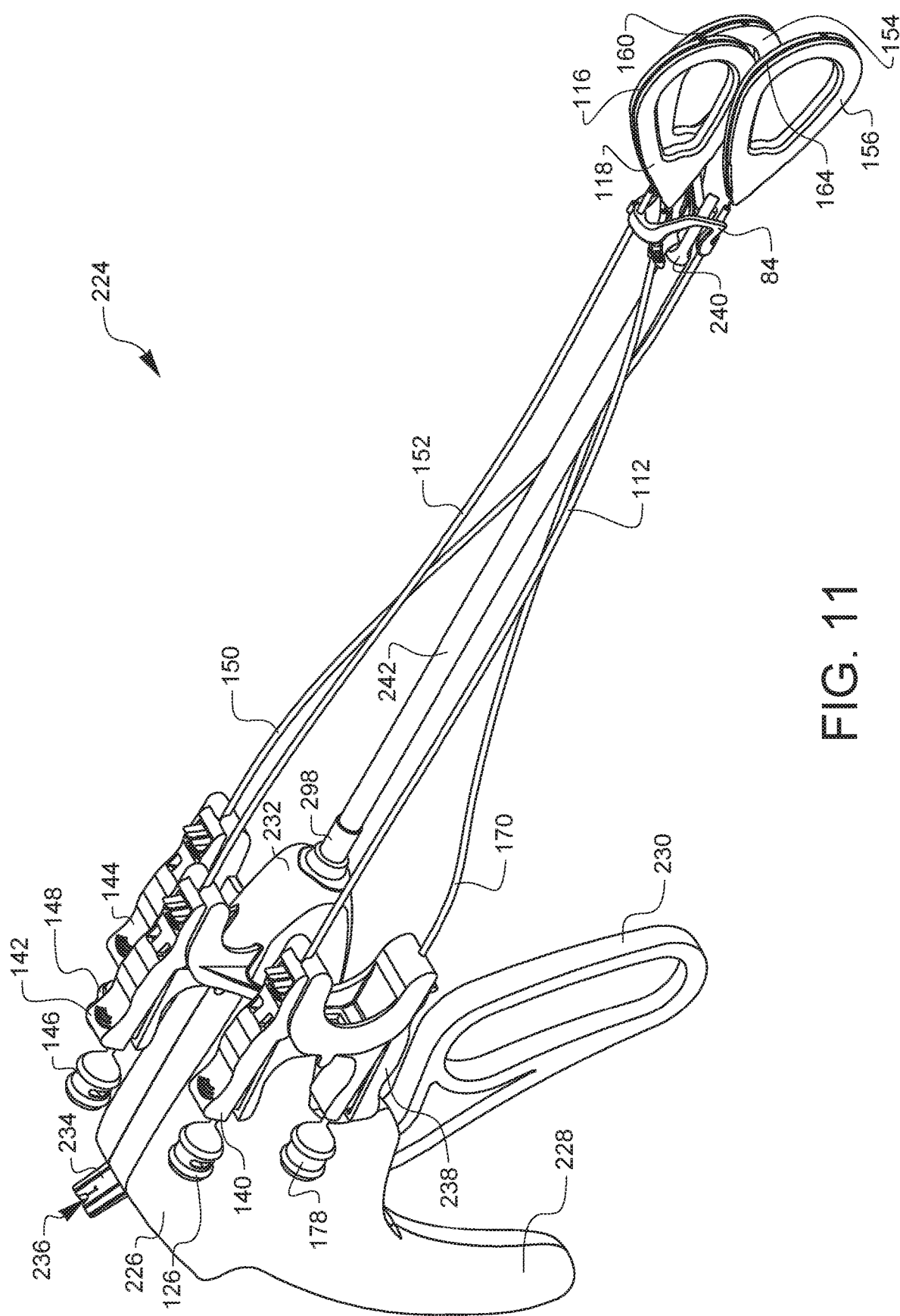
FIG. 11 is a distal-top-left perspective view of one embodiment of an aortic root retractor (ARR) delivery device.

FIG. 11 is a distal-top-left perspective view of one embodiment of an aortic root retractor (ARR) delivery device. The aortic root retractor (ARR) delivery device 224 has a housing 226 with a handle 228, an actuation lever 230. There is a suture lock organizer 232, or chariot at the distal end of the housing 226 configured to releasably hold four suture locking apparatus, the R-Non suture locking apparatus 140, L-Non suture locking apparatus 142, L-R suture locking apparatus 144, and the deployment suture lock apparatus 238. The suture lock apparatuses 140, 142, 144, 238 are each placed in a specific location (in this embodiment, left to right from the point of view of the operator) in the suture lock organizer for the purpose of arranging the suture lock apparatuses suture lock apparatuses 140, 142, 144, 238 on the aortic root retractor (ARR) delivery device 224 according to the order in which they will be utilized in a specific surgical procedure, such as the one described later in regard to FIGS. 15A-15J, 15K-15N, and 15P-15Q. This organization has the advantage of being ergonomically efficient for the operator and has an instructional benefit for teaching surgical procedures or providing a reminder the progress completed in a surgical sequence. Another unique identifier for suture locking apparatuses in this or alternate embodiments of an ARR delivery device may be to have suture locking apparatuses each with a color distinct from one another, which also has a benefit for the operator with regard to ergonomics, instructional value, accuracy, or efficiency. The unique identifier may also be in the form of a unique and distinct text label, image, pattern, or texture on each of the suture locking apparatuses. It could also be in the form of differently sized or shaped suture locking apparatuses. These unique identifiers as listed could also be located or embodied within other elements of an ARR delivery device such as the chalice or snare tab, or on the handle, for example.

A shaft 242 extends from the housing 226 and has an introducer end 240 at the end of the shaft 242. An ARR frame 84, as described in regard to FIGS. 5A-5B, is releasably held in the introducer end 240 or introducer tip. The subassembly completed in FIG. 6K including the R-Non suture locking device 140, R-Non chalice 126, R-Non suture tube 112, R-Non target 118, R-Non snare loop 116, R-Non snare 114, L-Non suture locking apparatus 142, L-Non chalice 146, L-Non suture tube 150, L-Non target 154, L-Non snare loop 160, and L-Non snare (not shown) as well as the L-R suture locking apparatus 144, L-R chalice 148, L-R suture tube 152, L-R target 156, L-R snare loop 164, and L-R snare (not shown) is loaded into the ARR frame introduction device 224. A deployment suture lock apparatus 238 having the deployment suture tube 170 and the deployment suture 166 within are attached to the ARR frame 84 and also loaded into the ARR frame introduction device 224.

Figure 12A:
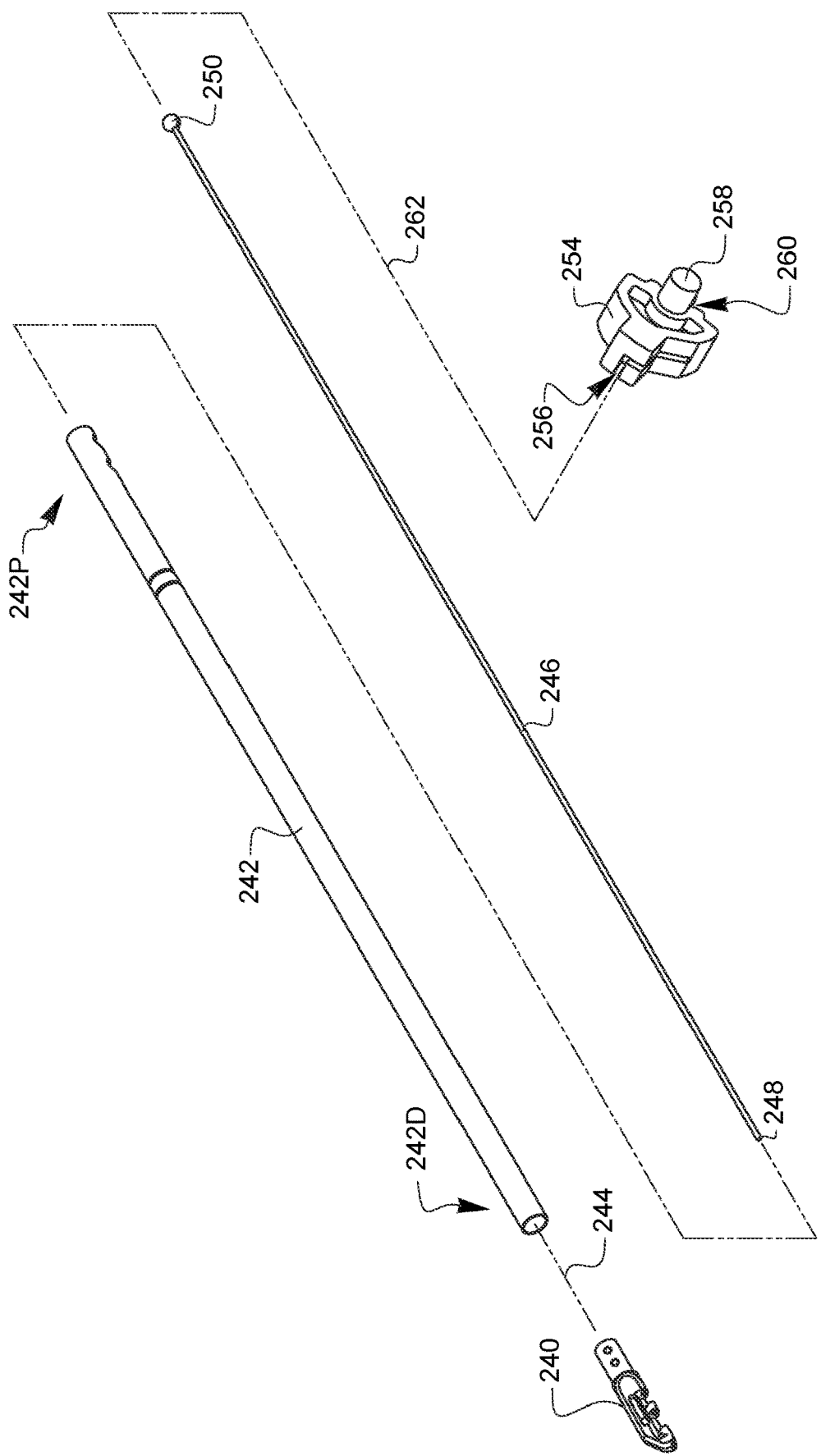
FIGS. 12A-12G are a series of exploded views of various stages of the assembly of the aortic root retractor (ARR) delivery device of FIG. 11 which includes the aortic root retractor of FIG. 6K.

FIGS. 12A-12G are a series of exploded views of various stages of the assembly of the aortic root retractor (ARR) delivery device of FIG. 11 which includes the aortic root retractor of FIG. 6K. FIG. 12A is an assembly step showing the introducer end 240 being inserted along an axis 244 into the distal end 242D of a shaft 242. An introducer pin 246 having a pin tip 248 and a ball end 250 is inserted through the proximal end 242P of the shaft 242 until the pin tip 248 is held within the introducer end 240 through a pin path that travels throughout the length of the introducer end 240. The ball end 250 of the introducer pin 246 is inserted into and held within a ball connector recess 256 of a gear assembly 254 along an axis 262. The gear assembly 254 defines the ball connector recess 256, two axles 258 (one on either side), and a gear 260. The axles 258 on either side of the gear assembly 254 are each configured to interface with a recess in either side of the device housing and allow the gear assembly 254 to pivot when the gear 260 is actuated by the actuator lever 230 (not shown in this view). This pivoting of the gear assembly 254 then moves the introducer pin back and forth along the shaft 242 during operation of the ARR frame introducer device 224.

Figure 12B:
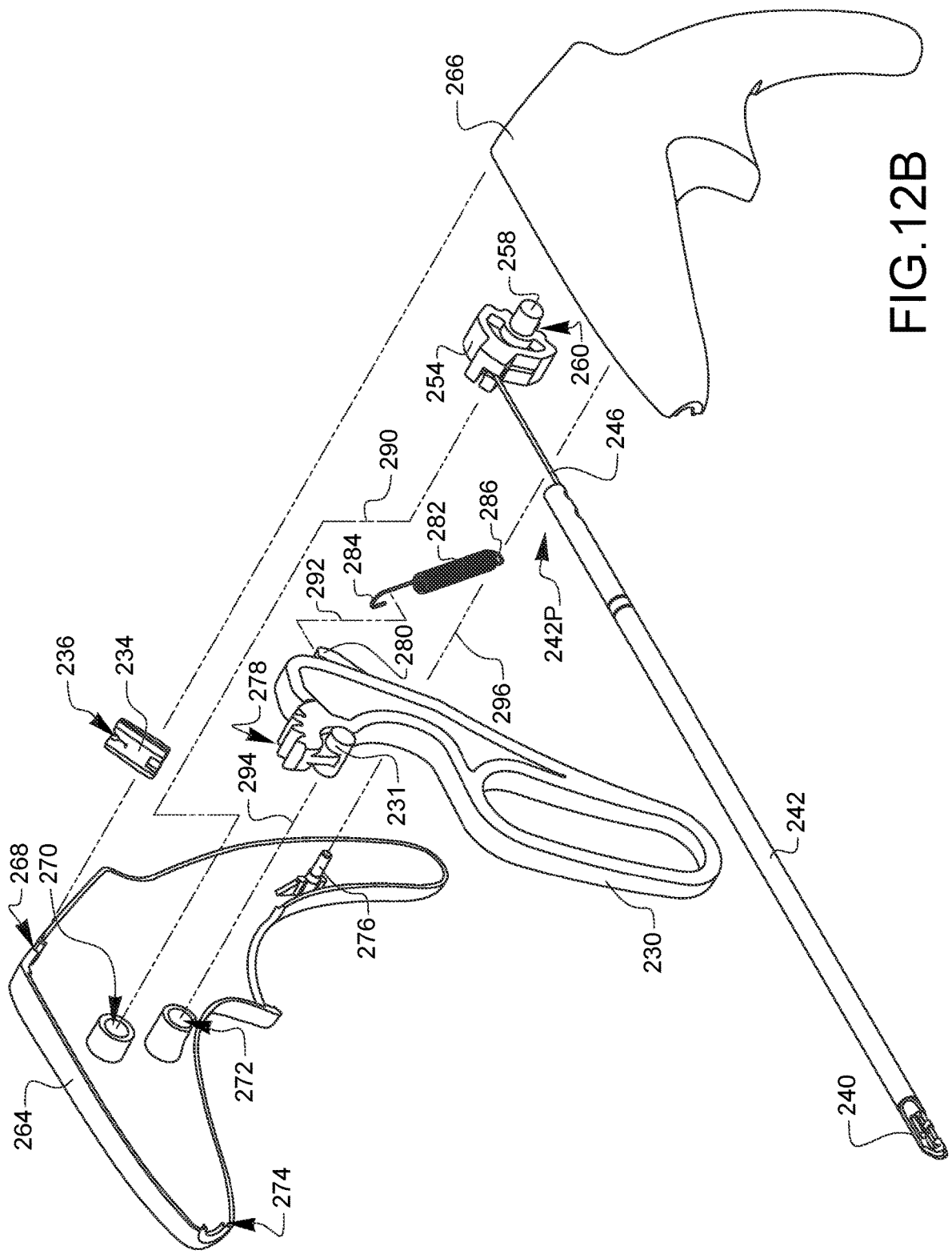

FIG. 12B is an exploded view of a subsequent assembly step of the aortic root retractor frame introduction device 224. A first housing half 264 defines a pivot axle recess 272, a shaft recess 274, a gear recess 270, a tether recess 268, and a spring retainer 276. A tether 234 defining a tether notch 236, configured to releasably hold one or more pair of sutures, is placed in the tether recess 268. An actuation lever 230 is shown in FIG. 12B which has two opposing axles 231 (only one is visible here), a lever gear 278, and a spring attachment 280. One axle 231 on the actuation lever 230 is inserted into the pivot axle recess 272 on the first housing half 264 along an axis 294. A spring 282, having a hook 284 and a loop 286 is attached at the hook 284 onto the spring attachment 280 on the actuation lever 230 along axis 292, and attached at the loop 286 onto the spring retainer 276 on the first housing half 264 along an axis 296. In this arrangement, the spring 282 biases the actuator lever 230 in an unsqueezed, non-actuated position, or a position away from the handle 228 once the assembly is completed.

Still on FIG. 12B, the subassembly of FIG. 12A is placed into a first housing half 264 by inserting an axle 258 of the gear assembly 254 into a gear recess 270 in the first housing half 264 along an axis 290. When the gear assembly 254 is placed into the first housing half 264, the lever gear 278 intermeshes with gear 260 on the gear assembly 254. Next, the second housing half 266 is assembled in place. The second housing half 266 has similar recess features to the first housing half 264 (these features are not shown in this view) to accommodate the respective axles 258, 231 from the gear assembly 254 and actuation lever 230, respectively, as well as a mating feature to align the spring retainer 276 of the first housing half 264 to a corresponding feature in the second housing half 266. The shaft recess 274 of the first housing half 264 also holds the shaft 242 with the corresponding shaft recess (not shown here) on the second housing half 266 when assembled. Optionally, a means of temporarily restricting the lever from being squeezed are known in the art and may be implemented in an aortic root retractor frame introduction device 224 such as those described herein.

Figure 12C:
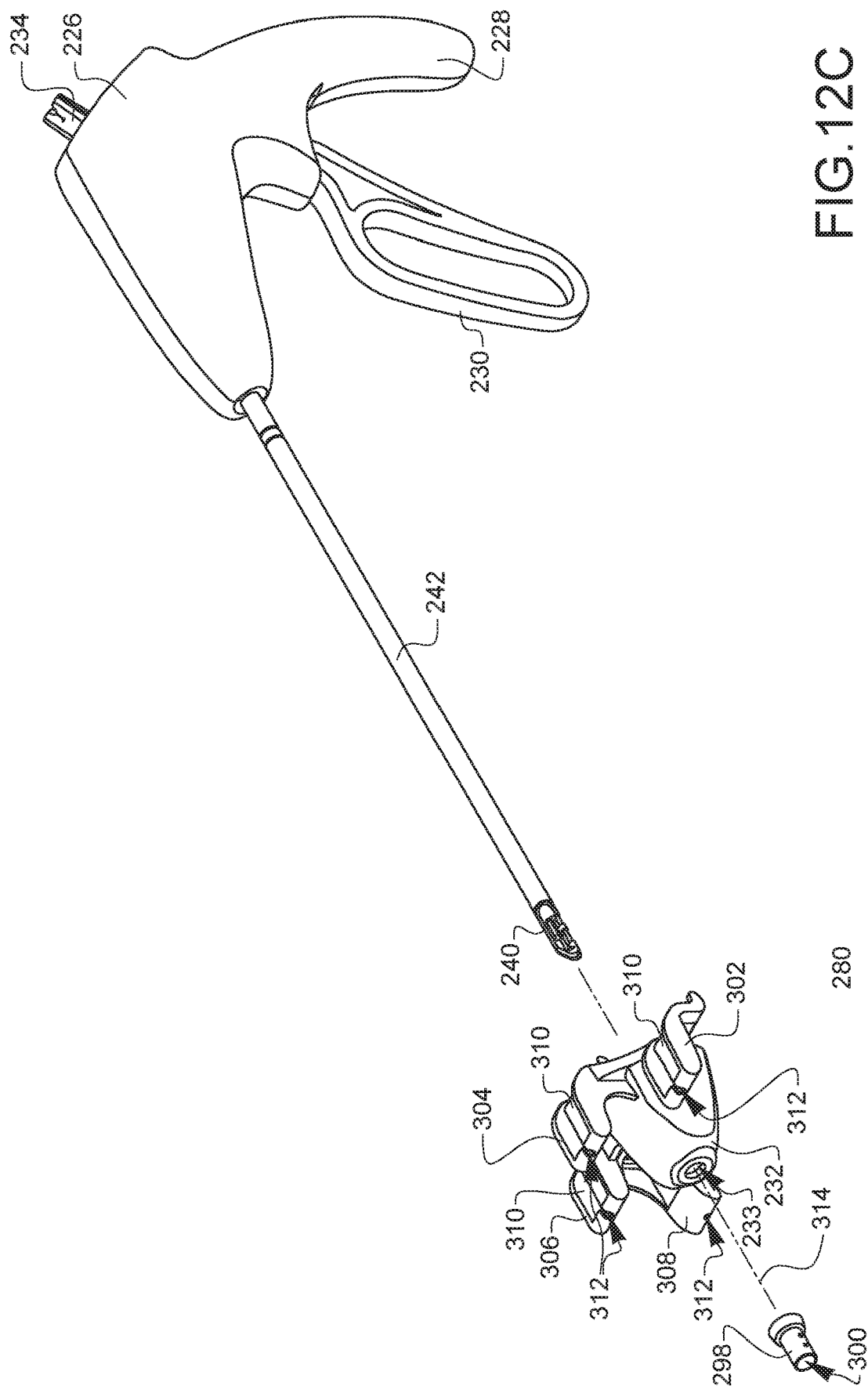

FIG. 12C is an exploded view of an assembly step of the aortic root retractor frame introduction device, or the ARR frame introduction device 224 of FIG. 11. Following the assembly steps in FIG. 12B, the ARR frame introduction device 224 is shown with the completed housing 226 having a handle 228, actuator lever 230, shaft 242, and introducer end 240. A suture lock organizer 232 configured to releasably hold four suture locks has a center hole 233 and four saddles, an L-Non saddle 302, an L-R saddle 304, an R-Non saddle 306, and a deployment saddle 308. Each saddle 302, 304, 306, 308 defining a notch 312 to accommodate and hold a suture tube and is configured to releasably attach a suture locking apparatus 140, 144, 142, 238 into the corresponding L-Non saddle 302, L-R saddle 304, R-Non saddle 306, and deployment saddle 308, respectively. Each saddle 302, 304, 306, 308 also has a recess feature 310 that corresponds to features of the suture locking apparatus 140, 144, 142, 238 and is also configured to hold the suture locking apparatus 140, 144, 142, 238 in each saddle 302, 304, 306, 308. The suture lock organizer 232 is placed over the introducer end 240 and onto the shaft 242 along an axis 314 such that the suture lock organizer 232 is placed directly onto the housing 226. The shaft 242 passes through the center hole 233 of the suture lock organizer 232. A retainer 298 having a center hole 300 is also placed over the shaft 242, the introducer end 240 and shaft 242 passing along axis 314 through the center hole 300 of the retainer 298. The retainer 298 is then fixedly attached to the shaft 242 to effectively fasten the suture lock organizer 232 to the housing 226. Any method of fixing the retainer 298 to the shaft 242, such as screw fastening, brazing, adhering using an adhesive, or other methods known to those skilled in the art may be used. While one arrangement of saddles on a suture lock organizer are shown in this view, it should be noted that other embodiments of suture lock organizers, or similar means of releasably holding multiple suture locks to an aortic root retractor frame introduction device are known to those skilled in the art.

Figure 12D:
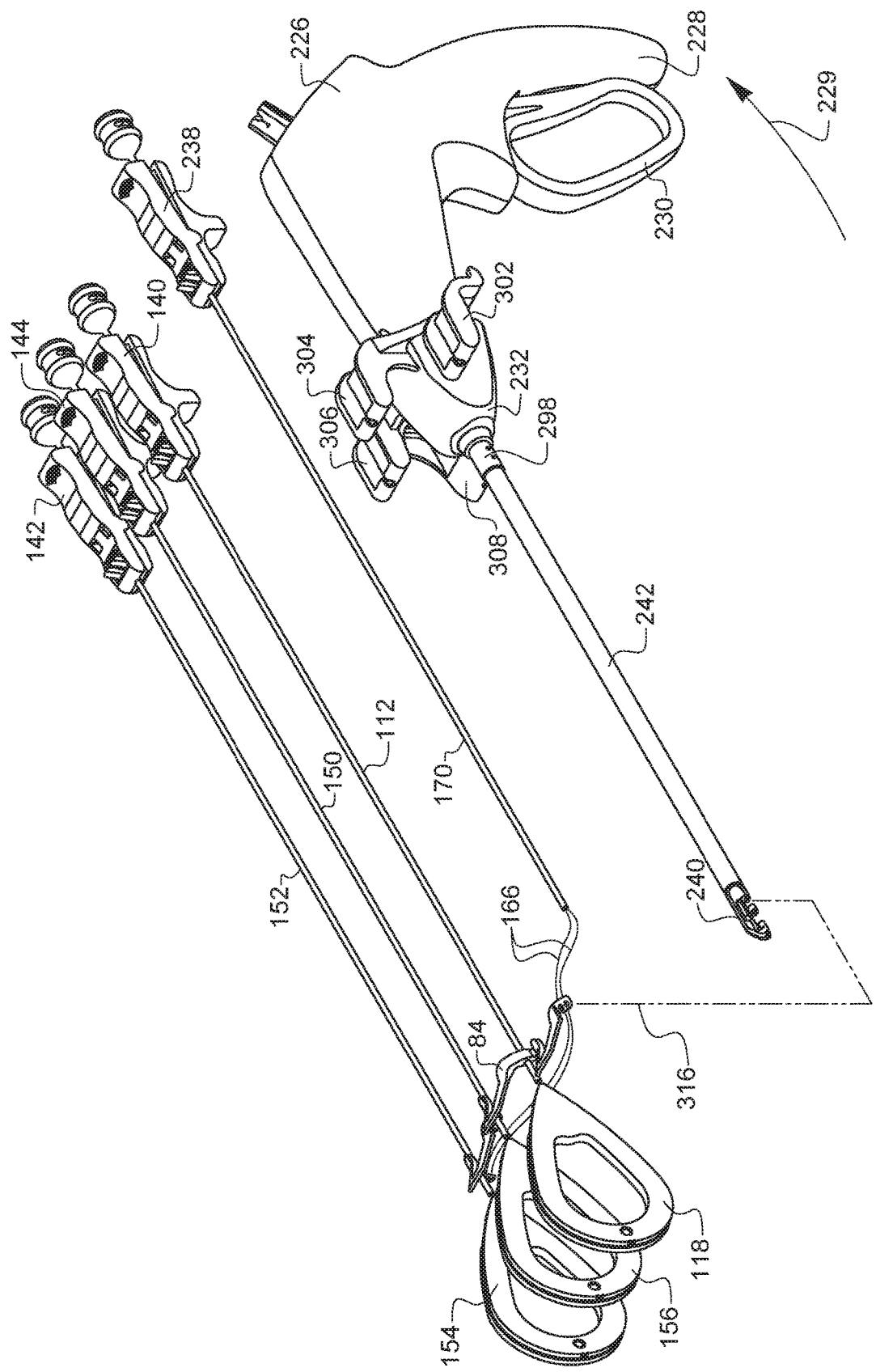
Figure 12E:
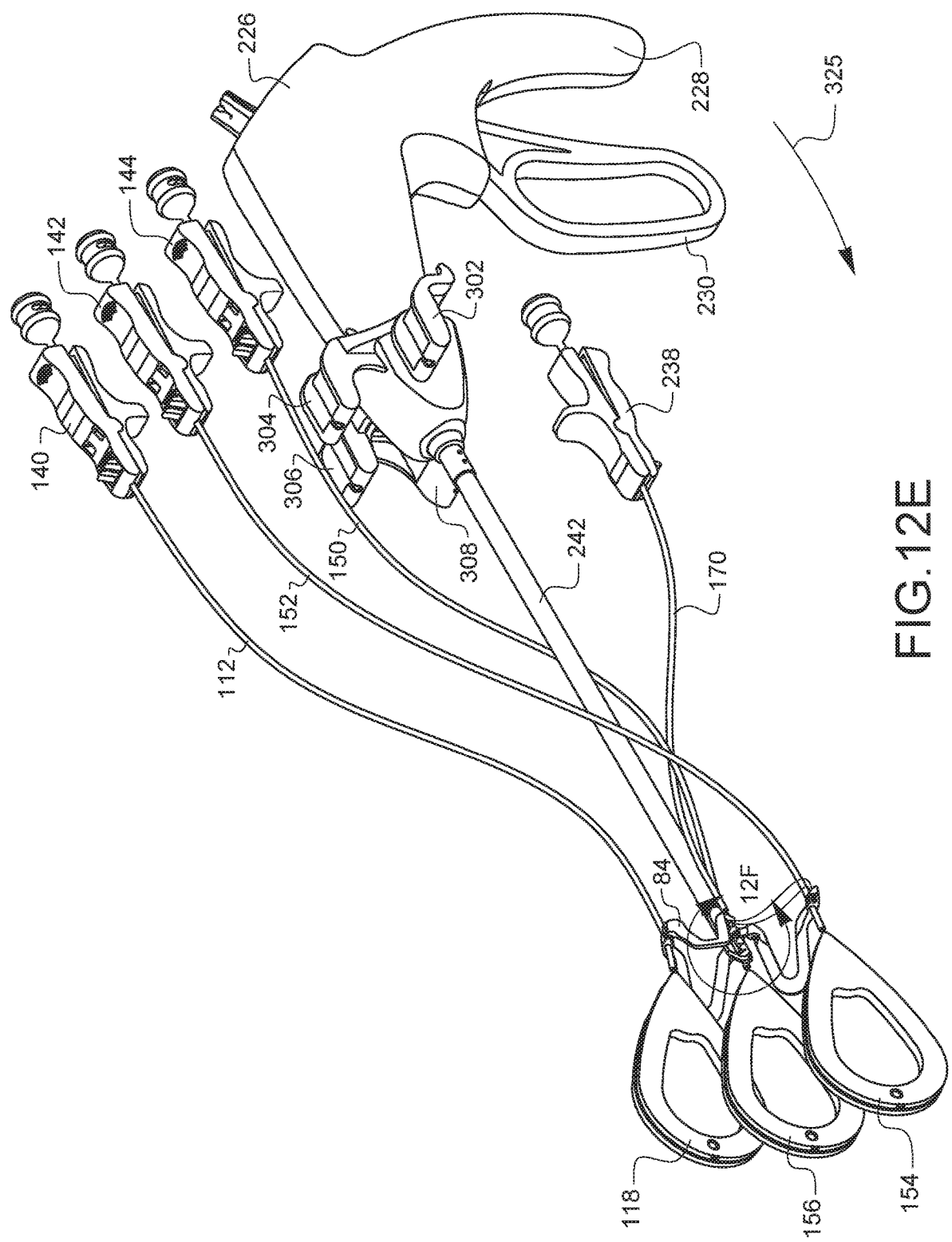
Figure 12F:
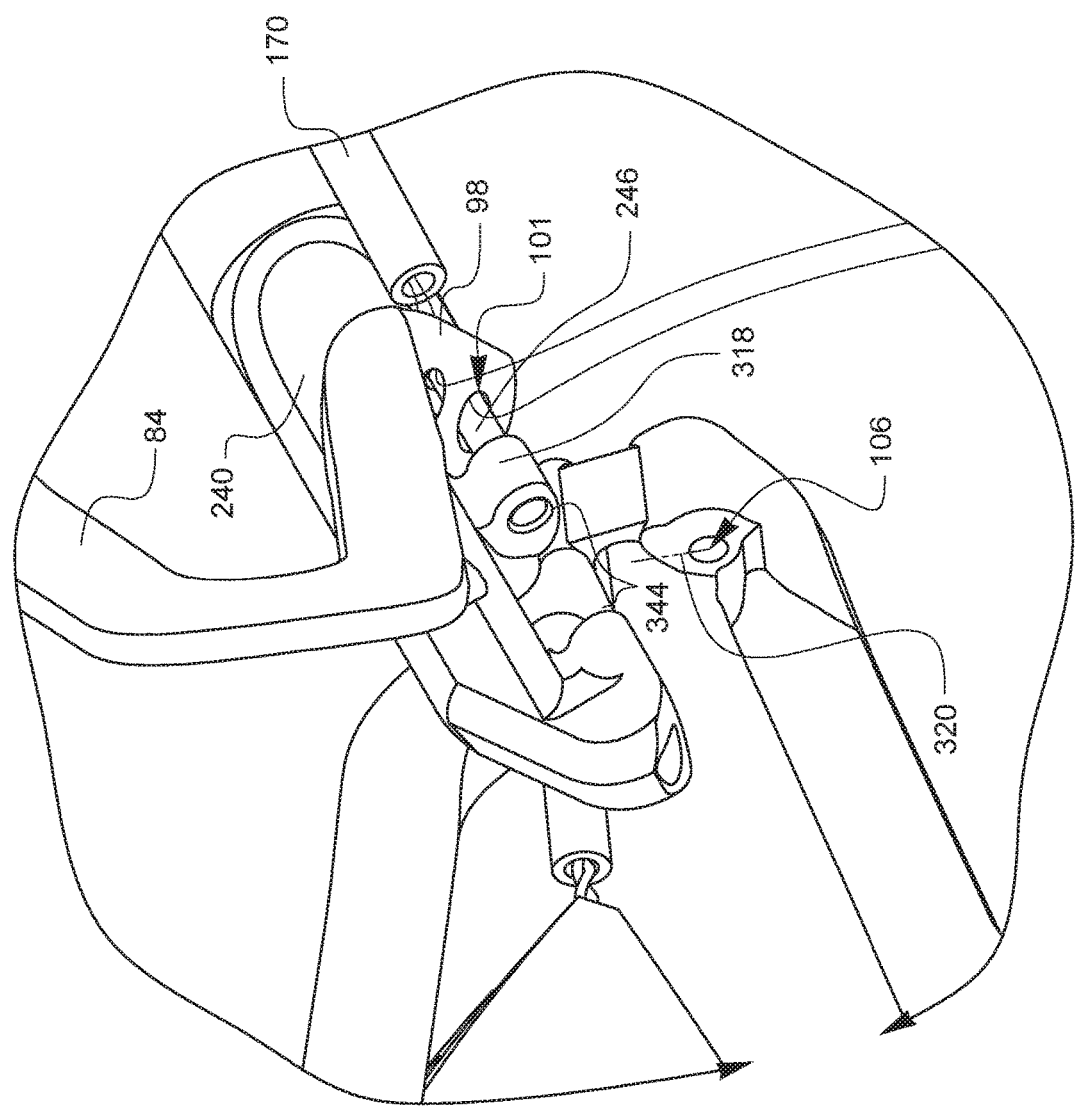

FIG. 12D is an exploded view of an assembly step of the aortic root retractor frame introduction device of FIG. 11. The resulting subassembly of FIG. 6K is now combined with the resulting subassembly of FIG. 12C. The ARR frame 84 is first loaded onto the introducer end 240 along axis 316. The actuation lever 230 is in a squeezed position, with the actuation lever 230 pulled close to the handle 228 in direction 229. This movement of the actuation lever 230 turns the lever gear 278 and the gear 260 of the gear assembly 254, pulling back the introducer pin 246, thus removing it from the introducer end 240. This allows the ARR frame 84 to be placed into the introducer end 240. This will be further detailed in FIGS. 12E and 12F.

FIG. 12 E illustrates an overview of the ARR frame delivery device 224 with the actuation lever 230 partially released away from the handle 228 in direction 325. The R-Non suture locking apparatus 140, L-R suture locking apparatus 144, L-Non suture locking apparatus 142, and the deployment suture locking apparatus 238 with the respective R-Non suture tube 112, L-R suture tube 152, L-Non suture tube 150, and the deployment suture tube 170 are in their assembly orientation. The ARR frame 84, in a folded orientation, is placed into the introducer end 240. FIG. 12F shows the second geometric mating feature 98 of the ARR frame 84 placed into the proximal frame gap 342 (not shown in this view) of the introducer end 240, with the introducer pin 246 partially advanced through suture guide 101 and partially advanced through bridge 318. To fully install the ARR frame 84 into the introducer end 240, the portion of the ARR frame 84 with the pin receiving orifice 106 must be placed into the distal frame gap 344 along axis 320, then the actuation lever 230 is fully released, advancing the introducer pin 246 through the pin receiving orifice 106 and into the pin path 338 towards a blunt tip 334 of the introducer end 240.

Figure 12G:
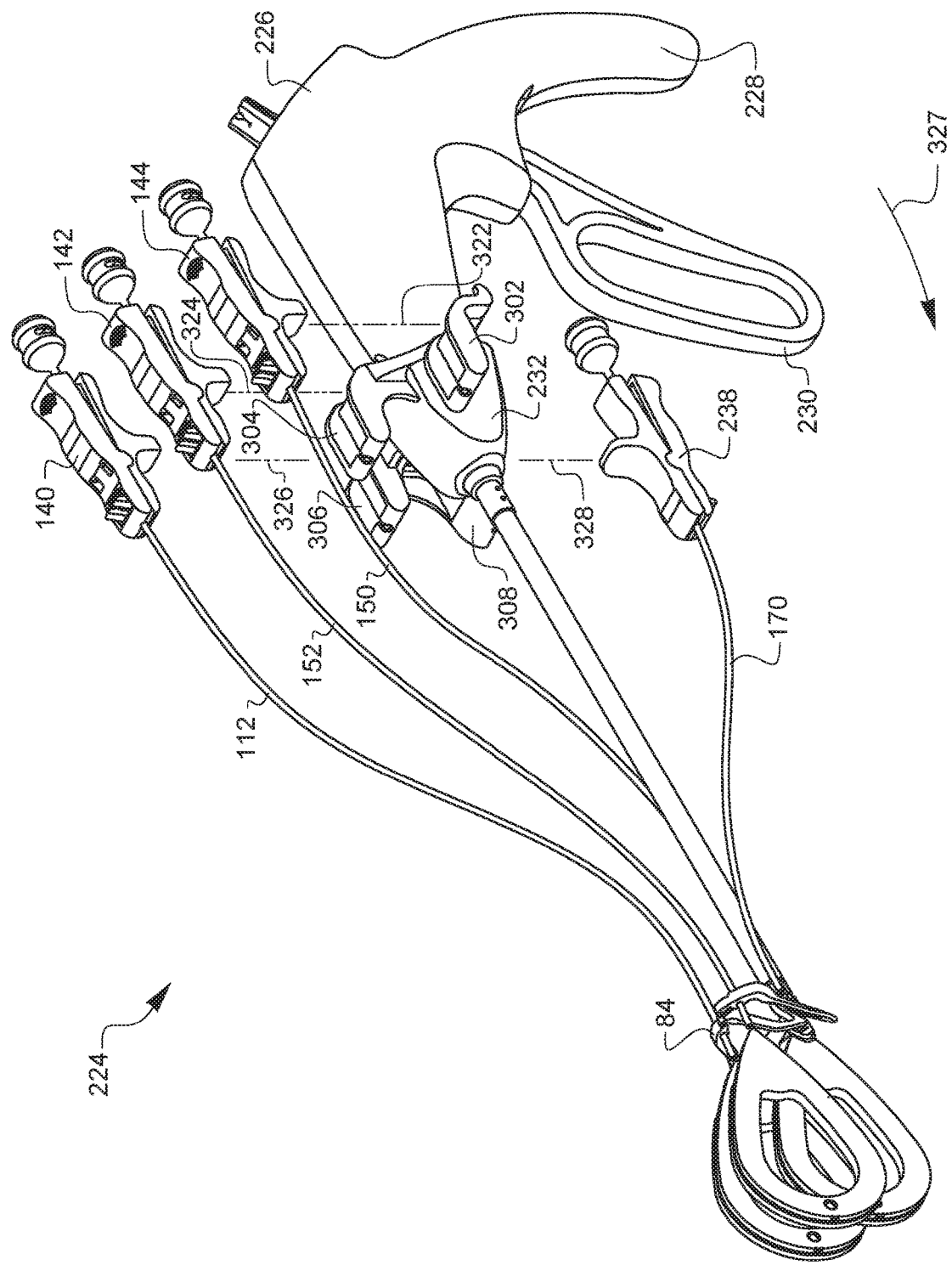

FIG. 12G is an exploded view of a final assembly step of the aortic root retractor frame introduction device of FIG. 11. The ARR frame 84 is shown in a fully folded orientation captured within the introducer end 240 following the assembly steps described in regard to FIGS. 12E-12F, and the actuation lever 230 is shown in a fully released position, having moved in direction 327. In FIG. 12G, the R-Non suture locking apparatus 140 is placed in its saddle 306 along axis 326. In similar fashion, L-R suture locking apparatus 144 is placed in its saddle 304 along axis 324, L-Non suture locking apparatus 142 is placed in its saddle 302 along axis 322, and deployment suture locking apparatus 238 is placed in its saddle 308 along axis 328, completing the assembly of the ARR frame delivery device 224.

FIGS. 13A and 13B are distal-bottom-left and distal-bottom right perspective views of the introducer end of the aortic root retractor (ARR) delivery device of FIG. 11, respectively. The introducer end 240 or introducer tip defines two positioners 332, 333, a blunt tip 334, and an introducer pin path 338 traveling through the body 340 of the introducer end 240. The introducer end 240 further defines a bridge 318 which is a protrusion that further defines a proximal frame gap 342 and a distal frame gap 344. The distal frame gap 344 and proximal frame gap 342 are spaces in the introducer tip 240 to accommodate separate portions of the folded ARR frame 84 before deployment. The introducer pin path 338 accommodates the introducer pin 246 and is configured to guide and allow the introducer pin 246 to freely pass through various channels defined by the introducer end 240 to hold and release the folded ARR frame 84 in various stages of the ARR delivery procedure. These stages of delivery or introduction will be described further in regard to FIGS. 15A-15J, 15K-15N, and 15P-15Q. The blunt tip 334 of the introducer end 240 is rounded or blunt and configured to reduce the potential of tissue trauma when using the aortic root retractor frame introduction device 224. Each positioner 332, 333 is configured to help position the ARR frame 84 in to its final position before deployment during a surgical procedure. The introducer end 240 is connected to the shaft of the device during assembly by screws, welding, adhesion, or other means known to those skilled in the art.

Figure 14:
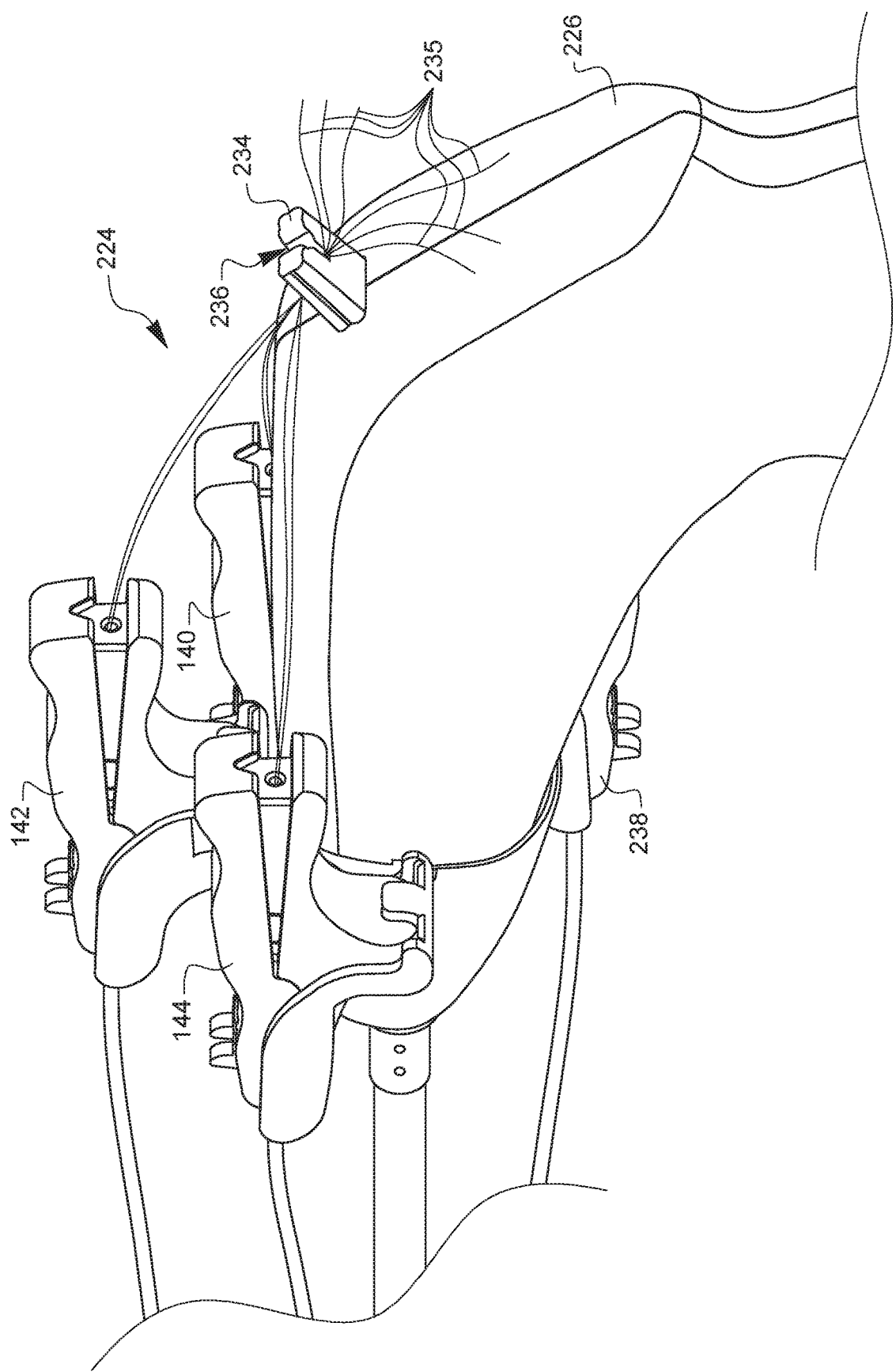
FIG. 14 is a proximal-top-right perspective view of part of the aortic root retractor (ARR) delivery device of FIG. 11 illustrating the use of the suture tether.

FIG. 14 is a proximal-top-right perspective view of part of the aortic root retractor (ARR) delivery device of FIG. 11 illustrating the use of the suture tether. This view depicts the use of the tether 234 mounted to the housing 226 when multiple suture ends 235 are pulled through and locked within each of the suture locking devices 140, 142, 144. The suture ends are releasably held within the tether notch 236 of the tether 234 by a friction fit. If the lengths or the tautness of one or more of the suture ends are adjusted during a minimally invasive surgical procedure using the ARR frame delivery device 224, the suture ends 235 can be easily removed from the tether 234, adjusted and reinserted into the tether notch 236 to be held once more.

Figure 15A:
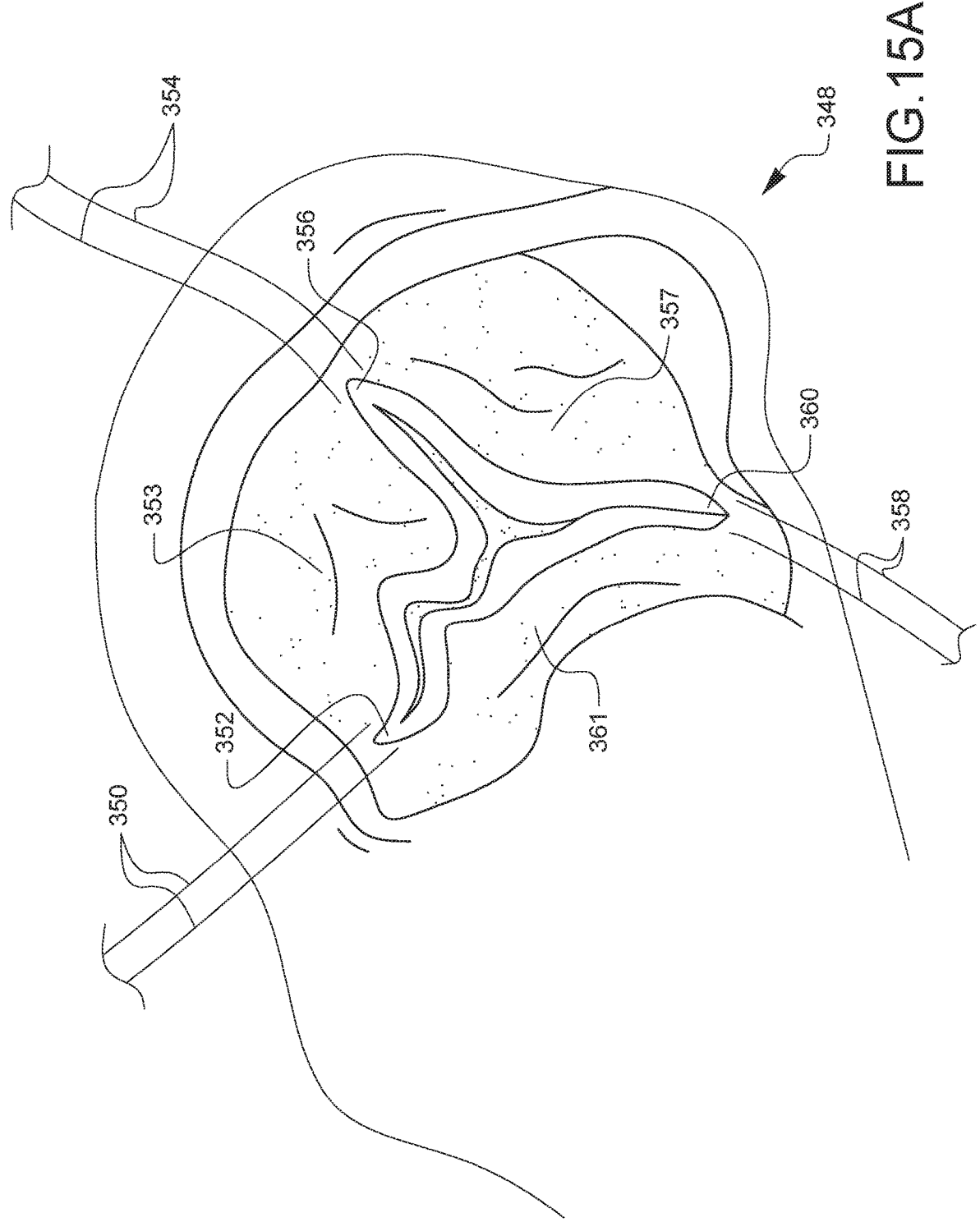
Figure 15B:
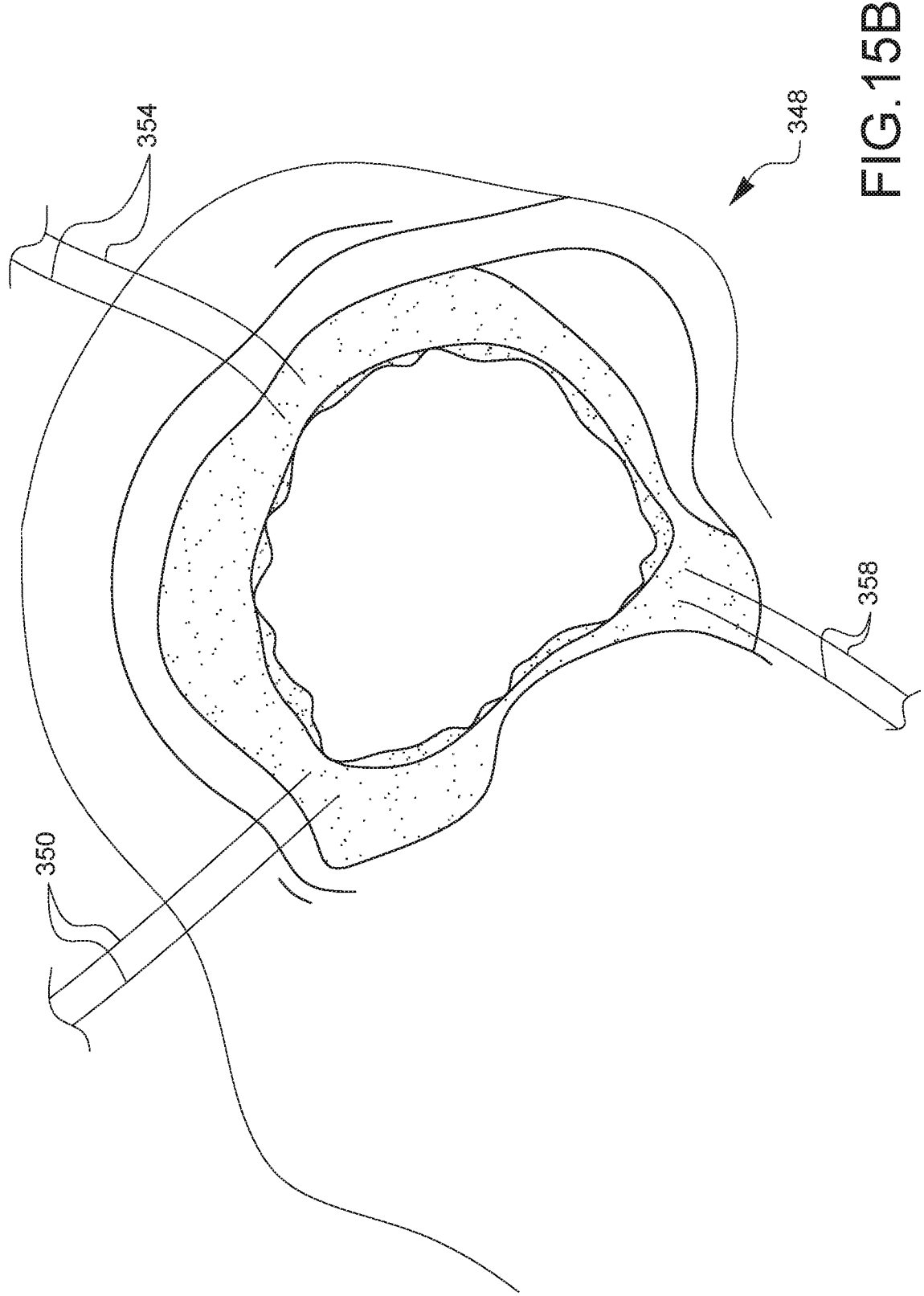

FIGS. 15A-15J, 15K-15N, and 15P-15Q are a series of views detailing portions of a surgical procedure using the aortic root retractor (ARR) delivery device of FIG. 11. FIGS. 15I and 15O were not used to avoid confusion with numerals one and zero, respectively. FIG. 15A is a view of the aortic annulus 348 in preparation for a minimally invasive surgical procedure involving the retraction and stabilization of cardiac tissue, including the aortic root. Three commissural stay sutures—an L-Non commissural stay suture 358, an L-R commissural stay suture 350, and an R-Non commissural stay suture 354—have been placed in each of the L-Non commissure 360, L-R commissure 352, and R-Non commissures 356. The L-Non commissural stay suture 358, L-R commissural stay suture 350, and R-Non commissural stay suture 354 extend out of a minimally invasive surgical site (not shown in this view). The locations of the right coronary sinus 353, non-coronary sinus 357, and left coronary sinus 361 are also indicated. FIG. 15B is a view of the aortic annulus 348 of FIG. 15A. The L-Non commissural stay suture 358, L-R commissural stay suture 350, and R-Non commissural stay suture 354 are shown in place, and the aortic valve leaflets have been removed. FIG. 15C is a view of the aortic annulus 348 of FIG. 15A. In this view a sound 362 is probing the aortic annulus 348 prior to the delivery of the ARR frame 84 to determine an appropriate ARR frame size and an appropriate prosthetic valve size. This sizing decision would be determined and confirmed by visual inspections. The aortic annulus and the aortic root are better visualized during subsequent surgical procedures with the ARR frame 84 inserted.

Figure 15D:
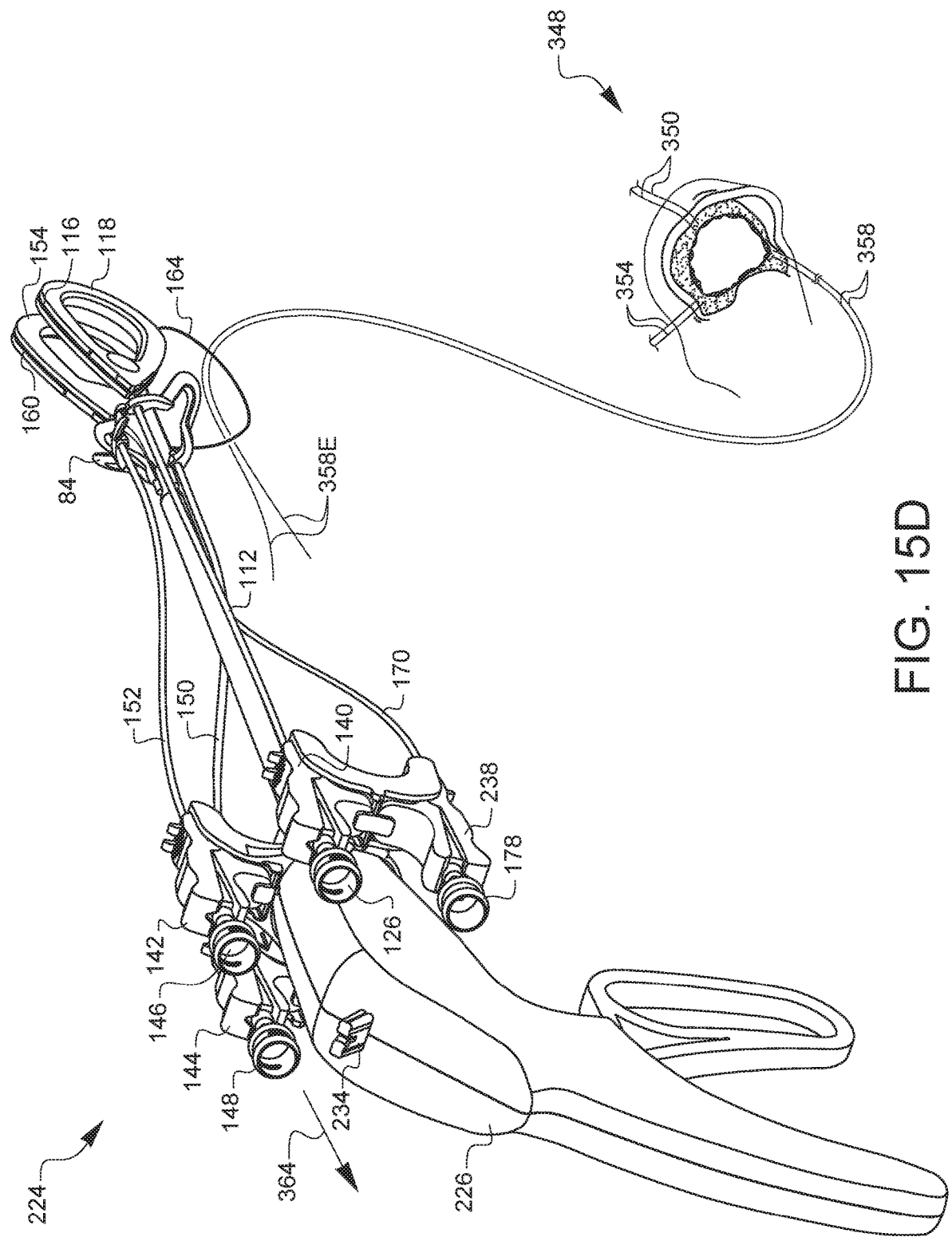
Figure 15E:
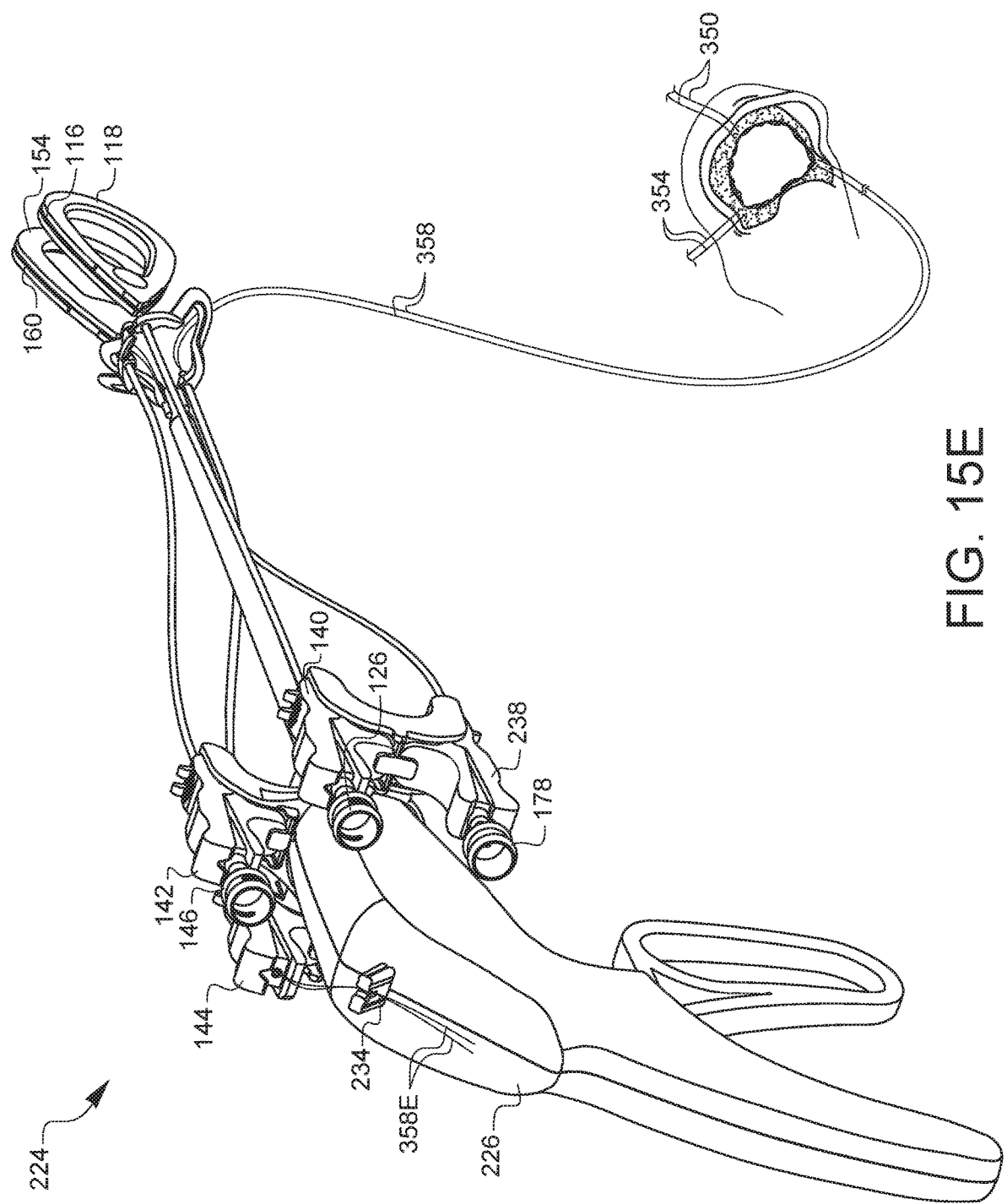

FIG. 15D is a proximal-top-left perspective view of the ARR frame introduction device 224 of FIG. 11 prepared for use in a surgical procedure with the aortic annulus 348 in view. The L-Non snare loop 164 has been exposed, with the target 156 having been removed as described previously. The L-Non commissure suture ends 358E or tails have been passed through the L-Non snare loop 164. The metal snare tab or chalice 148 mounted onto the L-Non suture locking apparatus 142 is then pulled in a proximal direction 364 in order to pull the L-Non commissure stay suture 358 through the L-Non suture tube 150 and into the L-Non suture locking apparatus 142. FIG. 15E is a proximal-top-left perspective view of the ARR frame introduction device 224 of FIG. 11 in use in a surgical procedure with the aortic annulus 348 in view. The L-Non commissure suture ends 358E are held within the tether 234. This and other suture ends may be further secured by the thumb of the operator's hand while resting on the housing 226 of the ARR frame delivery device 224. The steps described in regard to FIG. 15D are subsequently repeated (but not shown in this view) with the L-R commissure stay suture ends 350E, L-R chalice 148, L-R suture locking apparatus 144, and with the R-Non commissure stay suture ends 354E, R-Non chalice 126, R-Non suture locking apparatus 140, respectively. The L-Non suture locking apparatus 142, L-R suture locking apparatus 144, and R-Non suture locking apparatus 140 are not locked at this stage, and no action is taken relative to the deployment suture locking apparatus 238 at this stage.

Figure 15F:
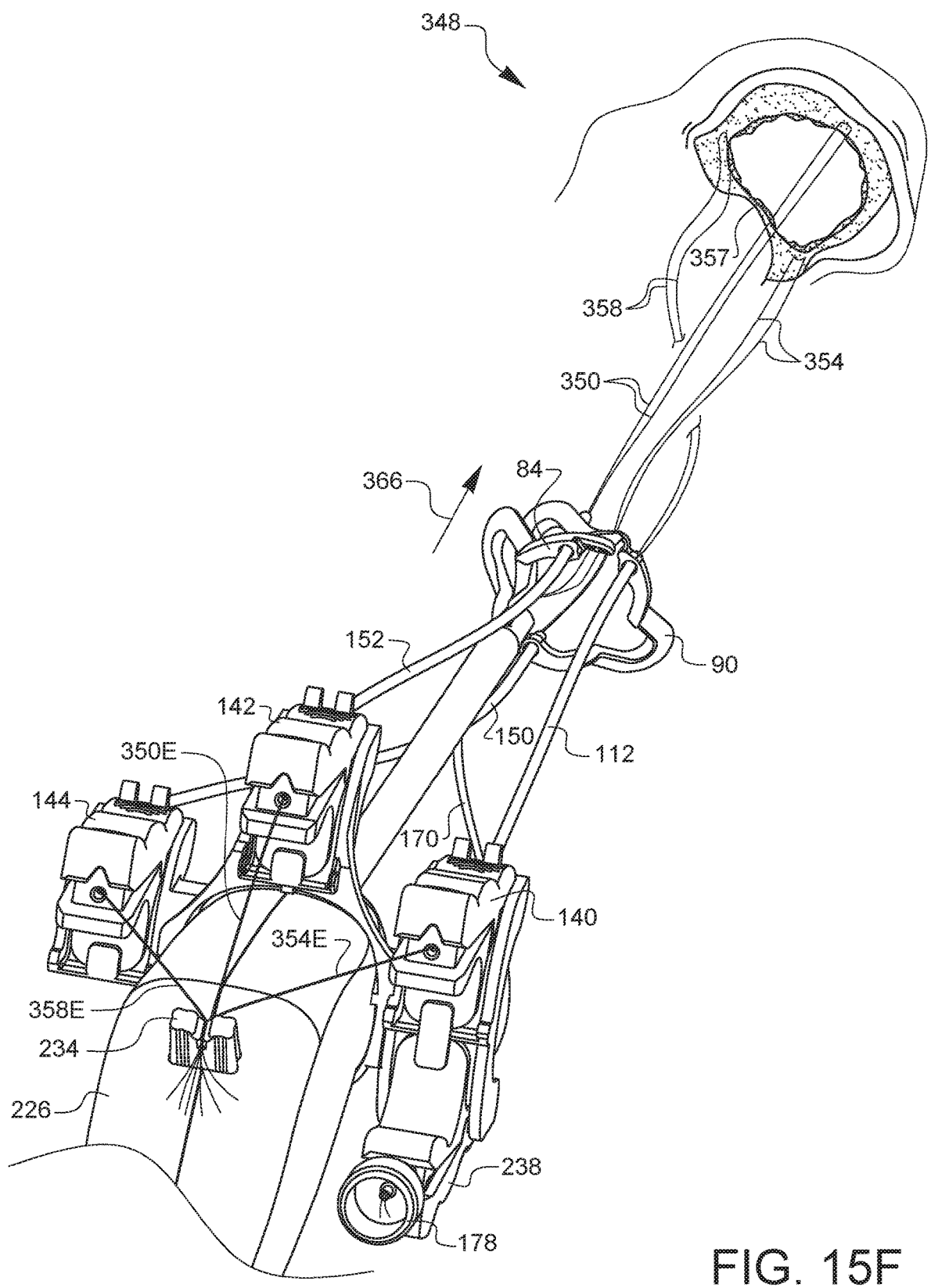
Figure 15G:
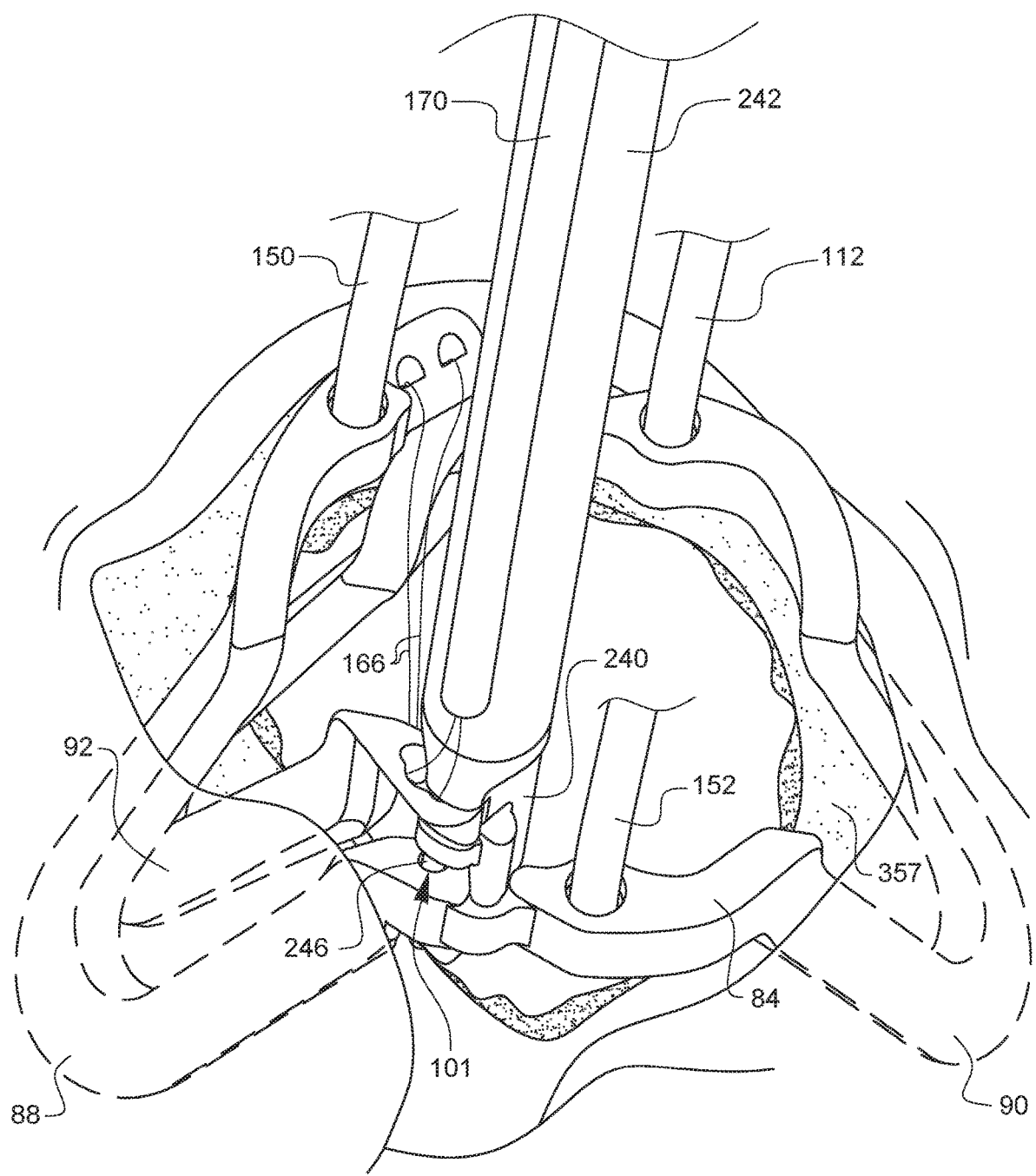

FIG. 15F is an enlarged proximal-top perspective view of the ARR frame introduction device 224 of FIG. 11 in use during a surgical procedure. The collapsed ARR frame 84 is delivered to the aortic annulus 348 by moving the device or parachuting the ARR frame 84 down along the commissural sutures 350, 354, 358 in a distal direction 366 towards the aortic annulus 348 while the operator grasps and takes up any slack on the suture ends 350E, 354E, and 358E behind the tether 234. The ARR frame 84 and its paddles are guided and oriented by the operator into the aortic root of the aortic annulus 348, with assistance by the use of forceps or one of the positioners 332, 333 on the introducer tip 240 if necessary. Initially, the second paddle 90 of the aortic root retractor frame 84 is oriented into the non-coronary sinus 357. While not completely shown in this view, the L-Non commissure stay suture 358 is fully pulled through the L-Non suture tube 150, positioning the L-Non suture tube 150 against the ARR frame 84, fully securing the ARR frame 84 to the aortic annulus 348 at the L-Non commissure stay suture location 360. While maintaining tension on the suture ends 350E, 354E, and 358E, the L-Non suture locking apparatus 142, L-R suture locking apparatus 144, and R-Non suture locking apparatus 140 are closed and locked. The L-Non suture locking apparatus 142, L-R suture locking apparatus 144, and R-Non suture locking apparatus 140 are each in turn removed from the suture lock organizer 232 of the ARR frame delivery device 224 and placed in the appropriate location on a suture management system and secured. This action of tightening each of the commissural stay sutures serves to align the suture tubes 112, 150, 152 and therefore the ARR frame 84 with the initial suture locations described in regard to FIG. 15A. FIG. 15G is an enlarged perspective view of the aortic annulus 348 with the collapsed or folded ARR frame 84 and the ARR frame introduction device 224 in their respective positions as described in regard to FIG. 15F. The relative locations of the second paddle 90 of the aortic root retractor frame 84 and the non-coronary sinus 357 should be noted. At this stage, the deployment suture locking apparatus 238 is removed from the suture lock organizer 232 of the ARR frame delivery device 224 and placed in a suture management system.

Figure 15H:
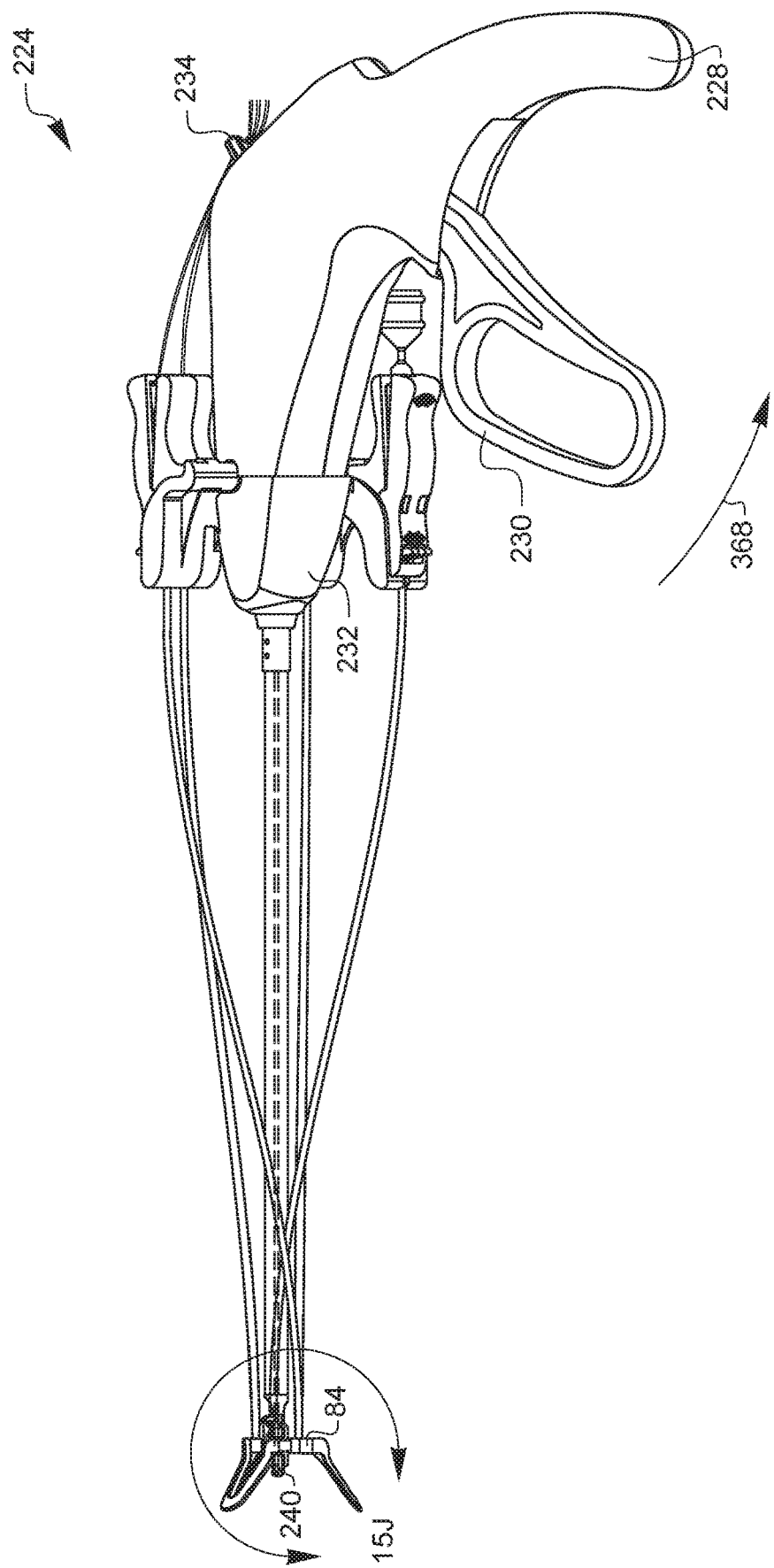

FIG. 15H is a bottom-left perspective view of the ARR frame introduction device 224 of FIG. 11 shown with the introducer pin 246 in an engaged position. FIGS. 15H and 15J-15N illustrate the ARR frame delivery device 224 outside of the surgical context and in the absence of tissue in order to clearly represent the operation of the ARR frame introduction device 224. The ARR frame introduction device 224 is shown with the actuation lever 230 released in a direction away from the handle 228. FIG. 15J is an enlarged partial cross-sectional view of the introducer end 240 of the ARR frame delivery device 224 of FIG. 15H. FIG. 15J shows the ARR frame 84 loaded into the introducer end 240, with the introducer pin 246 engaged through suture guide 101 in the second geometric mating feature 98 of the ARR frame 84, which is held within the proximal frame gap 342 of the introducer end 240, and the introducer pin 246 engaged through the pin receiving orifice 106 of the ARR frame 84, which is held within the distal frame gap 344 of the introducer end 240. To begin the release of the ARR frame 84, the actuator lever 230 is squeezed in a direction towards 368 the handle 228.

Figure 15K:
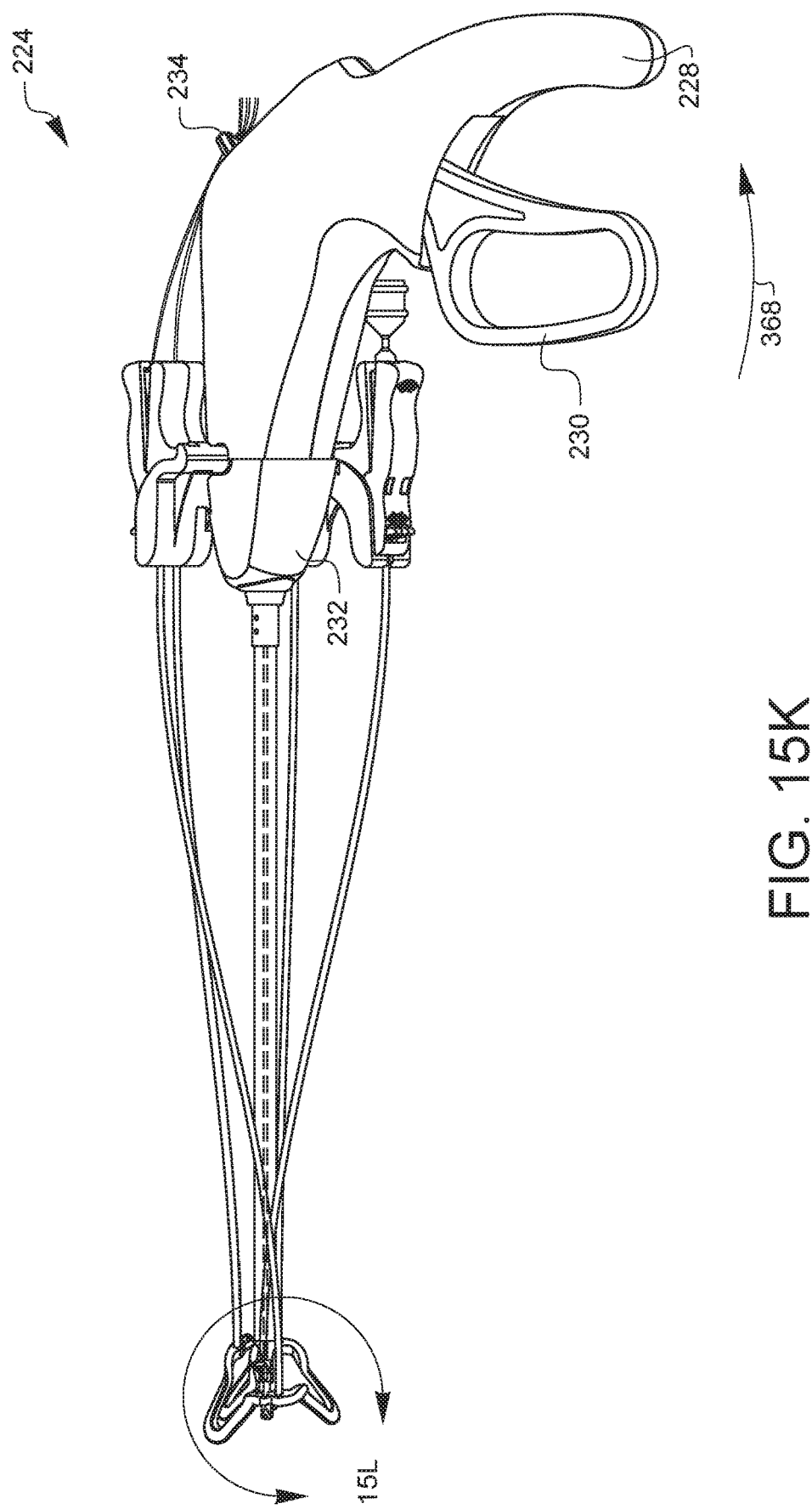
Figure 15L:
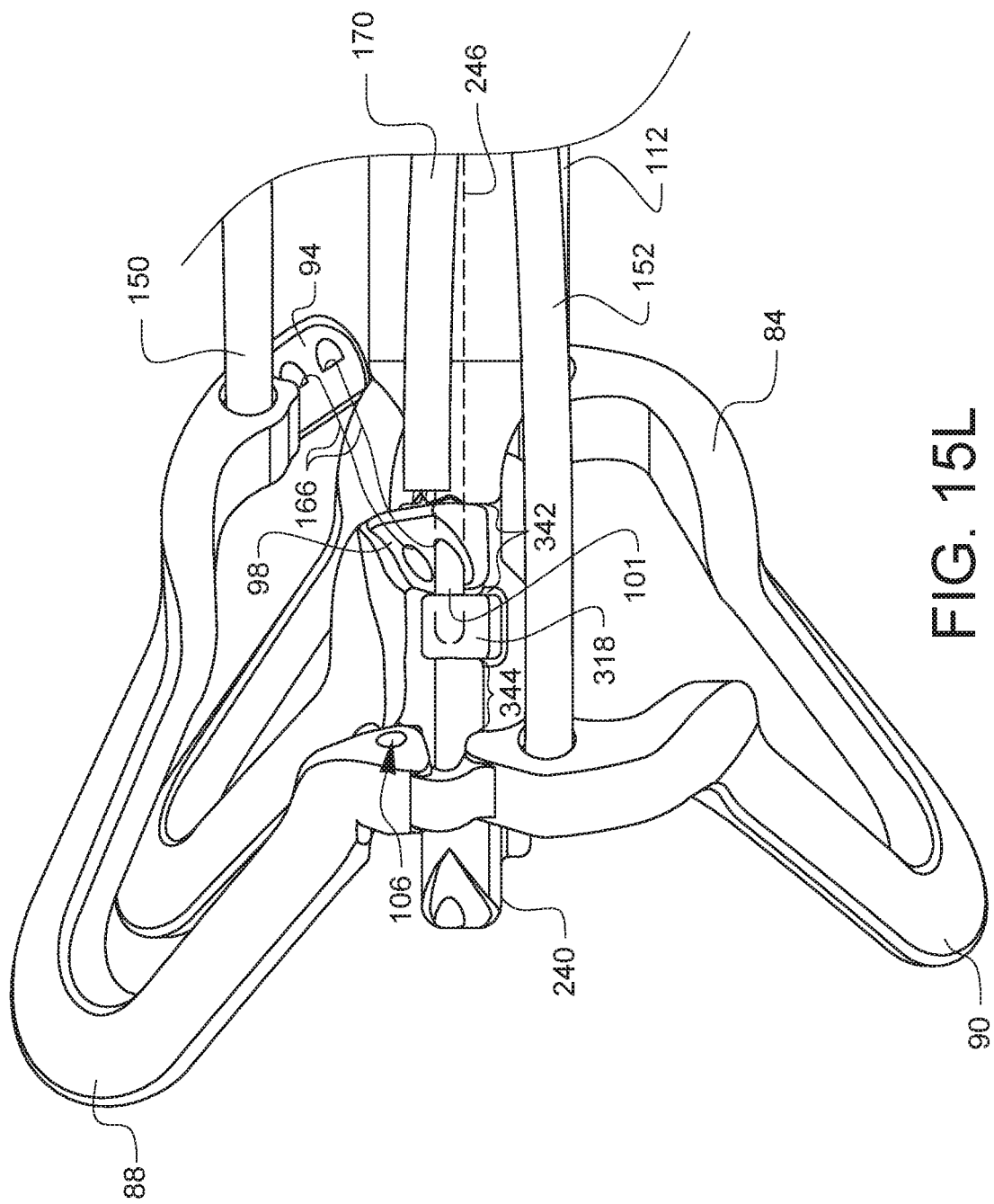

FIG. 15K is a bottom-left perspective view of the ARR frame introduction device 224 of FIG. 11 shown with the introducer pin 246 in a partially released position. The actuation lever 230 is partially squeezed in a direction towards 368 the handle 228, which retracts the introducer pin 246 partially away from the introducer end 240. This moves the introducer pin 246, as shown in the enlarged view of FIG. 15L, out of the distal frame gap 344 of the introducer end 240. This also releases the introducer pin 246 from the pin receiving orifice 106 of the ARR frame 84, allowing the ARR frame 84 to partially unfold. The introducer pin 246 remains in the bridge of the introducer end 240 and in suture guide 101 of the ARR frame 84, thereby retaining the suture guide 101 of the second geometric mating feature 98 end of the ARR frame 84 in the proximal frame gap 342 of the introducer end 240 of the ARR frame introduction device 224. At this stage, the first paddle 88 of the folded ARR frame 84 is released and is guided past the L-R commissure 352 and into the aortic annulus 348.

Figure 15M:
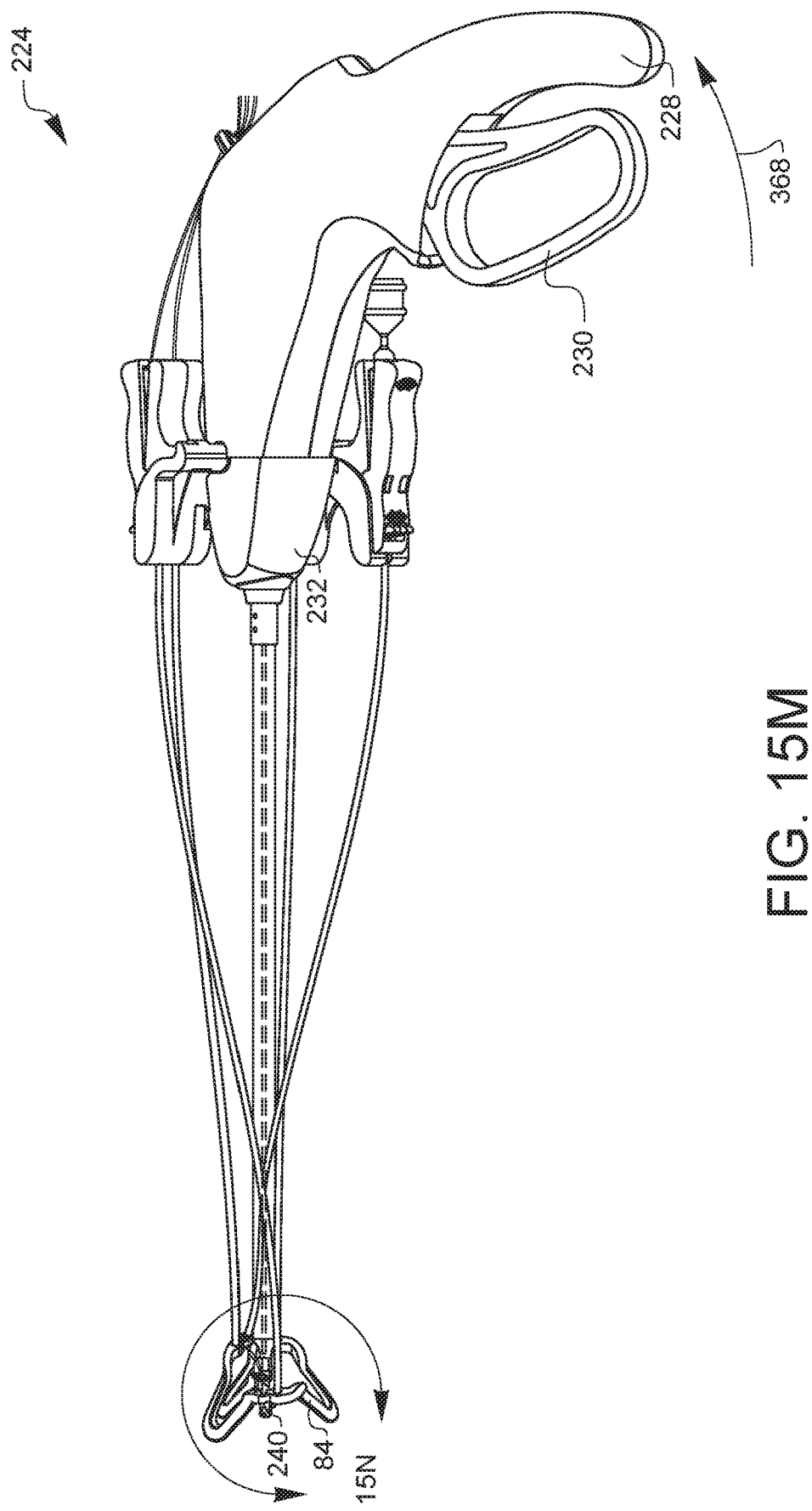
Figure 15N:
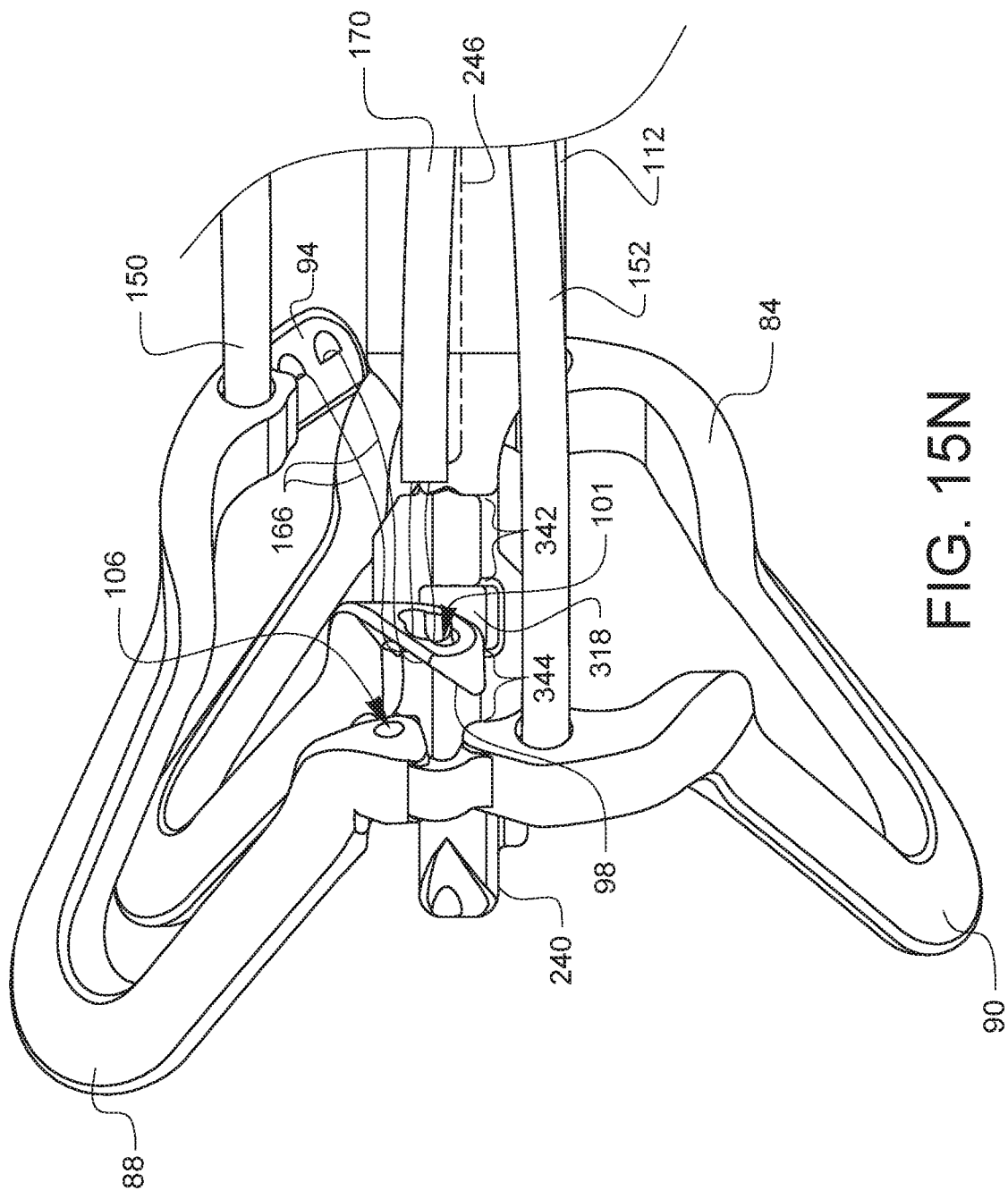

FIG. 15M is a bottom-left perspective view of the ARR frame introduction device 224 of FIG. 11 shown with the introducer pin 246 in a fully released position. The actuation lever 230 is fully squeezed in a direction 368 towards the handle 228, which retracts the introducer pin 246 fully away from the introducer end 240. This moves the introducer pin 246, as shown in the enlarged view of FIG. 15N, out of the proximal frame gap 342 on the introducer end 240. This releases the introducer pin 246 from suture guide 101 of the second geometric mating feature 98 end of the ARR frame 84, allowing the ARR frame 84 to be fully released from the ARR frame introducer device 224. The introducer pin 246 is fully retracted, thereby releasing the ARR frame 84 from the proximal frame gap 342 of the introducer end 240 of the ARR frame introduction device 224.

Figure 15P:
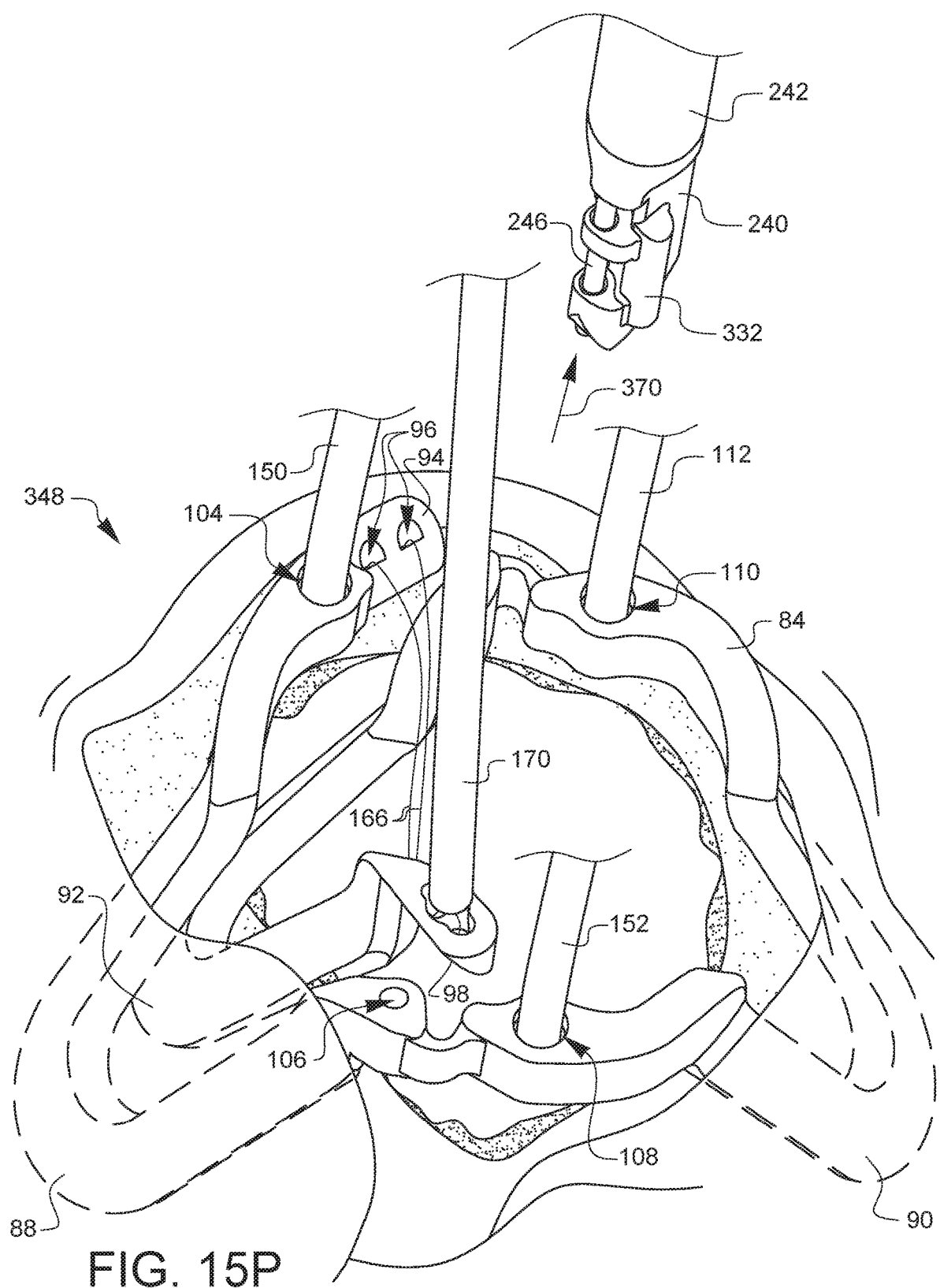
Figure 15Q:
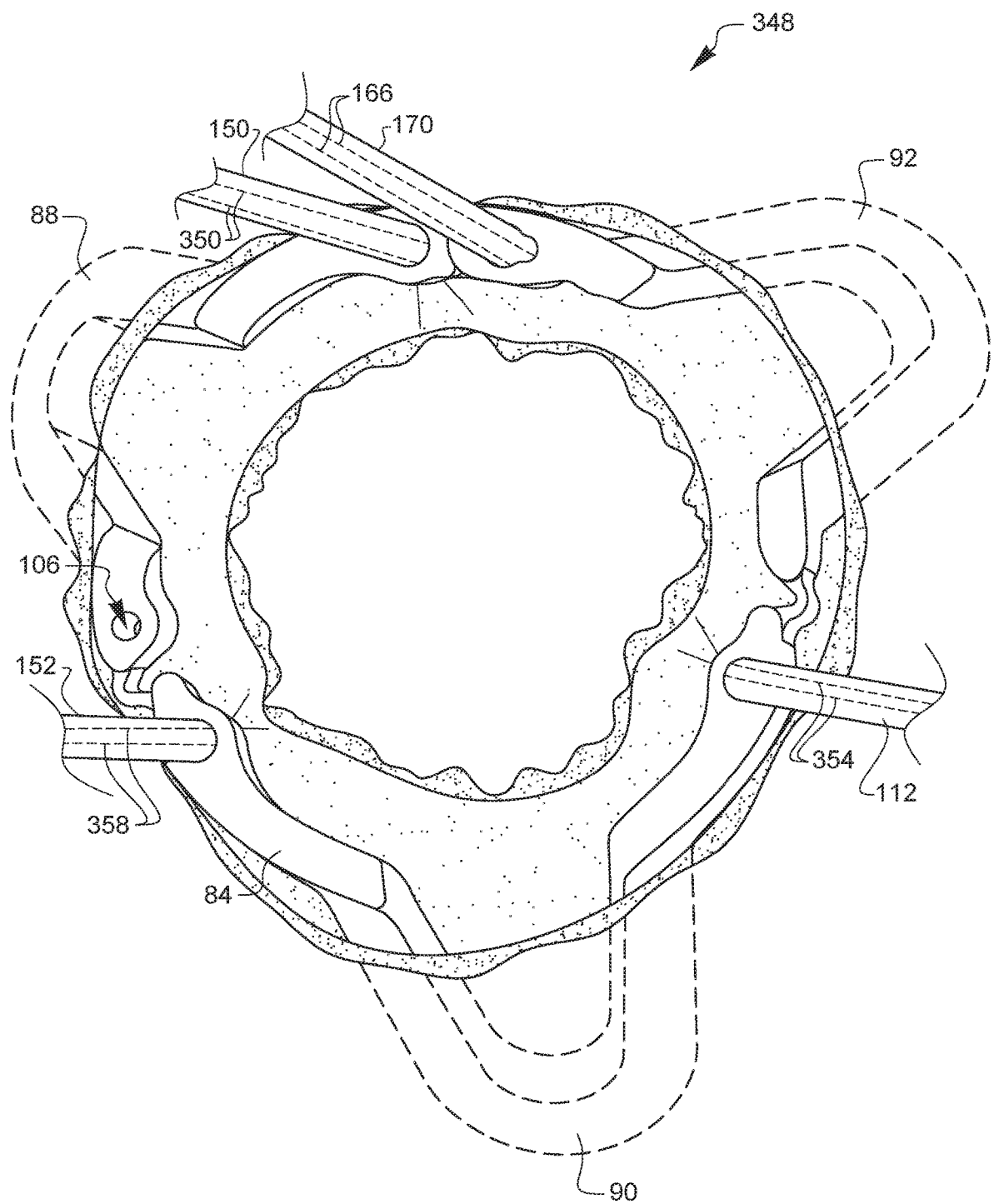

FIG. 15P is an enlarged perspective view of the ARR frame introduction device 224 of FIG. 11 in use during a surgical procedure. Once the ARR frame 84 is fully released from the introducer tip 240 as described in regard to FIGS. 15M and 15N, the ARR frame delivery device 224 may be removed from the aortotomy or surgical location in a proximal direction 370 away from the patient. The deployment suture lock apparatus 238 and its corresponding metal snare tab or chalice 178 is pulled away from the deployment suture lock apparatus 238 to fully expand the ARR frame 84 within the aortic annulus 348. The deployment suture lock apparatus 238 is then locked and the deployment suture lock apparatus 238 and its deployment suture tube 170 are set aside in a suture management apparatus. FIG. 15Q is a perspective view of the aortic annulus 348 with the ARR frame 84 fully deployed and secured.

Once the aortic annulus 348 is prepared for subsequent surgical procedure steps, the ARR frame 84 is removed, for example, before a prosthetic valve is parachuted down to the annulus. To release and remove the ARR frame 84, the suture locking apparatus 144, 142, 140, 238 are unlocked and their respective suture tubes 150, 152, 112 and the deployment suture tube 170 are released. All sutures are cut and removed, the ARR frame 84 is unfolded from around the annulus sutures, then retrieved by forceps or an alternate grasper. Finally, the three commissural stay sutures 350, 354, 358 are removed from the surgical site. While the preceding procedural steps described in regard to FIGS. 15A-15J, 15K-15N, and 15P-15Q have been disclosed, other alternative procedural steps to achieve similar results could potentially be completed using an ARR frame delivery device as described herein.

Figure 16B:
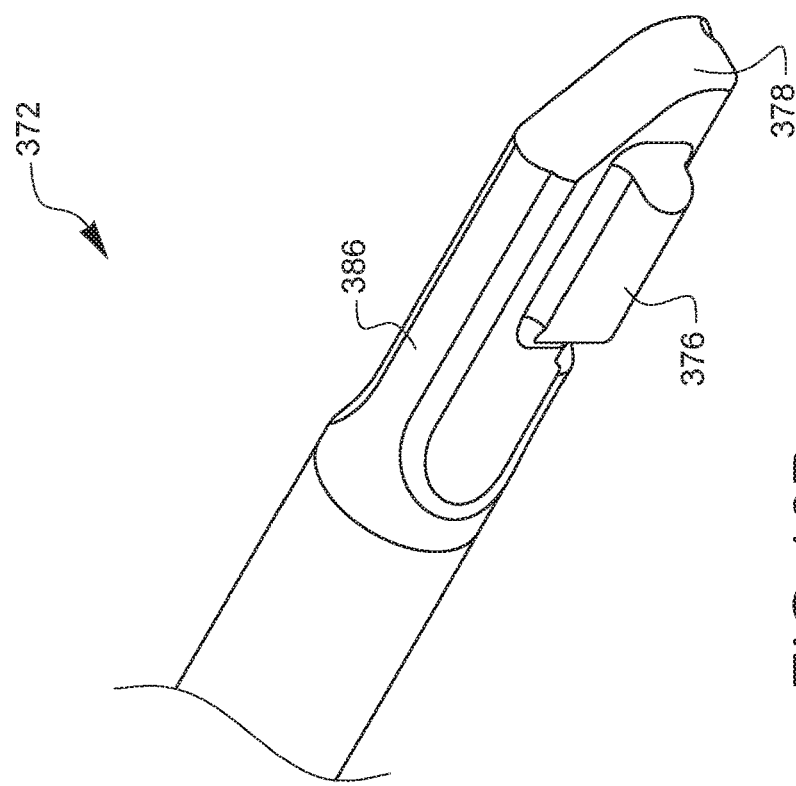
FIGS. 16A-16B are distal-top-right and distal-top-left perspective views of an alternate embodiment of an introducer end of an aortic root retractor (ARR) delivery device, respectively.
Figure 16A:
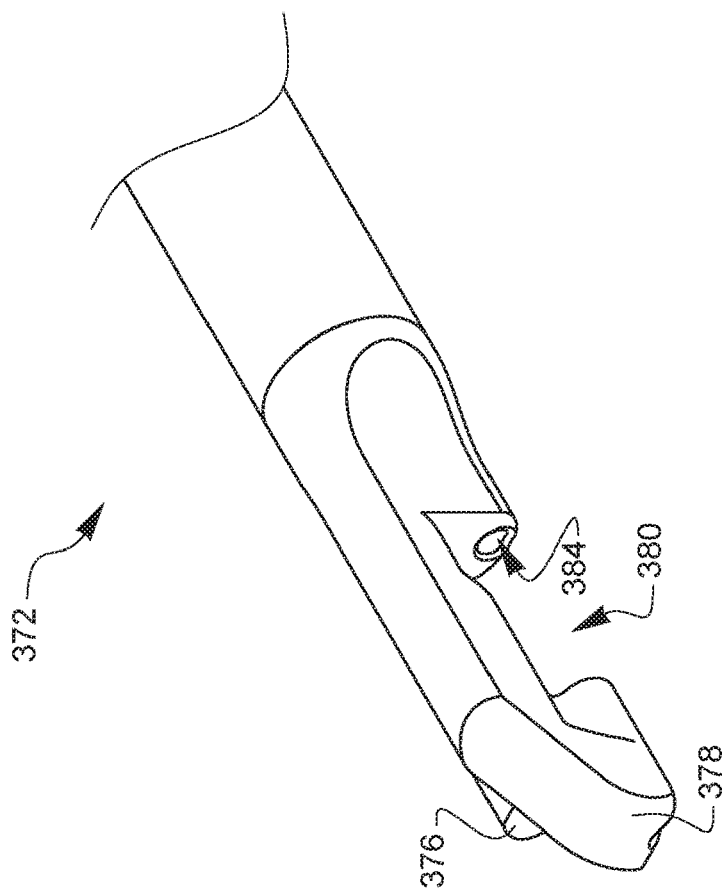

FIGS. 16A-16B are distal-top-right and distal-top-left perspective views of an alternate embodiment of an introducer end of an aortic root retractor (ARR) delivery device, respectively. The introducer end 372 defines a positioner 376, a blunt tip 378, a frame gap 380, and an introducer pin path 384 on the body 386 of the introducer end 372. The frame gap 380 is a space in the introducer tip 372 to accommodate a folded ARR frame 84 before deployment. The introducer pin path 384 accommodates the introducer pin 246 and is configured to guide and allow the introducer pin 246 to freely pass through the frame gap 380 to hold and release the folded ARR frame 84. The blunt tip 378 of the introducer end 372 is rounded or blunt and configured to reduce the potential of tissue trauma when using an aortic root retractor frame introduction device such as those described herein. The positioner 376 is a protrusion from the body 386 of the introducer end 372 configured to help position the ARR frame 84 into its final position before deployment during a surgical procedure.

Figure 17:
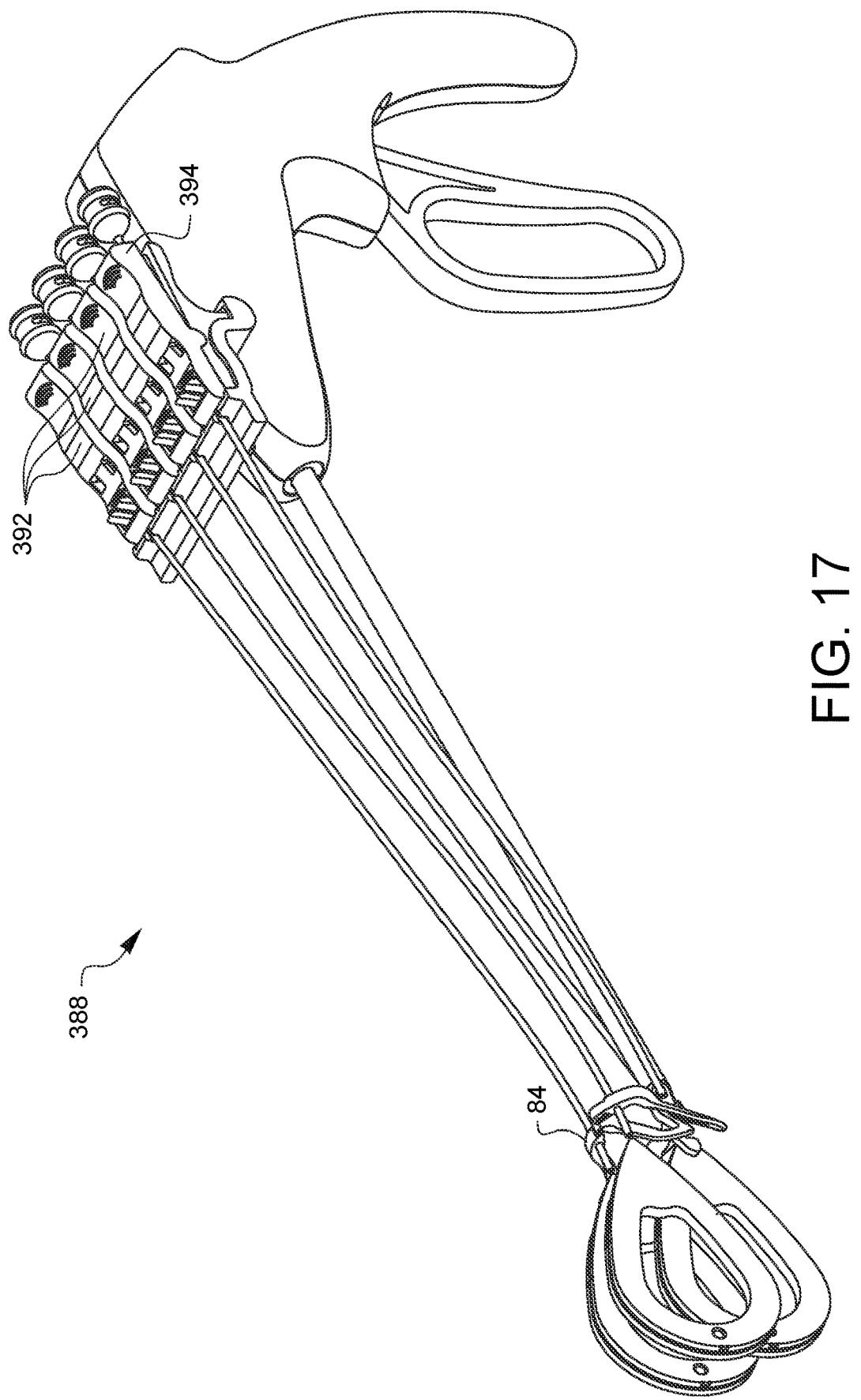
FIGS. 17-19 are distal-top-right perspective views of alternate embodiments of an aortic root retractor (ARR) delivery device.
Figure 18:
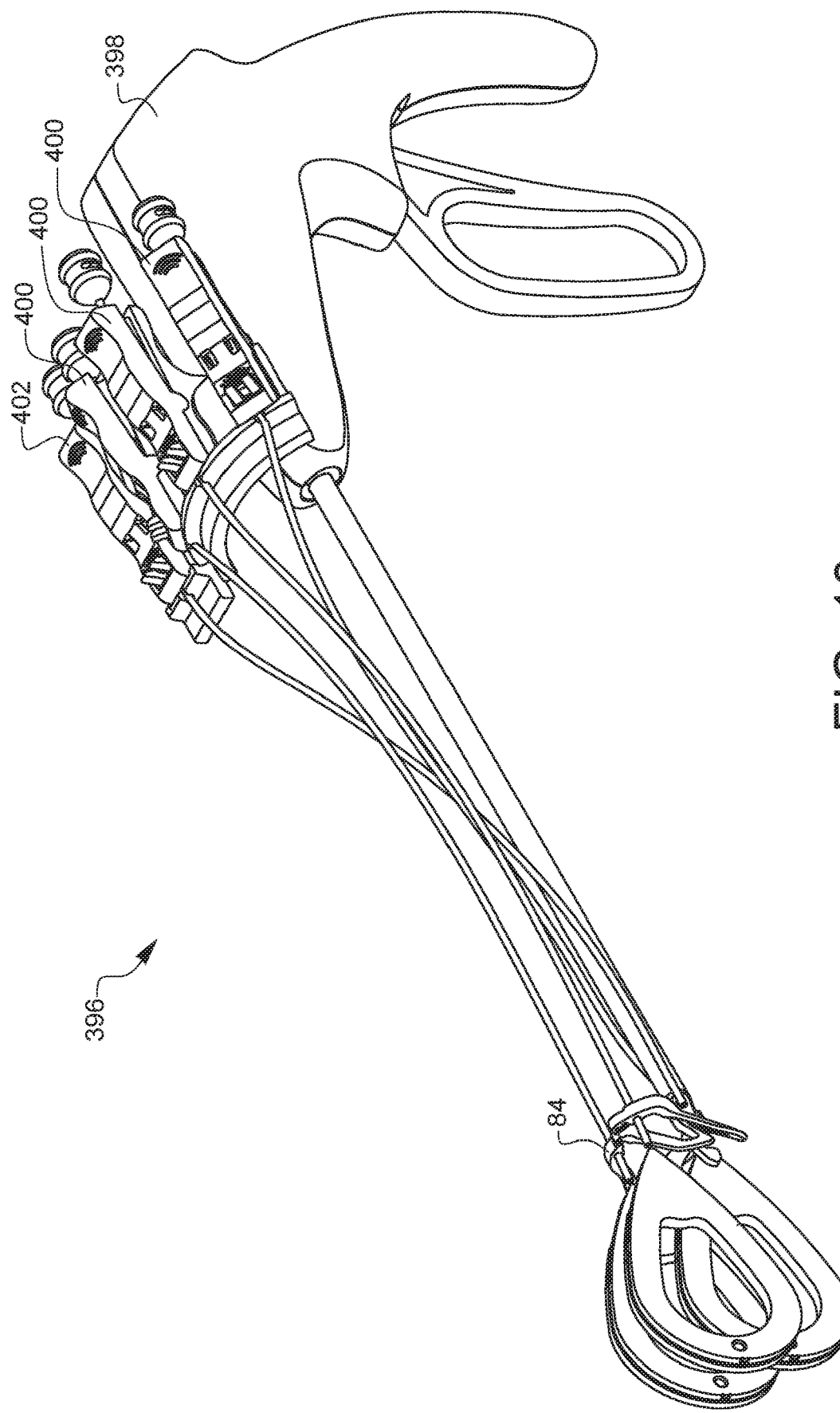
Figure 19:
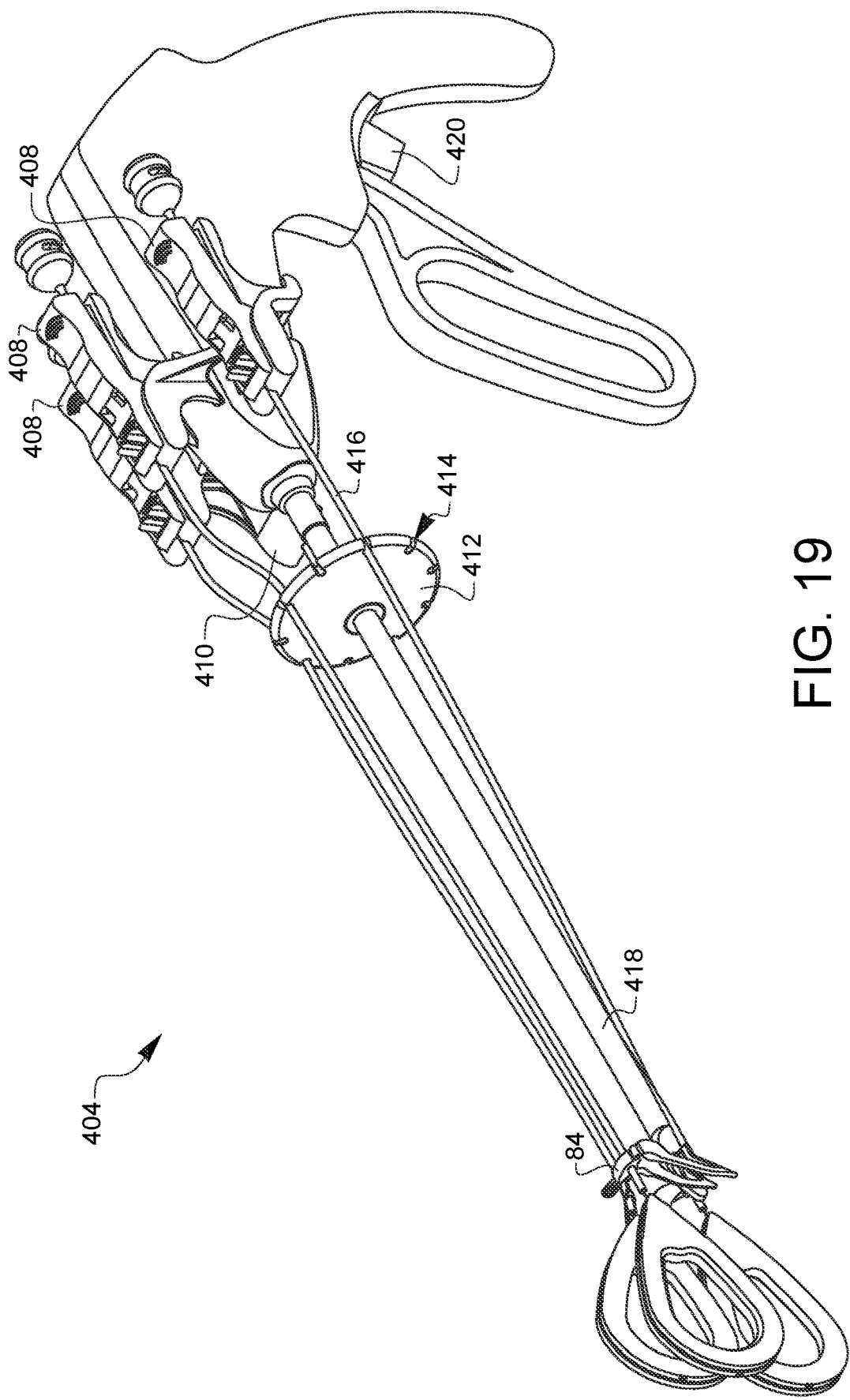

FIGS. 17-19 are distal-top-right perspective views of alternate embodiments of an aortic root retractor (ARR) delivery device. FIG. 17 is a distal-top-right perspective view of an alternate embodiment of an aortic root retractor frame introduction device. This embodiment of an aortic root retractor frame introduction device 388 illustrates a straight in-line orientation of the suture locking apparatus 392 and deployment suture locking apparatus 394. FIG. 18 is a distal-top-right perspective view of an alternate embodiment of an aortic root retractor frame introduction device 396. This embodiment illustrates a rounded orientation of the suture locking apparatus 400 and deployment suture locking apparatus 402. FIG. 19 is a distal-top-right perspective view of an alternate embodiment of an aortic root retractor frame introduction device 404. This embodiment shows an arrangement of the suture locking apparatus 408 and deployment suture locking apparatus 410 similar to the embodiment shown in FIG. 11, but with an additional tube guide wheel 412 attached to the shaft 418 used for improved organization of suture tubes 416. The suture tube guide wheel 412 defines several notches 414 around its circumference. These notches 414 are sized and configured to releasably hold via a light friction fit any number of suture tubes 416 for improved organization and management of suture tubes 416. This embodiment further has a lever block 420, which is a physical inhibitor to prevent the ARR frame introduction device 404 from being actuated prematurely.

Various advantages of devices for cardiac surgery have been discussed above. Embodiments discussed herein have been described by way of example in this specification. It will be apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. As just one example, although many of the embodiments shown herein included six suture guides, it should be understood that other embodiments may have more or fewer suture guides. As another non-limiting example, the suture guide holes shown in the embodiments herein are fully constrained holes. In other embodiments, the suture guide holes could be in communication with an access channel that would allow a suture to be brought into the suture guide hole by guiding a middle portion of a suture through the access channel and into the suture guide hole. This could avoid the need for a snare to pull the suture through the guide hole in some embodiments. Additionally, the recited order of processing elements or sequences, or the use of numbers, letters, or other designations, therefore, is not intended to limit the claims to any order, except as may be specified in the claims. Accordingly, the invention is limited only by the following claims and equivalents thereto.

What is claimed is:

1. A device for cardiac surgery, comprising:
an aortic root retractor frame comprising:
a first paddle having a U-shape;
a second paddle having a U-shape; and
a third paddle having a U-shape,
wherein a first end portion of the first paddle is pivotably coupled to a first end portion of the second paddle, wherein a second end portion of the second paddle is pivotably coupled to a first end portion of the third paddle, and wherein the aortic root retractor frame is displaceable from a first folded orientation, in which a second end portion of the first paddle is remote from a second end portion of the third paddle, to a second deployed orientation, in which the second end portion of the first paddle is adjacent to the second end portion of the third paddle;
an introducer comprising an introducer end disposed at a distal position of a shaft, wherein a portion of the aortic root retractor frame is configured to be releasably secured by the introducer end;
one or more suture locking apparatuses configured to be coupled to the introducer; and
a frame deployment mechanism configured to displace the aortic root retractor frame from the first folded orientation to the second deployed orientation.

2. The device for cardiac surgery of claim 1, wherein the aortic root retractor frame further comprises:
a plurality of tube orifices; and
a plurality of suture guides.

3. The device for cardiac surgery of claim 1, wherein the introducer further comprises:
a pin held within the introducer end through a pin path that travels throughout the length of the introducer end; and
an actuator coupled to the pin to selectively move the pin along the pin path, wherein a distal end portion of the pin is configured to be received through an aperture formed in a portion of the aortic root retractor frame to releasably secure the aortic root retractor frame to the introducer.

4. The device for cardiac surgery of claim 3, the actuator further comprising an actuation lever coupled to a proximal end of the pin, wherein a displacement of the actuation lever displaces the pin along the pin path to releasably secure the aortic root retractor frame to the introducer.

5. The device for cardiac surgery of claim 4, the actuator further comprising a housing, wherein the actuation lever is pivotably coupled to a first portion of the housing and a proximal end of the shaft is coupled to a second portion of the housing, and wherein at least a portion of the pin extends through an interior portion of the shaft.

6. The device for cardiac surgery of claim 1, wherein each of the one or more suture locking apparatuses further comprise:
an upper housing having a gripping surface;
a lower housing coupled to the upper housing and having a gripping surface; and
a latch.

7. The device for cardiac surgery of claim 6, wherein each of the one or more suture locking apparatuses further comprises a suture tube coupled to the lower housing.

8. The device for cardiac surgery of claim 6, wherein each of the one or more suture locking apparatuses further comprises a suture tube stop.

9. The device for cardiac surgery of claim 6, wherein each of the one or more suture locking apparatuses further comprises a suture channel.

10. The device for cardiac surgery of claim 1, wherein the frame deployment mechanism comprises the suture locking apparatus.

11. The device for cardiac surgery of claim 1, wherein each of the one or more suture locking apparatuses further comprises a suture tube.

12. The device for cardiac surgery of claim 1, wherein each of the one or more suture locking apparatuses comprise a unique identifier selected from the group consisting of a color, a text label, an image, a pattern, a texture, a size, and a shape.

13. The device for cardiac surgery of claim 1, further comprising a suture lock organizer.

14. The device for cardiac surgery of claim 1, wherein the second end portion of the first paddle is configured to be coupled to a first portion of a suture and the second end portion of the third paddle is configured to be coupled to a second portion of the suture such that when the suture is displaced, the second end portion of the first paddle is displaced towards the second end portion of the third paddle to displace the aortic root retractor frame from the first folded orientation to the second deployed orientation.

* * * * *